US012645878B2

(12) United States Patent
Mabey et al.

(10) Patent No.: US 12,645,878 B2
(45) Date of Patent: Jun. 2, 2026

(54) UTILIZING LANGUAGE MACHINE LEARNING MODELS FOR AUTONOMOUS EXECUTIONS OF COMPUTERIZED TECH-BIO EXPLORATION TOOLS

(71) Applicant: Recursion Pharmaceuticals, Inc., Salt Lake City, UT (US)

(72) Inventors: Benjamin John Mabey, Millcreek, UT (US); Caleb Ryan Phillips, Bobcaygeon (CA); Denton Hallar Greenfield, Evansville, IN (US); Geoffrey Alexander Munro Hunter, Toronto (CA); Joseph Elliott Carpenter, Bountiful, UT (US); Kristin Ann Clark, Lehi, UT (US); Marie Anne Evangelista, San Francisco, CA (US); Marissa Gerda Saunders, Salt Lake City, UT (US); Marta Marie Fay, Salt Lake City, UT (US); Michael Murphy Craig, Montreal (CA); Michel Moreau-Lapointe, Montreal (CA); Miranda Delaney Macaskill, Hamilton (CA); Sadie Rae Ingle, Suttons Bay, MI (US)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 19/000,321

(22) Filed: Dec. 23, 2024

(65) Prior Publication Data

US 2025/0225126 A1     Jul. 10, 2025

Related U.S. Application Data

(60) Provisional application No. 63/618,172, filed on Jan. 5, 2024.

(51) Int. Cl.
 *G06F 16/00* (2019.01)
 *G06F 16/242* (2019.01)
 (Continued)

(52) U.S. Cl.
 CPC ........ *G06F 40/279* (2020.01); *G06F 16/2428* (2019.01); *G06F 16/285* (2019.01);
 (Continued)

(58) Field of Classification Search
 CPC .... G06N 20/00; G06N 3/0409; G06N 3/0442; G06N 3/0464; G06N 3/0495;
 (Continued)

(56) References Cited

U.S. PATENT DOCUMENTS

2012/0197896 A1* 8/2012 Li ......................... G06F 16/313
                                                   707/E17.089
2020/0064348 A1   2/2020 Krall
                   (Continued)

OTHER PUBLICATIONS

International Search Report and Written Opinion as received in PCT/US2025/010118 dated Mar. 7, 2025.
(Continued)

*Primary Examiner* — Shyue Jiunn Hwa
(74) *Attorney, Agent, or Firm* — Keller Preece PLLC

(57) ABSTRACT

The present disclosure relates to systems, non-transitory computer-readable media, and methods for utilizing language machine learning model (LLM) as autonomous reasoners to navigate and execute multiple layers of a computerized bio-activity discovery pipeline of a tech-bio exploration system. In particular, the disclosed systems can utilize an LLM that learns to access one or more tech-bio exploration tools to execute one or more processes and/or tasks in a bio-activity discovery pipeline. For instance, the disclosed systems can provide an interactive query prompt interface to enable users to provide tech-bio queries (as
(Continued)

prompts) and utilize the LLM with the prompts to execute one or more tasks in the bio-activity discovery pipeline to generate and/or retrieve bio-activity data for the query. Moreover, the disclosed systems can utilize one or more LLMs to autonomously utilize and/or interact with one or more tech-bio tools in the bio-activity discovery pipeline to generate and/or obtain bio-activity data.

20 Claims, 35 Drawing Sheets

(51) Int. Cl.

| | |
|---|---|
| *G06F 16/28* | (2019.01) |
| *G06F 16/3329* | (2025.01) |
| *G06F 16/338* | (2019.01) |
| *G06F 40/279* | (2020.01) |
| *G06F 40/284* | (2020.01) |
| *G06N 3/0455* | (2023.01) |
| *G16C 20/50* | (2019.01) |

(52) U.S. Cl.
CPC ........ *G06F 16/3329* (2019.01); *G06F 16/338* (2019.01); *G06F 40/284* (2020.01); *G06N 3/0455* (2023.01); *G16C 20/50* (2019.02)

(58) Field of Classification Search
CPC .......... G06N 3/088; G06N 5/045; G06N 7/01; G06N 5/01; G06N 20/10; G06N 3/045; G06N 3/08; G06N 5/04; G06F 16/313; G06F 30/27; G06F 16/285; G06F 16/51; G06F 40/279; G06F 40/284; G06F 21/10; H04L 69/329; G16B 20/00; G16B 40/20; G16B 40/00
See application file for complete search history.

(56) References Cited

U.S. PATENT DOCUMENTS

| | | | |
|---|---|---|---|
| 2021/0089934 A1 | 3/2021 | Thornley et al. | |
| 2021/0357585 A1 | 11/2021 | Surdeanu et al. | |
| 2022/0181029 A1 | 6/2022 | Colley et al. | |
| 2022/0269853 A1 | 8/2022 | Itani | |
| 2023/0144683 A1* | 5/2023 | Chatterjee | G06N 3/088 |
| | | | 435/7.21 |
| 2023/0221684 A1* | 7/2023 | Kloepper | G06N 5/045 |
| | | | 700/28 |
| 2023/0237277 A1 | 7/2023 | Reza et al. | |

OTHER PUBLICATIONS

Andrew Dalke, Jérô Hert, and Christian Kramer, "mmpdb: An Open-Source Matched Molecular Pair Platform for Large Multiproperty Data Sets", Journal of Chemical Information and Modeling, vol. 56, Issue 5, pp. 902-910, May 17, 2018.

* cited by examiner

612d (b)

Figure 6C:
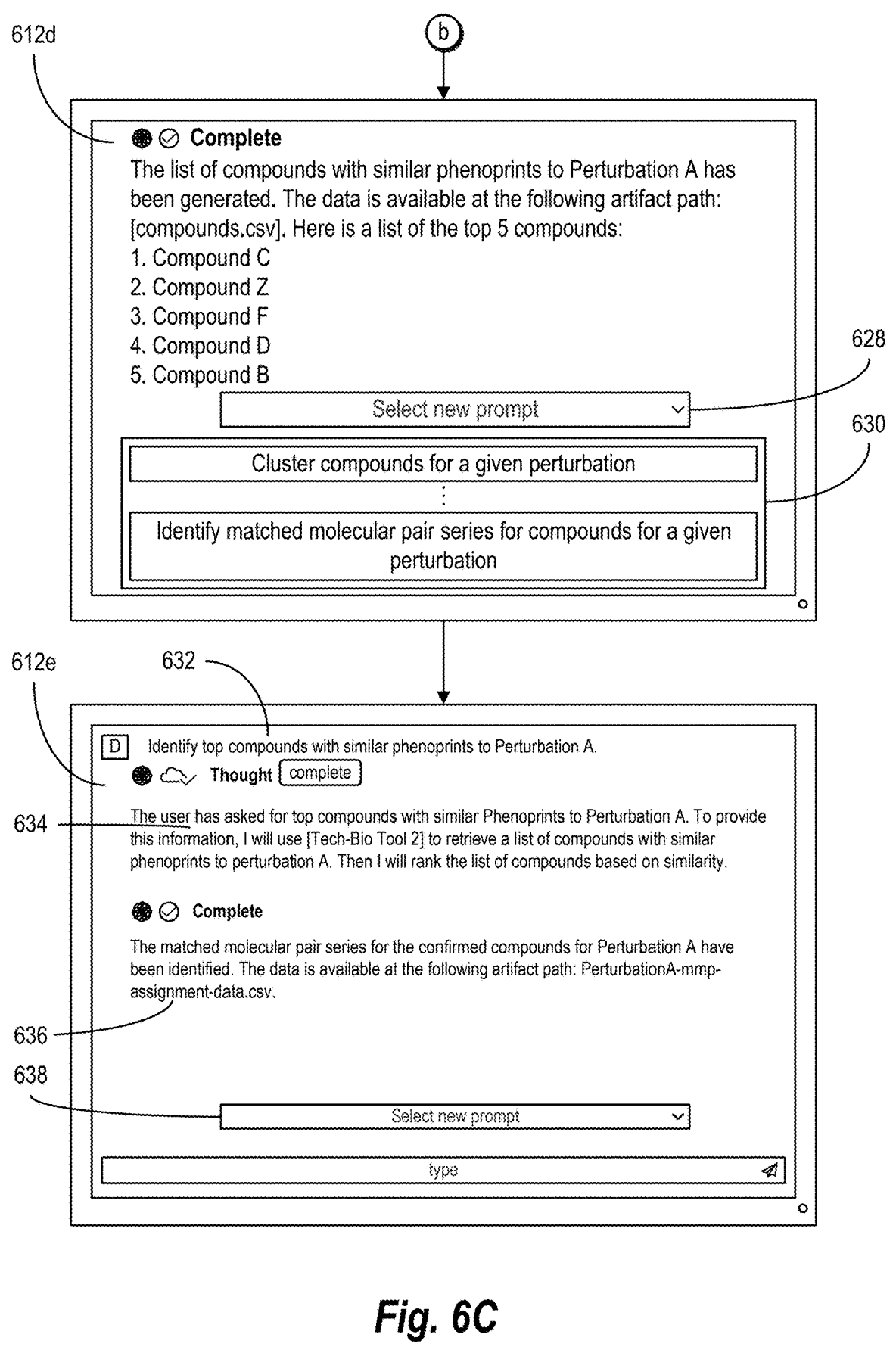

⬤ ⊘ Complete

The list of compounds with similar phenoprints to Perturbation A has been generated. The data is available at the following artifact path: [compounds.csv]. Here is a list of the top 5 compounds:
1. Compound C
2. Compound Z
3. Compound F
4. Compound D
5. Compound B

| Select new prompt ⌄ |
|---|

628

| Cluster compounds for a given perturbation |
|---|
| ⋮ |
| Identify matched molecular pair series for compounds for a given perturbation |

630

612e     632

[D]   Identify top compounds with similar phenoprints to Perturbation A.

⬤ ☁⌄ Thought [complete]

634

The user has asked for top compounds with similar Phenoprints to Perturbation A. To provide this information, I will use [Tech-Bio Tool 2] to retrieve a list of compounds with similar phenoprints to perturbation A. Then I will rank the list of compounds based on similarity.

⬤ ⊘ Complete

The matched molecular pair series for the confirmed compounds for Perturbation A have been identified. The data is available at the following artifact path: PerturbationA-mmp-assignment-data.csv.

636

638

| Select new prompt ⌄ |
|---|

| type     ✈ |
|---|

Figure 7C:
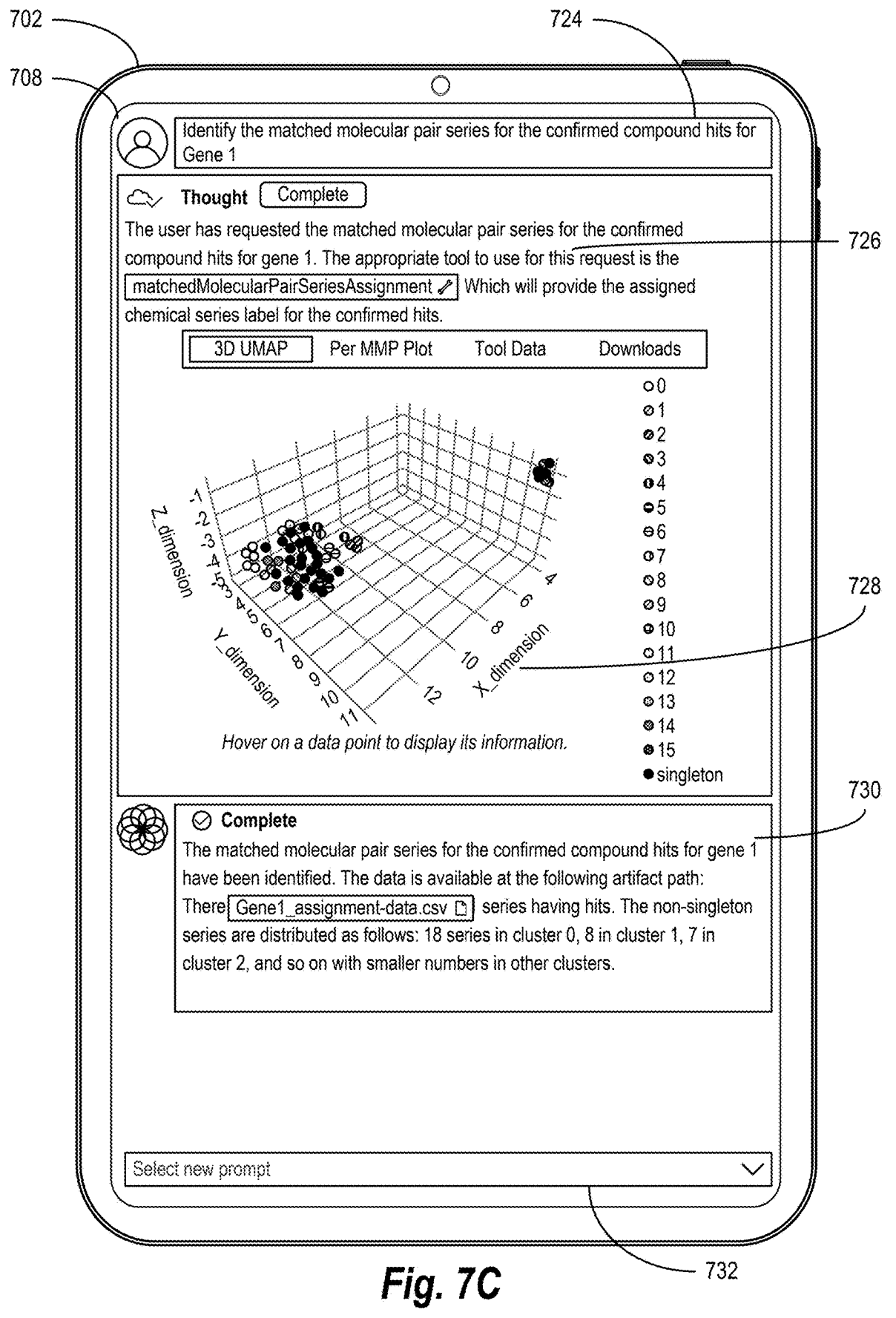

Identify the matched molecular pair series for the confirmed compound hits for Gene 1

Thought [Complete]

The user has requested the matched molecular pair series for the confirmed compound hits for gene 1. The appropriate tool to use for this request is the matchedMolecularPairSeriesAssignment ✎ Which will provide the assigned chemical series label for the confirmed hits.

| 3D UMAP | Per MMP Plot | Tool Data | Downloads |

○ 0
◉ 1
◉ 2
◉ 3
◉ 4
⊖ 5
◉ 6
◉ 7
◉ 8
◉ 9
◉ 10
○ 11
◉ 12
◉ 13
◉ 14
◉ 15
● singleton Z_dimension
Y_dimension
X_dimension

*Hover on a data point to display its information.*

⊘ Complete

The matched molecular pair series for the confirmed compound hits for gene 1 have been identified. The data is available at the following artifact path: There Gene1_assignment-data.csv 🗋 series having hits. The non-singleton series are distributed as follows: 18 series in cluster 0, 8 in cluster 1, 7 in cluster 2, and so on with smaller numbers in other clusters.

Select new prompt ⌄

Figure 7F:
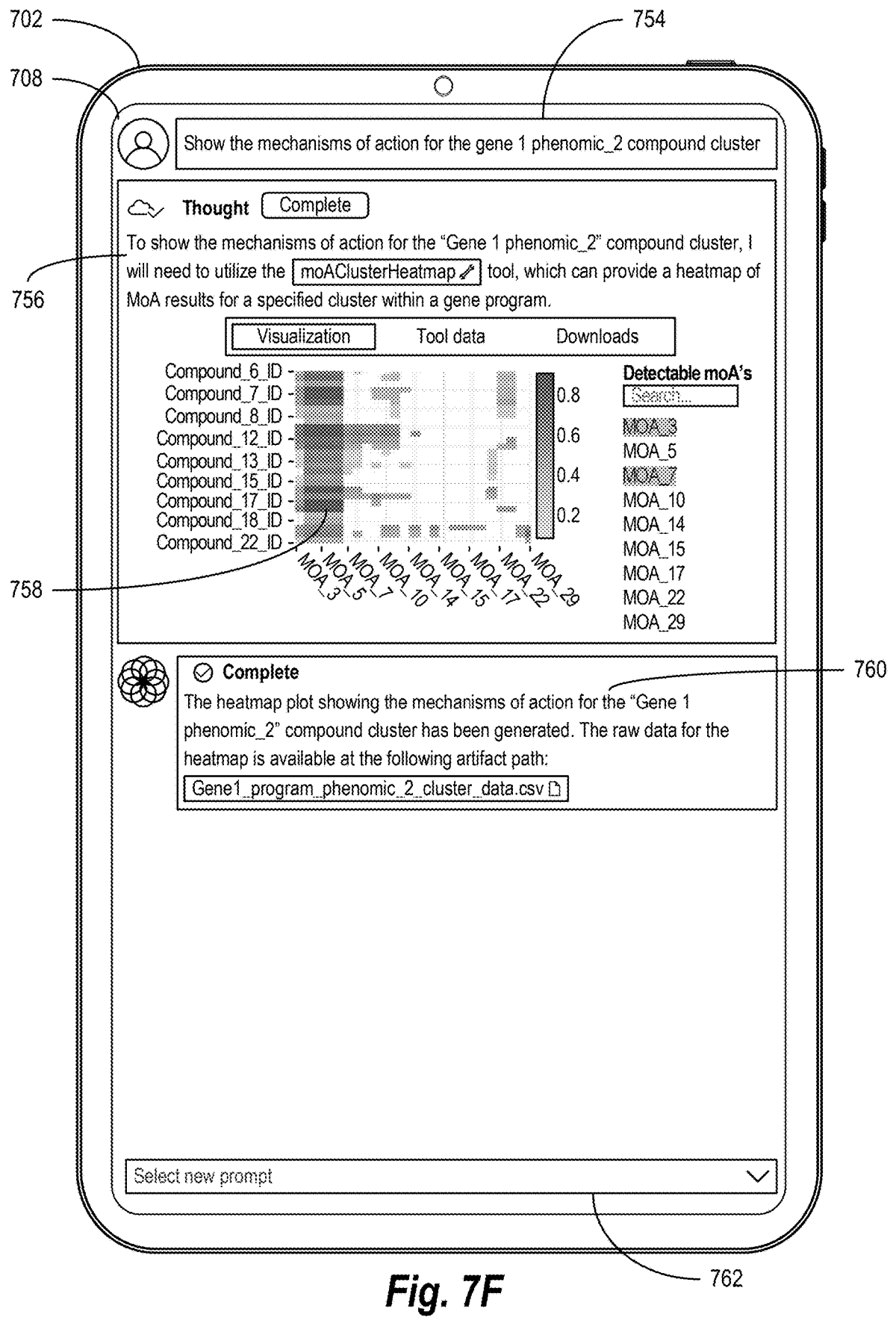

Show the mechanisms of action for the gene 1 phenomic_2 compound cluster

☁ Thought [ Complete ]

756

To show the mechanisms of action for the "Gene 1 phenomic_2" compound cluster, I will need to utilize the [ moAClusterHeatmap ✎ ] tool, which can provide a heatmap of MoA results for a specified cluster within a gene program.

[ Visualization ]    Tool data    Downloads

758

Detectable moA's

[ Search... ]

MOA_3
MOA_5
MOA_7
MOA_10
MOA_14
MOA_15
MOA_17
MOA_22
MOA_29

⊘ Complete

760

The heatmap plot showing the mechanisms of action for the "Gene 1 phenomic_2" compound cluster has been generated. The raw data for the heatmap is available at the following artifact path:

[ Gene1_program_phenomic_2_cluster_data.csv 🗋 ]

Select new prompt                                              ⌄

Figure 8D:
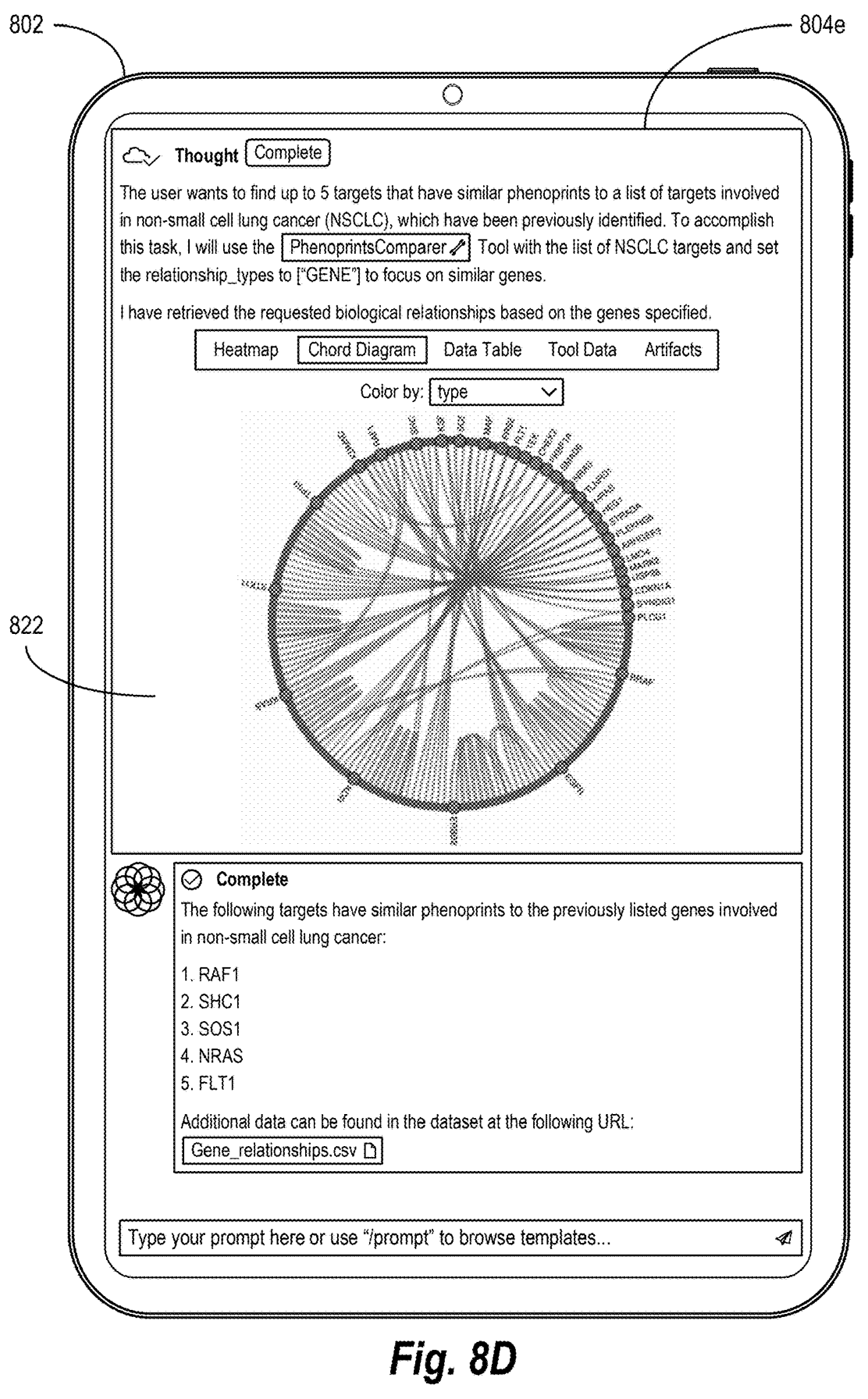

Thought [Complete]

The user wants to find up to 5 targets that have similar phenoprints to a list of targets involved in non-small cell lung cancer (NSCLC), which have been previously identified. To accomplish this task, I will use the [PhenoprintsComparer ✎] Tool with the list of NSCLC targets and set the relationship_types to ["GENE"] to focus on similar genes.

I have retrieved the requested biological relationships based on the genes specified.

| Heatmap | Chord Diagram | Data Table | Tool Data | Artifacts |

Color by: [type ⌄]

822

⊘ Complete

The following targets have similar phenoprints to the previously listed genes involved in non-small cell lung cancer:

1. RAF1
2. SHC1
3. SOS1
4. NRAS
5. FLT1

Additional data can be found in the dataset at the following URL:

[Gene_relationships.csv 📄]

Type your prompt here or use "/prompt" to browse templates... ➤

⊘ Complete

The following targets have similar phenoprints to the previously listed genes involved in non-small cell lung cancer:

1. RAF1
2. SHC1
3. SOS1
4. NRAS
5. FLT1

Additional data can be found in the dataset at the following URL:

Gene_relationships.csv 🗋

821

Use MatchMaker to find the top 100 active compounds for RAF1, compute their ADMET properties, filter them to keep the top 50 with the highest solubility.

☁ Thought [Complete]

To Find The Top 100 Active Compounds For RAF1, I Will Use The [MatchMakerAPI ✎] Tool. After Obtaining The List, I Will Compute Their ADMET Properties Using The [ADMETPrediction ✎] Tool. Once I Have The ADMET Data, I Will Use [TableAnalysis ✎] To Filter Out The Top 50 Compounds With The Highest Solubility.

824

I Have Retrieved Target To Compound Activity Relationships For The Following Targets: RAF1.

[Visualization]   Data Table      Tool Data      Artifacts

Select Coloring Option: [ Mm_score  ⌄ ]

826a

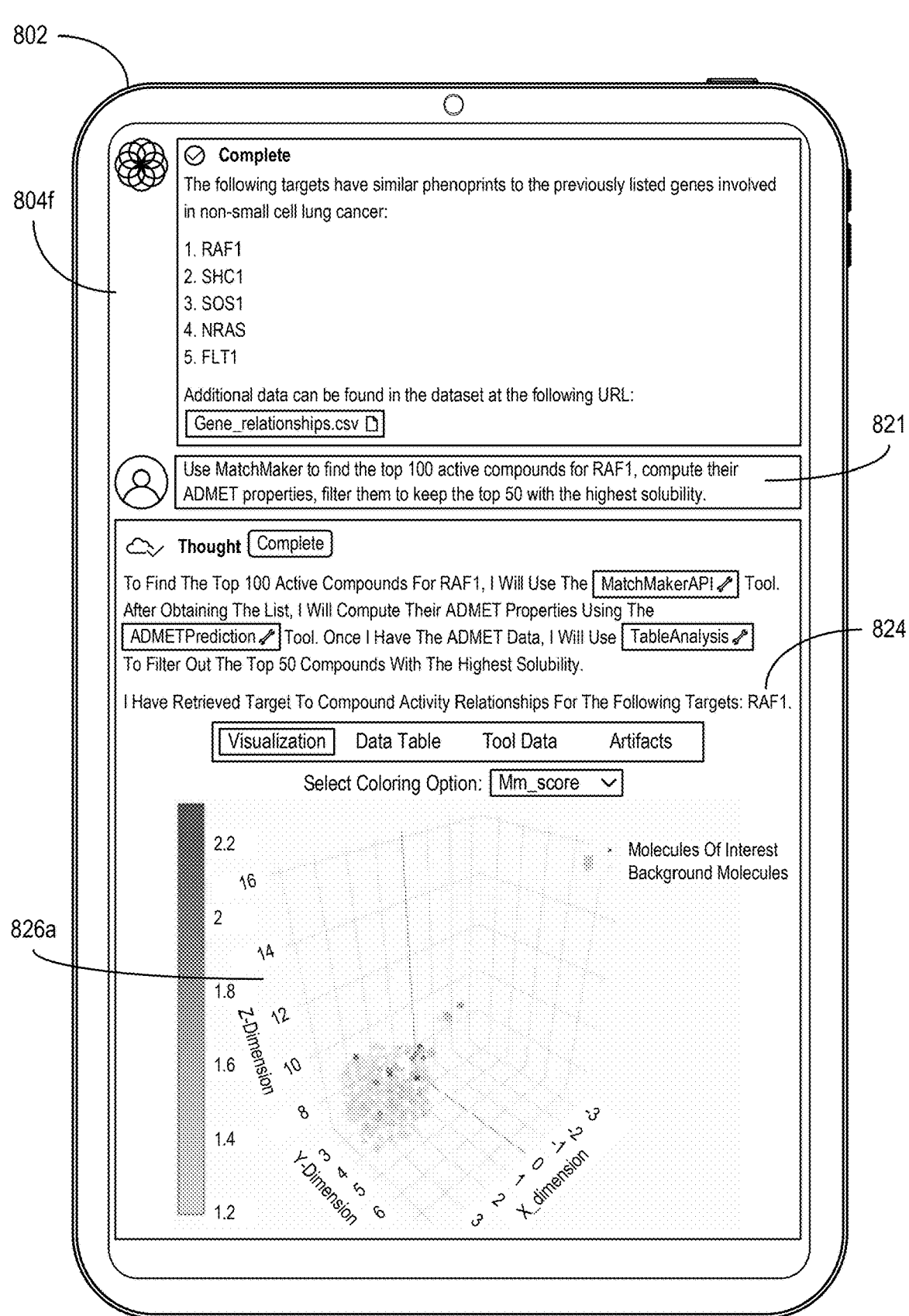

Molecules Of Interest
Background Molecules

Z-Dimension

Y-Dimension

X-dimension

Figure 8H:
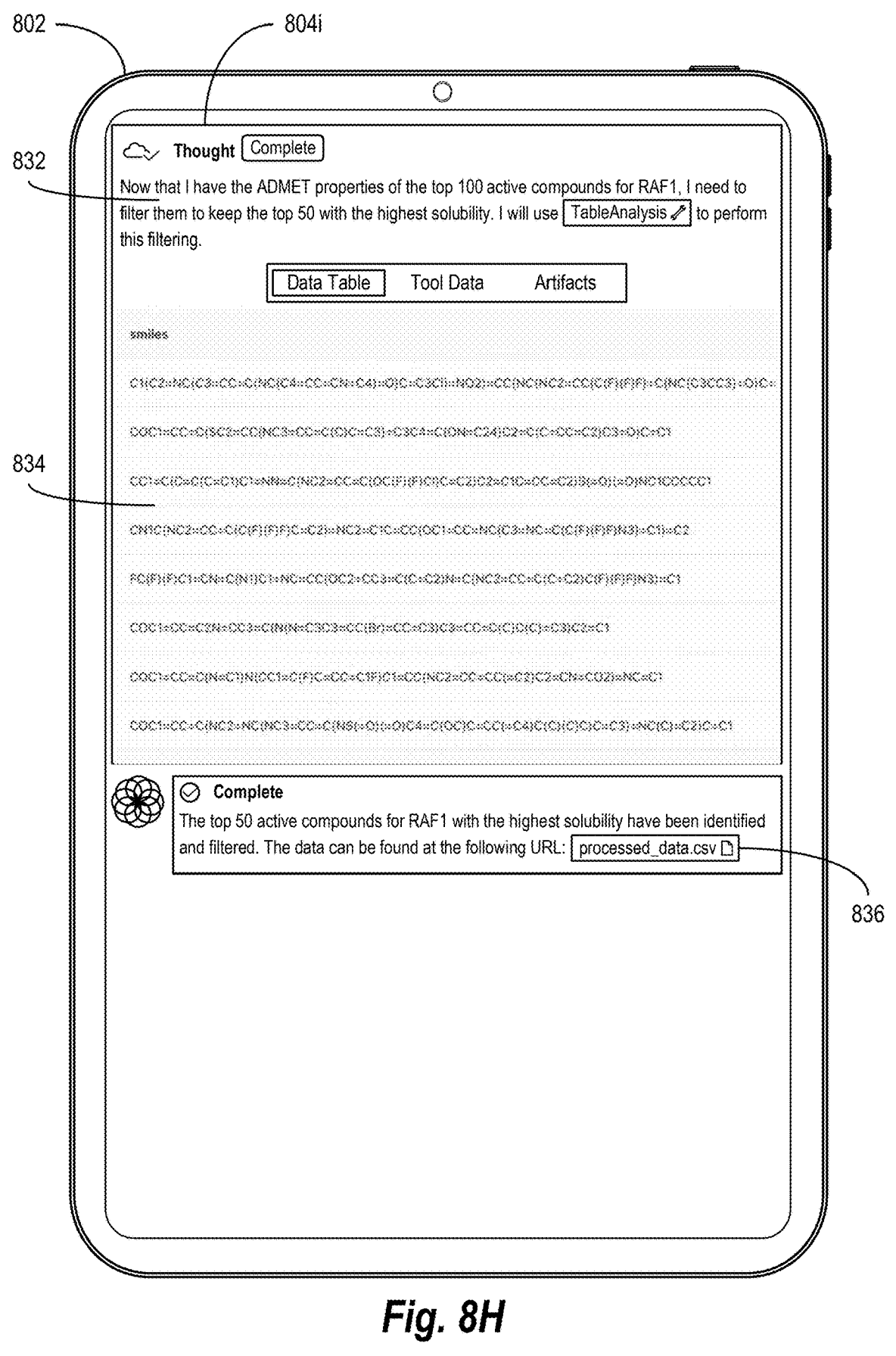

☁ Thought [ Complete ]

Now that I have the ADMET properties of the top 100 active compounds for RAF1, I need to filter them to keep the top 50 with the highest solubility. I will use [ TableAnalysis ✏ ] to perform this filtering.

[ Data Table     Tool Data     Artifacts ]

smiles

834

⊘ Complete

The top 50 active compounds for RAF1 with the highest solubility have been identified and filtered. The data can be found at the following URL: [ processed_data.csv 🗋 ]

Figure 8J:
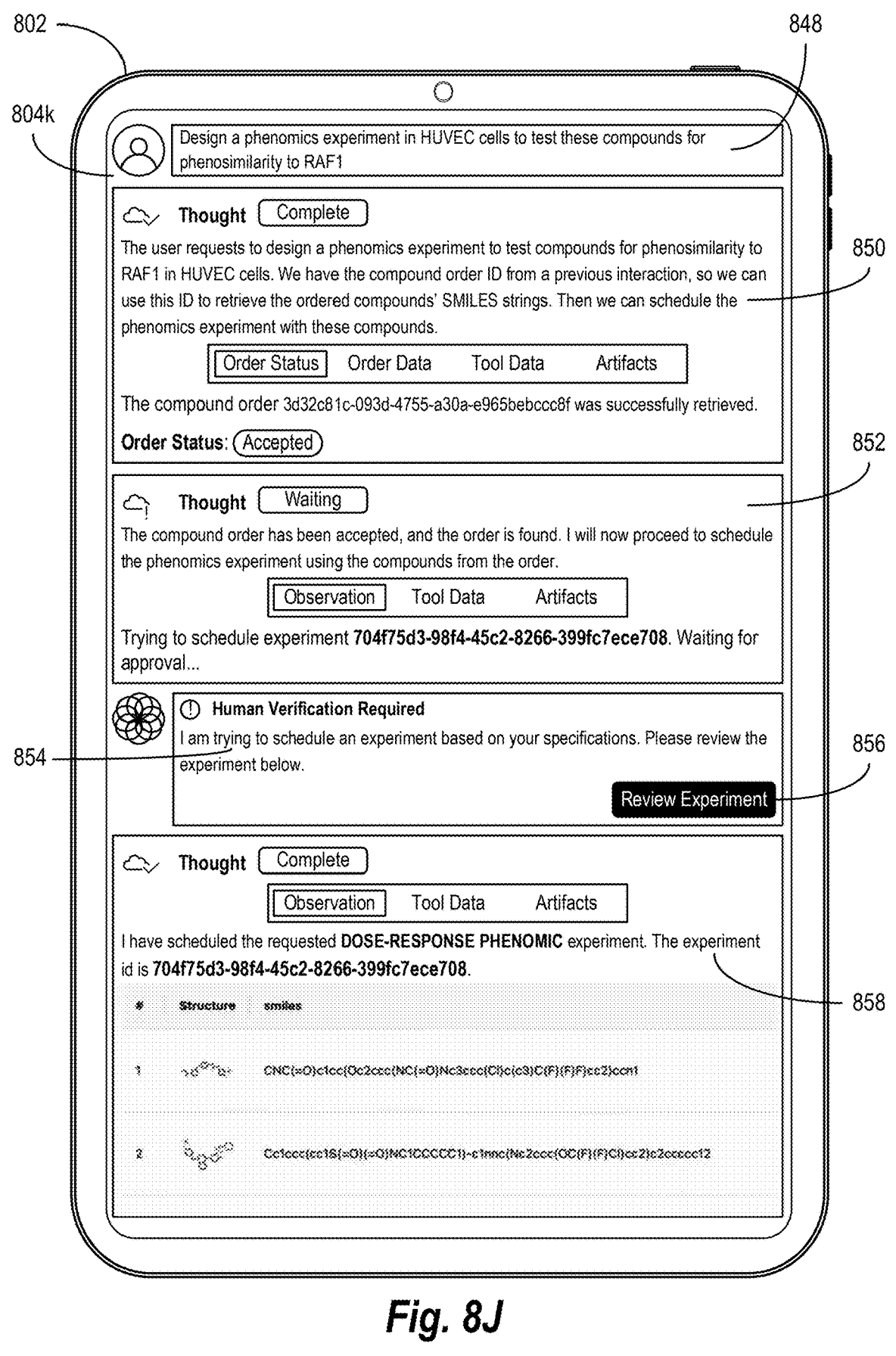

Design a phenomics experiment in HUVEC cells to test these compounds for phenosimilarity to RAF1

Thought ┌ Complete ┐

The user requests to design a phenomics experiment to test compounds for phenosimilarity to RAF1 in HUVEC cells. We have the compound order ID from a previous interaction, so we can use this ID to retrieve the ordered compounds' SMILES strings. Then we can schedule the phenomics experiment with these compounds.

| Order Status | Order Data | Tool Data | Artifacts |
|---|---|---|---|

850

The compound order 3d32c81c-093d-4755-a30a-e965bebccc8f was successfully retrieved.

Order Status: (Accepted)

852

Thought ┌ Waiting ┐

The compound order has been accepted, and the order is found. I will now proceed to schedule the phenomics experiment using the compounds from the order.

| Observation | Tool Data | Artifacts |
|---|---|---|

Trying to schedule experiment 704f75d3-98f4-45c2-8266-399fc7ece708. Waiting for approval...

ⓘ Human Verification Required

I am trying to schedule an experiment based on your specifications. Please review the experiment below.

Review Experiment

854

856

Thought ┌ Complete ┐

| Observation | Tool Data | Artifacts |
|---|---|---|

I have scheduled the requested DOSE-RESPONSE PHENOMIC experiment. The experiment id is 704f75d3-98f4-45c2-8266-399fc7ece708.

858

| # | Structure | smiles |
|---|---|---|
| 1 | | CNC(=O)c1cc(Oc2ccc(NC(=O)Nc3ccc(Cl)c(c3)C(F)(F)F)cc2)ccn1 |
| 2 | | Cc1ccc(cc1S(=O)(=O)NC1CCCCC1)-c1nnc(Nc2ccc(OC(F)(F)Cl)cc2)c2ccccc12 |

Figure 8K:
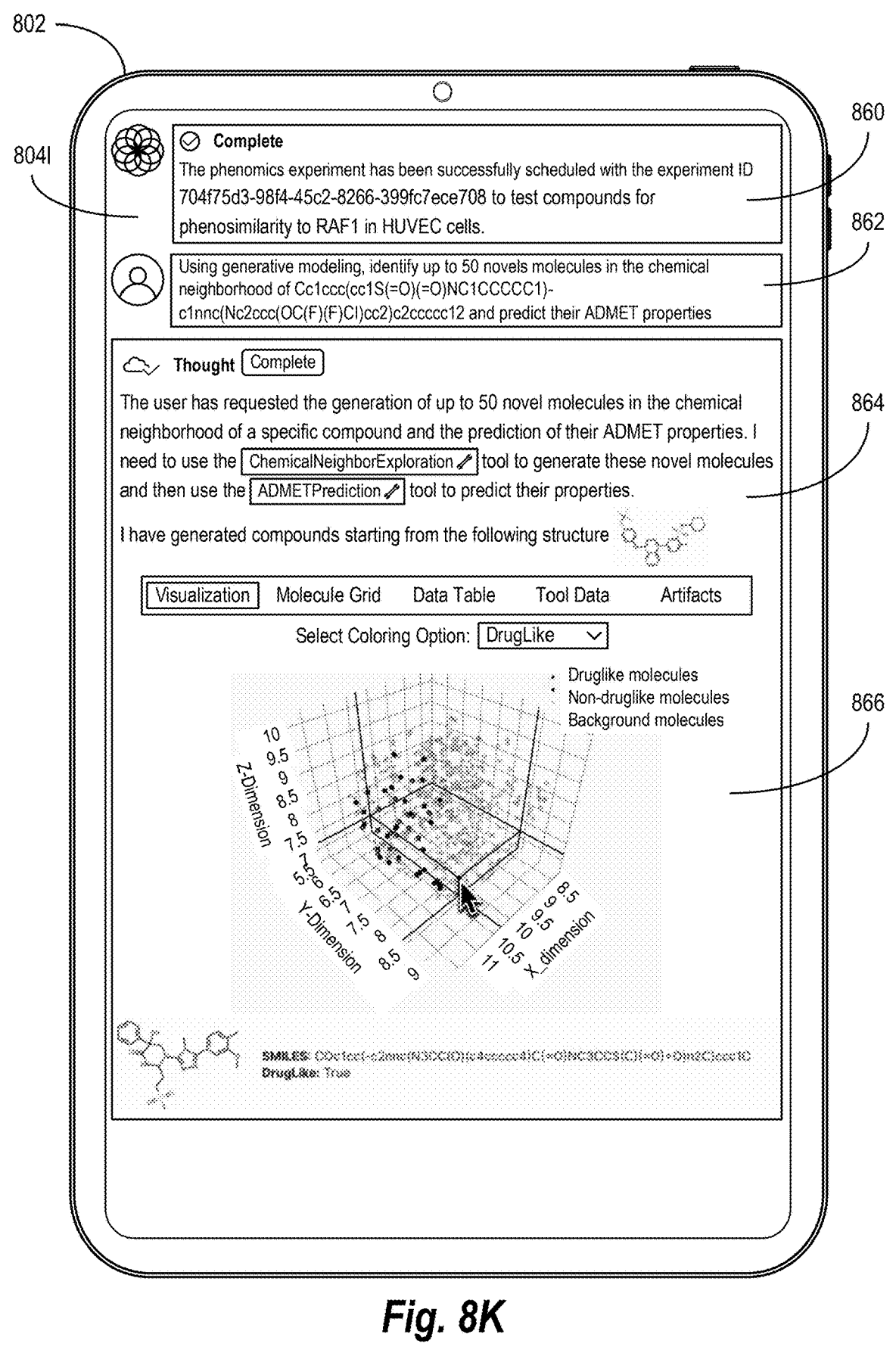

⊘ Complete

The phenomics experiment has been successfully scheduled with the experiment ID 704f75d3-98f4-45c2-8266-399fc7ece708 to test compounds for phenosimilarity to RAF1 in HUVEC cells.

Using generative modeling, identify up to 50 novels molecules in the chemical neighborhood of Cc1ccc(cc1S(=O)(=O)NC1CCCCC1)-c1nnc(Nc2ccc(OC(F)(F)Cl)cc2)c2ccccc12 and predict their ADMET properties

☁ Thought [Complete]

The user has requested the generation of up to 50 novel molecules in the chemical neighborhood of a specific compound and the prediction of their ADMET properties. I need to use the [ ChemicalNeighborExploration ✏ ] tool to generate these novel molecules and then use the [ ADMETPrediction ✏ ] tool to predict their properties.

I have generated compounds starting from the following structure

| Visualization | Molecule Grid | Data Table | Tool Data | Artifacts |

Select Coloring Option: [ DrugLike ▽ ]

• Druglike molecules
• Non-druglike molecules
  Background molecules

SMILES: COc1ccc(-c2nnc(N3CC(O)c4ccccc4Cl)c4nc3ccs(Cl)c4)cc3)nc3ccc1O
DrugLike: True

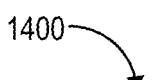
1400
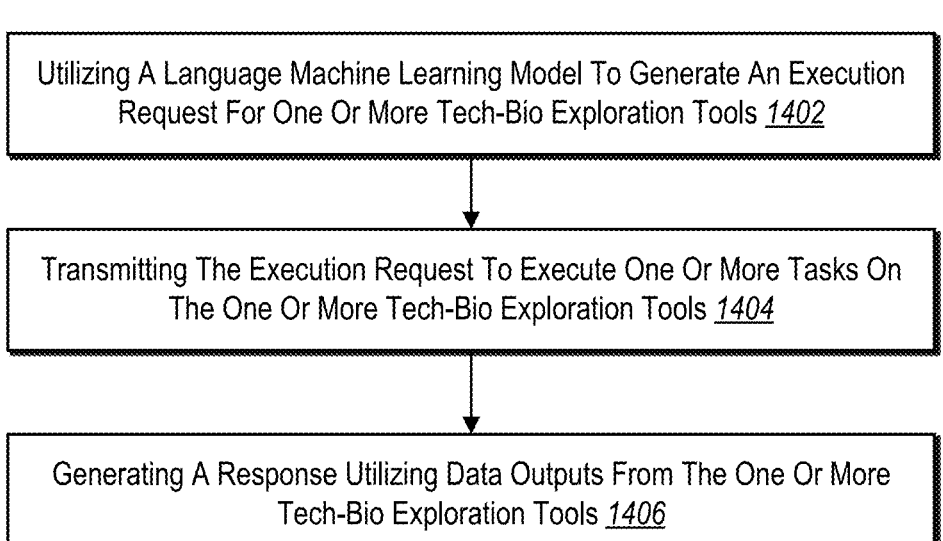
Utilizing A Language Machine Learning Model To Generate An Execution Request For One Or More Tech-Bio Exploration Tools *1402*
Transmitting The Execution Request To Execute One Or More Tasks On The One Or More Tech-Bio Exploration Tools *1404*
Generating A Response Utilizing Data Outputs From The One Or More Tech-Bio Exploration Tools *1406*
*Fig. 14*

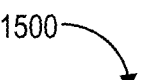

1500

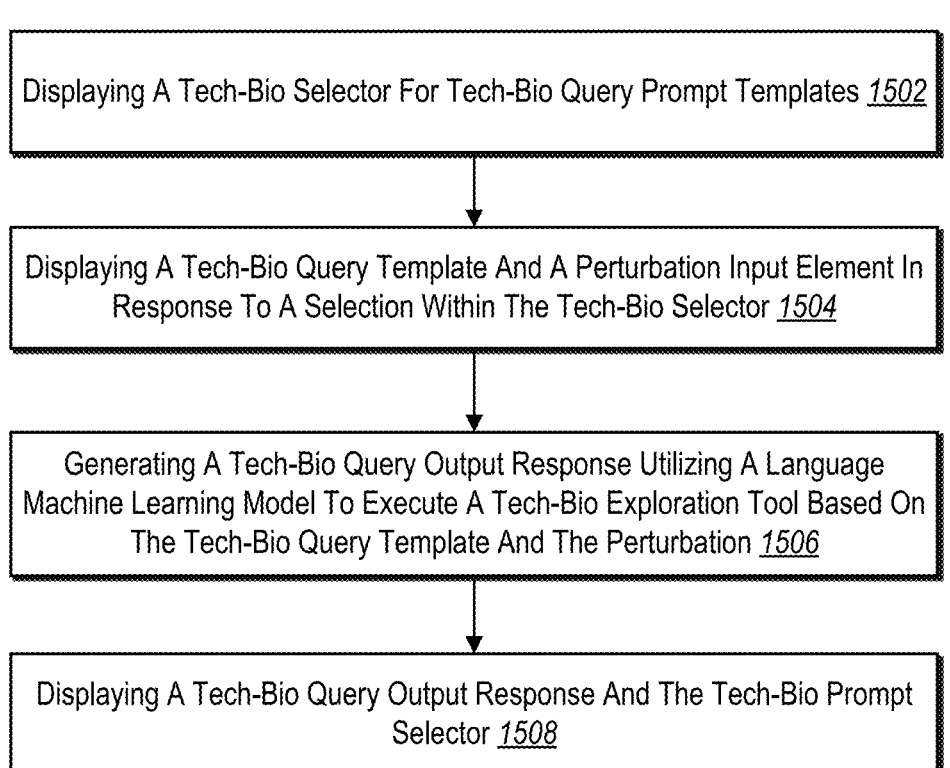

Displaying A Tech-Bio Selector For Tech-Bio Query Prompt Templates *1502*

Displaying A Tech-Bio Query Template And A Perturbation Input Element In Response To A Selection Within The Tech-Bio Selector *1504*

Generating A Tech-Bio Query Output Response Utilizing A Language Machine Learning Model To Execute A Tech-Bio Exploration Tool Based On The Tech-Bio Query Template And The Perturbation *1506*

Displaying A Tech-Bio Query Output Response And The Tech-Bio Prompt Selector *1508*

*Fig. 15*

UTILIZING LANGUAGE MACHINE LEARNING MODELS FOR AUTONOMOUS EXECUTIONS OF COMPUTERIZED TECH-BIO EXPLORATION TOOLS

CROSS-REFERENCE TO RELATED APPLICATIONS

This application claims priority to and the benefit of U.S. Provisional Patent Application No. 63/618,172, filed on Jan. 5, 2024, which is incorporated herein by reference in its entirety.

BACKGROUND

Recent years have seen significant developments in platforms that use computing devices to orchestrate biological discovery pipelines to extract and analyze digital signals corresponding to biological relationships. Indeed, oftentimes, existing systems enable computing devices to build and execute a variety of components in an experiment design to extract and analyze digital signals related to biological relationships. For instance, some existing systems enable computing devices to build and execute experiment designs that utilize tools and models to select target genes and/or compounds, analyze relationships in phenotype perturbations, and analyze or record observations. Although some existing systems can facilitate the creation of computerized experiment designs, many existing systems often have a number of technical deficiencies. For instance, many existing systems often cannot easily execute complex biological discovery pipeline workflows, often inefficiently generate biological discovery pipeline workflows, and often result in rigid biological discovery pipelines that are limited by user configurations.

SUMMARY

Embodiments of the present disclosure provide benefits and/or solve one or more of the foregoing or other problems in the art with systems, non-transitory computer-readable media, and computer-implemented methods for utilizing language machine learning models as autonomous reasoners to navigate and execute multiple layers of a computerized bio-activity discovery pipeline of a tech-bio exploration system. In particular, the disclosed systems can utilize a language machine learning model that learns to access one or more tech-bio exploration tools of a tech-bio exploration system to execute one or more processes and/or tasks in a bio-activity discovery pipeline. Indeed, the disclosed systems can utilize the language machine learning model to learn and autonomously execute various tech-bio exploration tools to perform tasks, such as, but not limited to, determining target compounds, generating perturbation images, determining relationships between compounds and genes (or other cellular structures), identifying compound starting points, identifying gene targets, and/or identifying compound compatibilities.

In some implementations, the disclosed systems can provide an interactive query prompt interface to enable users to provide tech-bio queries (as prompts) and, in turn, utilize the language machine learning model with the prompts to execute one or more processes and/or tasks in the bio-activity discovery pipeline to generate and/or retrieve data (as a response) relevant to the tech-bio query prompt. For example, the disclosed systems can provide an interactive query prompt interface with a tech-bio prompt selector having tech-bio query prompt templates. Indeed, the disclosed systems can further utilize a large language machine learning model with a selected tech-bio query prompt template and an input perturbation for the template to execute one or more tech-bio exploration tools (for performance of one or more tech-bio tasks) to determine and display a tech-bio query output response. In some cases, the disclosed systems can receive a free-form (e.g., open ended) tech-bio query and utilize the language machine learning model to generate and transmit an execution request to one or more tech-bio exploration tools to generate a response for the free-form (e.g., open ended) tech-bio query. Indeed, the disclosed systems can utilize the language machine learning model with the prompts to generate and display language machine learning model thought outputs indicating an approach or workflow that will be executed by the language machine learning model for the tech-bio queries, execute one or more processes and/or tasks in the bio-activity discovery pipeline to generate and/or retrieve data (as a response) relevant to the tech-bio query prompt, and/or generate and display a response (or final output) for the tech-bio query prompt.

Moreover, in some embodiments, the disclosed systems can utilize one or more language machine learning models to autonomously utilize and/or interact with one or more tech-bio tools in the bio-activity discovery pipeline to generate and/or obtain data related to various biological relationships identified from execution of tools in the bio-activity discovery pipeline.

Additional features and advantages of one or more embodiments of the present disclosure are outlined in the description which follows, and in part can be determined from the description, or may be learned by the practice of such example embodiments.

BRIEF DESCRIPTION OF THE DRAWINGS

The detailed description is described with reference to the accompanying drawings in which:

FIGS. 6A-6C illustrate an AI tech-bio system utilizing tech-bio query prompt template selection with a language machine learning model to execute one or more tech-bio exploration tool in accordance with one or more embodiments.

FIGS. 7A-7G illustrate an example workflow of an AI tech-bio system providing an interactive query prompt interface with a tech-bio prompt selector to execute tech-bio exploration tools for a tech-bio query output response in accordance with one or more embodiments.

FIGS. 8A-8L illustrate an example workflow of an AI tech-bio system utilizing free-form text tech-bio query prompts to execute tech-bio exploration tools for a tech-bio query output response in accordance with one or more embodiments.

FIG. 14 illustrates an example series of acts for utilizing a language machine learning model to execute one or more tech-bio exploration tool tasks in accordance with one or more embodiments.

FIG. 15 illustrates an example series of acts for utilizing a language machine learning model with selectable tech-bio query prompt templates to execute one or more tech-bio exploration tool tasks in accordance with one or more embodiments.

DETAILED DESCRIPTION

Figure 1:
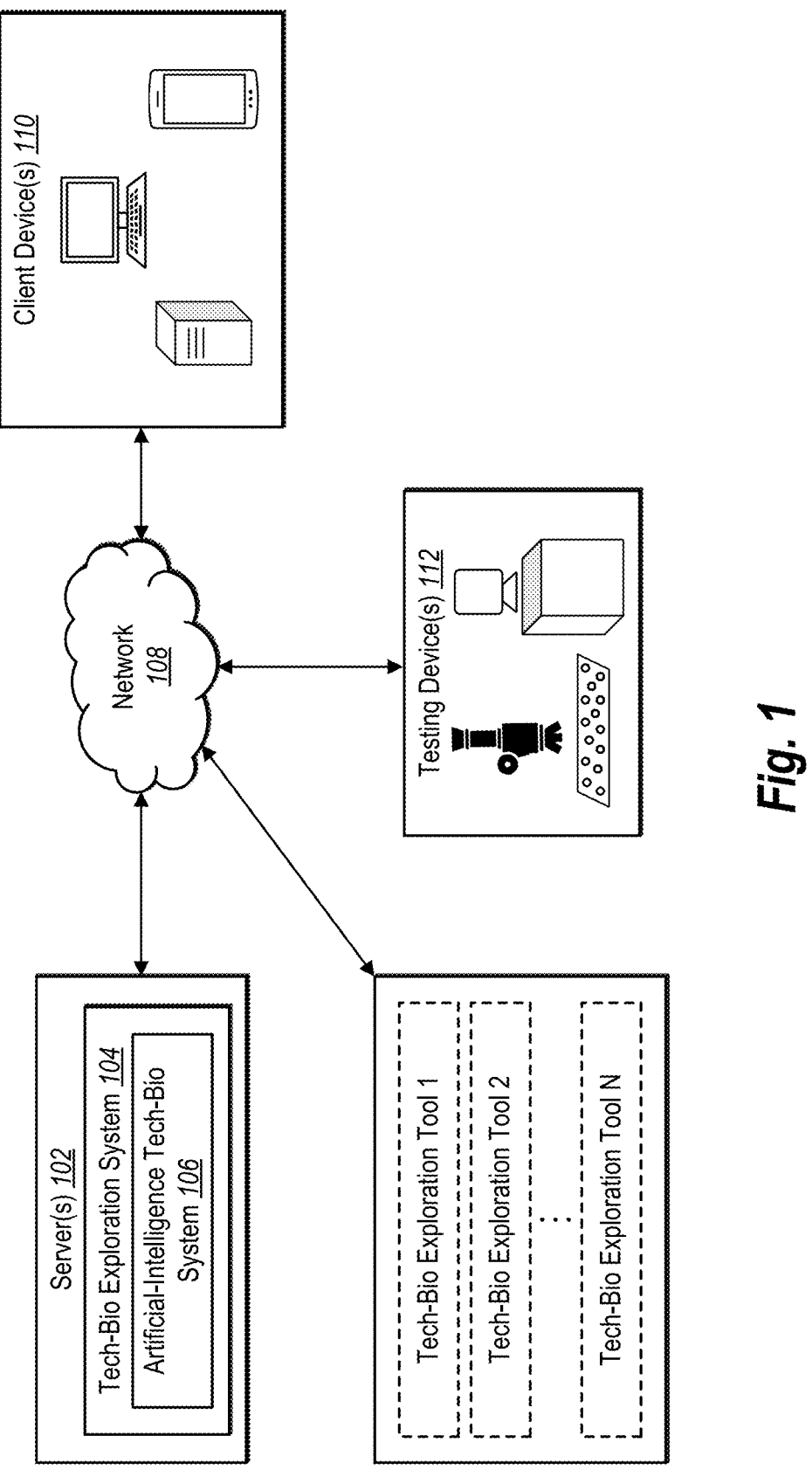
FIG. 1 illustrates a schematic diagram of a system environment in which an AI tech-bio system can operate in accordance with one or more embodiments.

This disclosure describes one or more embodiments of an artificial-intelligent (AI) tech-bio system that utilizes a language machine learning model as an autonomous agent to interact with one or more computerized tech-bio exploration tools within a computerized bio-activity discovery pipeline (or other drug discovery data pipeline) to generate and/or obtain bio-activity data. In particular, the AI tech-bio system can utilize train (or configure) one or more language machine learning models as autonomous agents that learn to interact with (or utilize) one or more tools within a computerized drug discovery pipeline. For instance, the AI tech-bio system can enable an interactive application that facilitates prompt-based tech-bio queries (or requests) that cause the language machine learning model-based autonomous agents to execute one or more tasks (based on an analysis of the prompt-based tech-bio request) within the computerized bio-activity discovery pipeline to generate and/or obtain bio-activity data as a response to the prompt-based tech-bio request. Moreover, in some instances, the AI tech-bio system can also utilize the language machine learning model-based autonomous agents to automatically execute various combinations of tasks within the computerized bio-activity discovery pipeline to identify and/or generate various bio-activity data and/or insights within a tech-bio exploration system ecosystem (e.g., compound identification, gene and compound relationship identification, protein of interest identification, compound program recommendations, perturbation image generation, perturbation heatmap generation, mechanism-of-action data).

Indeed, in one or more implementations, the AI tech-bio system can utilize language machine learning models as advanced reasoners to navigate different data layers within a tech-bio system or pipeline, extract actionable information, and execute one or more processes within the tech-bio system (e.g., via tech-bio exploration tools) to determine one or more bio-activity relationships or discoveries. In some implementations, the AI tech-bio system displays fillable and/or adjustable tech-bio queries via tech-bio prompt selectors having tech-bio query prompt templates and/or enables free-form text tech-bio queries for the language machine learning models.

In particular, the AI tech-bio system can operate within a computerized bio-activity discovery pipeline (or other drug discovery data pipeline) of a tech-bio exploration system. As part of the computerized bio-activity discovery pipeline, the AI tech-bio system can navigate data within the tech-bio exploration system (and/or a user provided prompt), extract actionable information from the data (or prompt), and then execute one or more processes (e.g., tech-bio exploration tools in the computerized bio-activity discovery pipeline). For instance, the AI tech-bio system can execute one or more processes (via tech-bio exploration tools) to perform tasks, such as, but not limited to, determining novel chemical and/or biological relationships, generating visualizations of compounds, biological relationships, and/or phenomic perturbations (e.g., perturbation heatmaps), identifying active compounds in biological relationships, identifying absorption, distribution, metabolism, excretion, and/or toxicity (ADMET) properties and/or drug-likeness matches, and/or interfacing with one or more third-party autonomous lab tools. Indeed, the AI tech-bio system can execute such processes to obtain and/or generate a bio-activity related response to a bio-activity query and/or bio-activity data (e.g., compounds of interest, phenomic perturbation heatmaps, biological relationships between genes, proteins, and/or compounds) for ingestion in the tech-bio exploration system.

In some implementations, the AI tech-bio system causes a language machine learning model to learn attributes of a tech-bio exploration tool such that the language machine learning model can autonomously execute and/or utilize the tech-bio exploration tool. For instance, the AI tech-bio system utilizes a structure (e.g., descriptions, code, application programming interfaces (APIs)) of a tech-bio exploration tool with the language machine learning model to learn the attributes of the tech-bio exploration tool. In some cases, the AI tech-bio system utilizes single shot (or few shot) learning approach to teach (or train) the language machine learning model to understand and execute a particular tech-bio exploration tool by causing the language machine learning model to read (or ingest) the structure (e.g., descriptions, code, application programming interfaces (APIs)) of the particular tech-bio exploration tool. Indeed, based on the language machine learning model learning the attributes of the tech-bio exploration tools, the AI tech-bio system can utilize the language machine learning model as an autonomous reasoner that navigates the various tech-bio exploration tools and/or bio-activity data within the bio-activity discovery pipeline to automatically respond to queries and/or automatically generate additional bio-activity data (in accordance with one or more implementations herein).

In some instances, the AI tech-bio system can provide an interactive query prompt interface to enable users to provide tech-bio queries (as prompts) and, in turn, utilize the language machine learning model to respond to the tech-bio queries with bio-activity data. For instance, the AI tech-bio system can receive a tech-bio query (e.g., as a prompt). Furthermore, the AI tech-bio system can utilize the language machine learning model to analyze the prompt and generate a set of execution requests for the one or more tech-bio exploration tools that cause the tech-bio exploration tools to perform tasks to accomplish the tech-bio query from the prompt. Indeed, the AI tech-bio system can generate one or more execution requests (e.g., tool specific code or API calls from an extended, modified prompt) that includes tasks or steps to execute within the tech-bio exploration tools to obtain and/or generate bio-activity data as a response to the input query prompt.

In particular, to generate the execution requests, the AI tech-bio system 106 can receive a query prompt (a free-form text prompt and/or a template-based prompt with fillable variables). Moreover, the AI tech-bio system 106 can generate a modified (contextual) prompt by appending information for one or more tool structures (e.g., descriptions, API call formatting instructions) for tech-bio tools to the query prompt. Then, the AI tech-bio system 106 can provide the modified prompt (e.g., the user provided free-form text prompt and/or template-based prompt) with the appended information of the one or more tool structures to the language machine learning model. Furthermore, the language machine learning model can utilize the modified prompt to generate one or more execution requests by determining appropriate tech-bio tools, determining appropriate calls to the tech-bio tools, and/or determining a sequence of tasks to execute via the tech-bio tools to generate and/or obtain bio-activity data for the modified prompt.

Moreover, for the tech-bio query prompt, the AI tech-bio system can utilize the generated set of execution requests to cause (or initiate) the one or more tech-bio exploration tools to generate and/or retrieve bio-activity data. For instance, the AI tech-bio system can utilize a generated set of execution requests to cause a first tech-bio exploration tool to retrieve bio-activity data as input into a second tech-bio exploration tool. Furthermore, the AI tech-bio system can utilize the generated set of execution requests to cause the second tech-bio exploration tool to generate additional bio-activity data from the retrieved bio-activity data. In addition, the AI tech-bio system can utilize the bio-activity data and the additional bio-activity data with the language machine learning model to generate a response for the tech-bio query prompt. For instance, the response can include the retrieved and/or generated bio-activity data and/or visualizations for the retrieved and/or generated bio-activity data.

In some cases, the AI tech-bio system, utilizing the language machine learning model, can generate (and/or display) the execution requests as machine learning thoughts (e.g., describing a workflow to handle or execute the tech-bio query). Indeed, the AI tech-bio system, utilizing the language machine learning model, generates and displays descriptions for the execution requests to provide information (decided by the language learning machine learning model) for the workflow and tech-bio tools utilized to carry out a tech-bio query. In one or more instances, the AI tech-bio system, utilizing the language machine learning model, generates (and/or displays) actions performed or to be performed to execute the tech-bio query. For example, the AI tech-bio system can determine and display a set of actions to enable for tech-bio tools in response to the tech-bio query. Furthermore, the AI tech-bio system, utilizing the language machine learning model, can generate (and/or display) one or more data inputs for a tech-bio tool for the tech-bio query.

Indeed, the AI tech-bio system can utilize the language machine learning model to decide (or determine) between generating various combinations of a thought, action, or input for a tech-bio query (upon receiving the tech-bio query and/or one or more data output from tech-bio tools as part of a workflow for the tech-bio query). In one or more implementations, the AI tech-bio system 106, utilizing the large language machine learning model, can select between generating the response to the tech-bio query or executing one or more additional tech-bio tools from the one or more language model prompts (e.g., after receiving an output from tech-bio tool(s). For instance, the AI tech-bio system 106 can utilize thoughts, actions, or inputs generated via the language machine learning model to select between generating the response to the tech-bio query or executing one or more additional tech-bio tools.

Additionally, the AI tech-bio system can include an evaluation model that analyzes input (or other data) generated from the language machine learning model to determine if the language machine learning model is identifying appropriate tech-bio tools and accurate instructions for the tech-bio tools). Moreover, the AI tech-bio system can analyze the instructions generated by the language machine learning model (e.g., input key-value pairs in an API for a tech-bio tool, a workflow), execute the instructions at the varying tech-bio tools, and/or return (or retrieve) observations (or outputs) of the tech-bio tools based on the executed instructions. Moreover, the AI tech-bio system can utilize the language machine learning model with the returned (or retrieved) observations (or outputs) of the tech-bio tools to generate a response for the tech-bio query.

Moreover, in some cases, the AI tech-bio system, utilizing the language machine learning model, can determine that a data output from a particular tech-bio tool completes (or resolves) the tech-bio query and can generate a response based on the data output as a final response to the tech-bio query. For example, the AI tech-bio system can parse an output or observation from a tech-bio tool in context to the original tech-bio query and generate a text response to the query. Additionally, the AI tech-bio system (via the utilization of the language machine learning model) can generate a response to the tech-bio query with information provided directly from one or more individual tech-bio tools (e.g., artifacts for data lists or CSV files). In one or more implementations, the AI tech-bio system 106 can utilize the language machine learning model to generate a response (e.g., reasoning or an overview of a process workflow utilized by the language machine learning model, such as tech-bio tool selection) separate from data of the tech-bio tools to increase fluidity of the interactions with the AI tech-bio system 106. Moreover, in some cases, the AI tech-bio system 106 can also generate a response without passing the artifact through the language machine learning model (e.g., to improve efficiency). In some instances, the AI tech-bio system can utilize the language machine learning model to parse an output or observation from a tech-bio tool, determine that additional reasoning steps exist to answer (or respond to the tech-bio query), and perform an additional thought, action, or input step for the tech-bio query.

Indeed, the AI tech-bio system can provide, for display within an interactive graphical user interface, a practical application that facilitates users to provide tech-bio relevant queries (e.g., as text prompts, voice input prompts). Based on receiving a tech-bio relevant query within the interactive graphical user interface, the AI tech-bio system can generate and/or retrieve bio-activity data for the query prompt by utilizing a language machine learning model with one or more tech-bio exploration tools (in accordance with one or more implementations). Furthermore, the AI tech-bio system can provide, for display within the interactive graphical user interface, a response (generated by the language machine learning model) to the tech-bio relevant query through the generated and/or retrieved bio-activity data from (autonomous) execution of the various tech-bio exploration tools.

As an example, the AI tech-bio system can receive a tech-bio query (e.g., a text prompt with a query for a novel chemical starting point, a novel gene, a target for a particular disease, compounds with similar structures as particular compounds). To further the example, the AI tech-bio system can utilize the language machine learning model to analyze the tech-bio query and generate execution requests for various tech-bio exploration tools (e.g., by appending contextual information for the tools to the text prompt or generating particular API calls for the tools) to cause the tech-bio exploration tools to accomplish a task identified in the query by generating and/or obtaining bio-activity data (e.g., identifying a chemical starting point, identifying a novel gene, identifying a target for a particular disease, identifying compounds with similar structures to a particular compound). Moreover, the AI tech-bio system can utilize the generated and/or obtained bio-activity data from the tech-bio exploration tools with the language machine learning model to generate a response for the tech-bio query (e.g., for display within an interactive graphical user interface).

In one or more implementations, the AI tech-bio system can receive a selection of a tech-bio query prompt template and an input perturbation to generate a set of prompts (e.g., prompts for the specific tech-bio query template, role framing prompts, tech-bio tool structure descriptors). Moreover, the AI tech-bio system can utilize a language machine learning model with the set of prompts to generate execution requests for one or more tech-bio tools to perform tasks for the selected tech-bio query. Furthermore, the AI tech-bio system can execute one or more tech-bio tools to generate outputs towards (or in relation to) the tech-bio query. In some instances, the AI tech-bio system can generate results or outputs for the tech-bio query and display the via tech-bio prompt selector to enable users to select additional tech-bio query prompt templates (e.g., for an additional tech-bio query and/or for tech-bio queries stemming from or building on the results or outputs of the previous tech-bio query). In some implementations, the AI tech-bio system utilizes the language learning machine learning model with the tech-bio query prompt templates to enable a workflow within the computerized bio-activity discovery pipeline that generates outputs (or results) that build from one or more selected tech-bio query prompt templates (e.g., identifying compounds with threshold activity scores for a perturbation, followed by identifying matched molecular pair series for the compounds, followed by clustering the compounds by phenomics, followed by determining mechanisms-of-action for one or more of the compounds).

In some instances, the AI tech-bio system can receive a free-form text tech-bio query prompt. Moreover, the AI tech-bio system can utilize a large language machine learning model to analyze the free-form text tech-bio query and generate a set of prompts (e.g., prompts that format the free-form text tech-bio query prompt as specific input, role framing prompts, tech-bio tool structure descriptors). Furthermore, the AI tech-bio system can utilize the language machine learning model with the set of prompts to generate execution requests to cause the one or more tech-bio tools to perform tasks to determine bio-activity data and/or insights for the free-form text tech-bio query prompt. In one or more instances, the AI tech-bio system can receive multiple free-form text tech-bio queries that utilize the language machine learning model to build a workflow within the computerized bio-activity discovery pipeline that generates bio-activity outputs (or results). As an example of a particular workflow, the AI tech-bio system can receive, from a client device, multiple text prompts (as part of a workflow) requesting a list of targets for a mechanism-of-action, targets with similar phenoprints (from the list of targets) using mappings of biology from a tech-bio exploration system, requesting identification of active, soluble compounds for a particular output target, requesting the generation or identification of properties for the compounds, requesting an automated ordering (or purchasing) of particular compounds, and requesting an initiation of automated wet lab experiments for the particular compounds.

In some implementations, the AI tech-bio system utilizes the language machine learning model-based as an autonomous agent to automatically execute various combinations of tasks within the computerized bio-activity discovery pipeline to identify and/or generate various bio-activity data and/or insights within a tech-bio exploration system ecosystem. For instance, the AI tech-bio system can utilize the language machine learning model with various bio-activity data available within the tech-bio exploration system (e.g., identified compounds, gene and compound relationships, identified proteins of interest, generated compound program recommendations, perturbation images, generated perturbation heatmaps) to identify actionable information. Moreover, the AI tech-bio system can utilize the actionable information (e.g., a query, a hypothesis) to generate (or orchestrate) a set of executable tasks (e.g., an experiment design) to execute within the bio-activity discovery pipeline.

In addition, the AI tech-bio system can utilize the language machine learning model to generate a set of tool execution requests for one or more tech-bio exploration tools within the bio-activity discovery pipeline. Subsequently, the AI tech-bio system, automatically, utilizes the set of tool execution requests with the one or more tech-bio exploration tools to generate and/or obtain bio-activity data (in accordance with one or more embodiments herein). In addition, the AI tech-bio system further utilizes the language machine learning model to generate insights (e.g., biological relationships, novel compounds, matches between compounds and/or target diseases, perturbation heat maps, visualizations) from the generated and/or obtained bio-activity data. Furthermore, the AI tech-bio system can automatically generate the above-mentioned insights and provide (e.g., transmit, display, message) the bio-activity data (or bio-activity data insights) within a client device.

In some implementations, the AI tech-bio system can utilize language machine learning models to operate autonomously by assigning different language machine learning models to different tasks (or tech-bio exploration tools) that transmit (or feed) information and/or prompts between the different language machine learning models to autonomously generate and/or obtain bio-activity data. For instance, the AI tech-bio system can assign a language machine learning model to individual tech-bio exploration tools to enable the language machine learning model to understand and operate the individual tech-bio exploration tool. Then, the AI tech-bio system can enable various language machine learning models to identify, generate, retrieve, and transmit bio-activity data from the one or more tech-bio exploration tools to other language machine learning models to accomplish various tasks in a bio-activity discovery pipeline.

To illustrate, in some cases, the AI tech-bio system can utilize communications between the language machine learning models that interact with the various tech-bio exploration tools to automatically generate and/or identify various bio-activity data. For example, the communicating autonomous language machine learning models can generate bio-activity data, such as, but not limited to, compounds, genes, or proteins of interest, hypotheses, assay initiations, and/or program recommendations. In some cases, the AI tech-bio system can build a repository of bio-activity data by storing the bio-activity data identified and/or generated by the one or more language machine learning models.

As mentioned above, although existing can facilitate the creation of computerized experiment designs, such systems often have a number of problems in relation to case-of-use, efficiency, and flexibility. For instance, many conventional systems facilitate biological discovery pipelines to orchestrate computerized experiment designs and/or retrieve bio-activity data that require user selection of tools and/or configurations for the tools to execute the computerized experiment designs and/or to retrieve specific bio-activity data. However, a computerized biological discovery pipeline can utilize various tools and models for genes and/or compounds, relationships, and recorded observations with millions of combinations. Indeed, because of the substantial number of combinations that can be utilized in a computerized biological discover pipeline, existing systems often facilitate time consuming and difficult to utilize systems that require an inefficient and slow user selection and configuration process to execute tools and/or computerized experiment designs for tech-bio queries. In many instances, conventional systems often inefficiently utilize computational resources and time to navigate between multiple interfaces to facilitate user creation and/or selection of tools and tool configurations for a computerized experiment design.

In addition, due to a reliance on user defined and/or user configured processes for tools in a computerized experiment design, many conventional systems are rigid. For instance, many conventional systems are limited to executing tech-bio queries utilizing user configured processes that do not account for a substantial number of possibilities via various tools available within a computerized biological discovery pipeline (e.g., millions of combinations between gene selections, compound selections, mapped relationships). Accordingly, conventional systems often result in rigid executions that rely on user created experiment designs and/or experiment design tool configurations.

Furthermore, conventional systems often utilize multiple machine learning models within a computerized biological discovery pipeline. Oftentimes, such conventional systems are difficult to utilize without expert knowledge for the variety of machine learning models utilized. Indeed, existing systems often do not provide an easy to use approach to generate and/or obtain data for a bio-related query from a computerized biological discovery pipeline that requires operability of various machine learning models for the retrieval and/or creation of data for a bio-related query.

In addition, due to the slow manual configuration and inflexibility to orchestrate computerized experiment designs and/or bio-related query retrieval tasks, existing systems are often inaccurate. Indeed, due to the above-mentioned limitations, many conventional systems are limited in the number of iterations and/or executions performed on different combinations of biological properties (e.g., different genes, compounds). Due to the limitation in iterations, conventional systems are often inaccurate and/or have a limited knowledge base.

As suggested by the foregoing, the AI tech-bio system provides a variety of technical advantages relative to conventional systems. For instance, the AI tech-bio system improves speed and efficiency in computerized bio-activity discovery pipelines. For instance, the AI tech-bio system creates a practical application that facilitates query requests to cause automated agents (via language machine learning models) to orchestrate various tools and/or processes in a bio-activity discovery pipeline. In particular, the AI tech-bio system enables querying through and/or performing computerized tests and observations of millions of combinations of bio-activity data with limited human intervention. As a result, the AI tech-bio system can enable a quick process that enables client devices to query a large knowledge base of tech-bio tools and bio-activity data to retrieve data for various combinations of questions, automatically perform actions to identify novel information, and/or to perform complex actions within the pipeline with limited user intervention. Indeed, in some cases, the AI tech-bio system enables a client device to query a complex knowledge base of the bio-activity discovery pipeline with simplified query prompts (e.g., to automatically execute tasks on multiple tech-bio tools to answer the simplified query) via language machine learning models. Indeed, the AI tech-bio system enables an interface to quickly query (or command an action) within the bio-activity discovery pipeline with reduced user navigation and reduced utilization of computational resources (from inefficient user navigation).

In addition, the AI tech-bio system utilizes a language machine learning model that is not limited to user defined and/or configured processes within a network of tech-bio tools. For instance, the AI tech-bio system utilizes a language machine learning model that automatically learns and utilizes multiple tech-bio tools to test for (and/or query) for bio-activity data from the tech-bio tools. Indeed, the language machine learning model can determine and utilize a substantial number of tech-bio tools and/or combinations of tech-bio tools in response to a simplified query from a client device. Accordingly, the AI tech-bio system can flexibly query, test, and/or utilize various tech-bio exploration tools within a tech-bio exploration system in response to easy-to-use prompts (or commands) and/or autonomously.

In addition, many tech-bio exploration tools include machine learning model components that in conventional systems are difficult to access. Unlike such systems, the language machine learning model of the AI tech-bio system can learn to interface with the language machine learning model components such that users can flexibly input queries that utilize the language machine learning model components without understanding how to operate (or directly interacting with) the language machine learning models.

Additionally, due to the highly automated orchestration of the AI tech-bio system and the flexibility in creating and testing millions of combinations of possible processes with tech-bio exploration tools, the AI tech-bio system increases the accuracy of bio-activity data available in a bio-activity discovery pipeline. In particular, the AI tech-bio system can autonomously operate a large number of iterations and/or executions to generate and/or obtain bio-activity data via utilization of tech-bio exploration tools that are not limited by user configuration. Accordingly, the AI tech-bio system can increase the amount of data available in a bio-activity discovery pipeline-and-the accuracy of bio-activity data presented in response to a query from a client device.

Additional detail regarding an artificial-intelligence (AI) tech-bio system 106 will now be provided with reference to the figures. In particular, FIG. 1 illustrates a schematic diagram of a system environment in which the AI tech-bio 106 can operate in accordance with one or more embodiments.

As shown in FIG. 1, the environment includes server(s) 102 (which includes a tech-bio exploration system 104 and the AI tech-bio system 106), a network 108, client device(s) 110, testing device(s) 112, and tech-bio exploration tools 1-N. As further illustrated in FIG. 1, the various computing devices within the environment can communicate via the network 108. Although FIG. 1 illustrates the AI tech-bio system 106 being implemented by a particular component and/or device within the environment, the AI tech-bio system 106 can be implemented, in whole or in part, by other computing devices and/or components in the environment (e.g., the client device(s) 110). Additional description regarding the illustrated computing devices is provided with respect to FIG. 16 below.

As shown in FIG. 1, the server(s) 102 can include the tech-bio exploration system 104. In some embodiments, the tech-bio exploration system 104 can determine, store, generate, and/or display tech-bio information including maps of biology, biology (or chemistry) experiments from various sources, and/or machine learning tech-bio predictions. For instance, the tech-bio exploration system 104 can analyze data signals corresponding to various treatments or interventions (e.g., compounds or biologics) and the corresponding relationships in genetics, protenomics, phenomics (i.e., cellular phenotypes), invivomics (e.g., expressions or results within a living animal), and/or transcriptomics. In one or more embodiments, the server(s) 102 comprises a data server. In some implementations, the server(s) 102 comprises a communication server or a web-hosting server.

For instance, the tech-bio exploration system 104 can generate and access experimental results corresponding to gene sequences, protein shapes/folding, protein/compound interactions, phenotypes resulting from various interventions or perturbations (e.g., gene knockout sequences or compound treatments), and/or invivo experimentation on various treatments in living animals. By analyzing these signals (e.g., utilizing various machine learning models), the tech-bio exploration system 104 can generate or determine a variety of predictions and inter-relationships for improving treatments/interventions.

To illustrate, the tech-bio exploration system 104 can generate maps of biology indicating biological inter-relationships or similarities between these various input signals to discover potential new treatments. For example, the tech-bio exploration system 104 can utilize machine learning and/or maps of biology to identify a similarity between a first gene associated with disease treatment and a second gene previously unassociated with the disease based on a similarity in resulting phenotypes from gene knockout experiments. The tech-bio exploration system 104 can then identify new treatments based on the gene similarity (e.g., by targeting compounds that impact the second gene). Similarly, the tech-bio exploration system 104 can analyze signals from a variety of sources (e.g., protein interactions, or invivo experiments) to predict efficacious treatments based on various levels of biological data.

Although one or more implementations herein describe the AI tech-bio system utilizing bio-activity data and/or a bio-activity data discovery pipeline with the various language machine learning models, tech-bio exploration tools, and/or as inputs and/or outputs to various components of the AI tech-bio system, the AI tech-bio system can utilize a variety of drug discovery data (in accordance with one or more implementations herein). For example, the AI tech-bio system can utilize drug discovery data, such as, but not limited to, chemistry data, biological data, gene data, and/or protein data. In addition, the AI tech-bio system can utilize, as drug discovery data, drug discovery predictive property data, such as, but not limited to, predictions and/or inferences from clinical data, human dose tolerance prediction data, and/or drug metabolism and pharmacokinetics (DMPK) studies data. Indeed, the AI tech-bio system can utilize various combinations of the above mentioned drug discovery data with the various language machine learning models, tech-bio exploration tools, and/or as inputs and/or outputs to various components of the AI tech-bio system in accordance with one or more implementations herein. Furthermore, the AI tech-bio system can utilize a variety of tech-bio exploration tools (e.g., via API calls or external third party API calls) that generate and/or analyze the various types of drug discovery data (as part of a drug discovery data pipeline) in accordance with one or more implementations herein.

For example, the tech-bio exploration system 104 can generate, manage, store, and/or obtain phenomics data. In one or more instances, phenomics data includes data that indicates or represents one or more characteristics of a cell obtained through microscopic instruments (e.g., a microscope, gene testing device). For example, the tech-bio exploration system 104 can generate and/or utilize phenomics data through phenomic images. In particular, a phenomic image can include a digital image portraying a cell (e.g., a cell after applying a perturbation). For example, a phenomic image includes a digital image of a stem cell after application of a perturbation and further development of the cell. Indeed, a phenomic image can include pixels that portray a modified cell phenotype resulting from a particular cell perturbation (of a perturbation). In addition, phenomics data can include feature space embeddings (or other latent representations) generated from phenomic images (e.g., by a machine learning model of the tech-bio exploration system 104).

Additionally, as used herein, the term "phenomic image embedding" can include a numerical representation of a phenomic image. For example, a phenomic image embedding includes a vector representation of a phenomic image generated by a machine learning model (e.g., a phenomic image generative and/or encoding model, such as a masked autoencoder generative model, a generative adversarial neural network). Thus, a phenomic image embedding includes a feature vector generated by application of various machine learning (or encoder) layers (at different resolutions/dimensionality). Furthermore, in some implementations, the digital molecular-phenomic embedding system 106 can embed phenomic images into a low dimensional feature space via a generative machine learning model (e.g., a masked autoencoder model or channel-agnostic masked autoencoder model) to generate perturbation image embeddings (or phenomic perturbation autoencoder embeddings).

Furthermore, as used herein, the term "transcriptomics embedding" can include a numerical representation of transcriptomics data. For instance, a transcriptomics embedding can include a vector representation of transcriptomics data generated by a machine learning model. Indeed, a transcriptomics embedding can include a feature vector that represents transcriptomics data in a low dimensional feature space (as an embedding).

Moreover, the tech-bio exploration system 104 can generate, manage, store, and/or obtain transcriptomics data. For example, transcriptomics data can include expression data of transcription proteins in a cell. For example, transcriptomics data can include an array or table of ribonucleic acid (RNA) or messenger RNA (mRNA) produced (e.g., an RNA count) in a cell or tissue sample for one or more perturbations. In one or more instances, transcriptomics data can include a collection of RNA transcripts (mRNA) present (e.g., via a count) within a cell or tissue to indicate a snapshot of gene expression under specific conditions. Indeed, the tech-bio exploration system 104 can utilize transcriptomics data to determine gene activity, quantify gene expression, and/or identify changes in gene expression in response to a variety of stimuli (e.g., a perturbation). In addition, transcriptomics data can include feature space embeddings (or other latent representations) generated from transcriptomic arrays or tables of gene counts or samples (e.g., by a machine learning model of the tech-bio exploration system 104).

The tech-bio exploration system 104 can generate GUIs comprising dynamic user interface elements to convey tech-bio information and receive user input for intelligently exploring tech-bio information. Indeed, as mentioned above, the tech-bio exploration system 104 can generate GUIs displaying different maps of biology that intuitively and efficiently express complex interactions between different biological systems for identifying improved treatment solutions. Furthermore, the tech-bio exploration system 104 can also electronically communicate tech-bio information between various computing devices.

As shown in FIG. 1, the tech-bio exploration system 104 can include a system that facilitates various models or algorithms for generating maps of biology (e.g., maps or visualizations illustrating similarities or relationships between genes, proteins, diseases, compounds, and/or treatments) and discovering new treatment options over one or more networks. For example, the tech-bio exploration system 104 collects, manages, and transmits data across a variety of different entities, accounts, and devices. In some cases, the tech-bio exploration system 104 is a network system that facilitates access to (and analysis of) tech-bio information within a centralized operating system. Indeed, the tech-bio exploration system 104 can link data from different network-based research institutions to generate and analyze maps of biology.

Indeed, in some instances, the tech-bio exploration system 104 can include a bio-activity discovery pipeline that facilitates various above-mentioned components of the tech-bio exploration system 104. In some cases, the bio-activity discovery pipeline can include a drug discovery pipeline and/or a biological relationship discovery pipeline. In particular, the tech-bio exploration system 104 can utilize a variety of tech-bio exploration tools (e.g., tech-bio exploration tools 1-N), as part of the bio-activity discovery pipeline, to generate and/or obtain a variety of bio-activity data. Indeed, a bio-activity discovery pipeline can include various automated testing devices, laboratories, and/or tech-bio exploration tools to generate a collection of bio-activity data that explores relationships between cells, compounds, genes, and/or other biological and/or chemical processes.

In one or more implementations, the term "tech-bio exploration tool" (or sometimes referred to as "tech-bio tool") refers to a collection of computer algorithms, instructions, and/or systems that execute a bio-activity data discovery task. In particular, a tech-bio exploration tool can include various systems and/or processes that utilize, analyze, and/or create bio-activity data. For example, the tech-bio exploration system 104 can utilize a variety of tech-bio exploration tools to generate and/or obtain bio-activity data by, but not limited to, determining, storing, generating, and/or displaying tech-bio information, generating and accessing experimental results corresponding to the above-mentioned signals, generating maps of biology indicating biological inter-relationships or similarities between these various input signals to discover potential new treatments, facilitating dynamic user interface elements to convey tech-bio information and receive user input for intelligently exploring tech-bio information, and/or facilitating various models or algorithms for generating maps of biology to discover new treatment options over one or more networks. As an example, a tech-bio exploration tool can generate phenomics data (e.g., phenomic images, phenomic embeddings) and/or compare phenomics data.

As used herein, the term "machine learning model" includes a computer algorithm or a collection of computer algorithms that can be trained and/or tuned based on inputs to approximate unknown functions. For example, a machine learning model can include a computer algorithm with branches, weights, or parameters that changed based on training data to improve for a particular task. Thus, a machine learning model can utilize one or more (deep) learning techniques (e.g., supervised or unsupervised learning) to improve in accuracy and/or effectiveness. Example machine learning models include various types of decision trees, support vector machines, Bayesian networks, random forest models, or neural networks (e.g., deep neural networks, generative adversarial neural networks, convolutional neural networks, recurrent neural networks, large language models, or diffusion neural networks). Similarly, the term "machine learning data" refers to information, data, or files generated or utilized by a machine learning model. Machine learning data can include training data, machine learning parameters, or embeddings/predictions generated by a machine learning model.

As used herein, the term "language machine learning model" refers to a machine learning model that analyzes a language input (e.g., text or verbal input) to generate a predicted output. For instance, a language machine learning model includes a neural network that generates text based on an input text or query. The AI tech-bio system 106 can utilize a variety of architectures for a language machine learning model, such as a large language model or other transformer neural network model. For instance, a large language model includes one or more neural networks capable of processing natural language text to generate outputs that range from predictive outputs, analyses, one or more executable requests for tasks in one or more tech-bio exploration tools, or combinations of data within stored content items. In some cases, the AI tech-bio system 106 can utilize a multi-modal language machine learning model.

In particular, a large language model can include parameters trained (e.g., via deep learning) on large data volumes to learn patterns and rules of language for summarizing and/or generating digital content. Examples of large language model include BLOOM, Bard AI, ChatGPT (e.g., GPT-3, GPT-4, etc.), LaMDA, and/or DialoGPT. Moreover, in some embodiments a language transformer model includes bidirectional encoder representations (BERT), Robustly optimized BERT (RoBERTa), and other text transformer models. Indeed, the AI tech-bio system 106 can utilize a large language model trained to learn patterns and rules defined by tool structures (e.g., descriptions, scope, definitions, code) of one or more tech-bio exploration tools.

As shown in FIG. 1, the tech-bio exploration system 104 can include a system that comprises the AI tech-bio system 106 that utilizes a language machine learning model as an autonomous agent to navigate and execute multiple layers of a computerized bio-activity discovery pipeline of the tech-bio exploration system 104 (via the tech-bio exploration tools 1-N). For instance, the AI tech-bio system 106 can utilize a language machine learning model that learns to access one or more tech-bio exploration tools of a tech-bio exploration system to execute one or more processes and/or tasks in a bio-activity discovery pipeline. As an example, the AI tech-bio system 106 can provide an interactive query prompt interface to enable users to provide tech-bio queries (as prompts) and, in turn, utilize the language machine learning model with the prompts to execute one or more processes and/or tasks through tech-bio exploration tools to generate and/or retrieve bio-activity data relevant to the tech-bio query prompt. In addition, the AI tech-bio system 106 can also utilize one or more language machine learning models to autonomously utilize and/or interact with one or more tech-bio tools in the bio-activity discovery pipeline to generate and/or obtain (new or updated) bio-activity data.

As also illustrated in FIG. 1, the environment includes the client device(s) 110. For example, the client device(s) 110 may include, but is not limited to, a mobile device (e.g., smartphone, tablet) or other type of computing device, including those explained below with reference to FIG. 16. Additionally, the client device(s) 110 can include a computing device associated with (and/or operated by) user accounts for the tech-bio exploration system 104. Moreover, the environment can include various numbers of client devices that communicate and/or interact with the tech-bio exploration system 104 and/or the AI tech-bio system 106.

Furthermore, in one or more implementations, the client device(s) 110 includes a client application. The client application can include instructions that (upon execution) cause the client device(s) 110 to perform various actions. For example, a user of a user account can interact with the client application on the client device(s) 110 to access tech-bio information (e.g., bio-activity data created by the autonomous language machine learning model in accordance with one or more implementations herein), initiate tech-bio request query (e.g., via a text prompt, a voice command prompt), generate graphical user interfaces to display responses from the language machine learning model of the AI tech-bio system 106 for one or more tech-bio queries, and/or generate graphical user interfaces to display bio-activity data that is automatically generated by the autonomous language machine learning model).

As further shown in FIG. 1, the environment includes the network 108. As mentioned above, the network 108 can enable communication between components of the environment. In one or more embodiments, the network 108 may include a suitable network and may communicate using a various number of communication platforms and technologies suitable for transmitting data and/or communication signals, examples of which are described with reference to FIG. 16. Furthermore, although FIG. 1 illustrates computing devices communicating via the network 108, the various components of the environment can communicate and/or interact via other methods (e.g., communicate directly).

In some cases, the AI tech-bio system 106, as part of an experiment design and/or execution of one or more tech-bio exploration tools, generates and accesses machine learning objects, such as results from biological assays. As shown in FIG. 1, the AI tech-bio system 106 can communicate with testing device(s) 112 to obtain and then store this information. For example, the tech-bio exploration system 104 can interact with the testing device(s) 112 that include intelligent robotic devices and camera devices for generating and capturing digital images of cellular phenotypes resulting from different perturbations (e.g., genetic knockouts or compound treatments of stem cells). Similarly, the testing device(s) can include camera devices and/or other sensors (e.g., heat or motion sensors) capturing real-time information from animals as part of invivo experimentation. The tech-bio exploration system 104 can also interact with a variety of other testing device(s) such as devices for determining, generating, or extracting gene sequences or protein information. The experiment design (or experiment components of the experiment design) and/or tech-bio exploration tools can include, but is not limited to, configurations, inputs, outputs, models, and/or settings for the testing device(s) 112.

As mentioned above, the AI tech-bio system 106 can utilize a language machine learning model to enable prompt-based tech-bio queries within a bio-activity discovery pipeline having various tech-bio exploration tools. For instance, FIG. 2 illustrates an exemplary flow of the AI tech-bio system 106 utilizing a language machine learning model to generate bio-activity data for a response to a tech-bio query from a client device by autonomously utilizing one or more tech-bio exploration tools.

Figure 2:
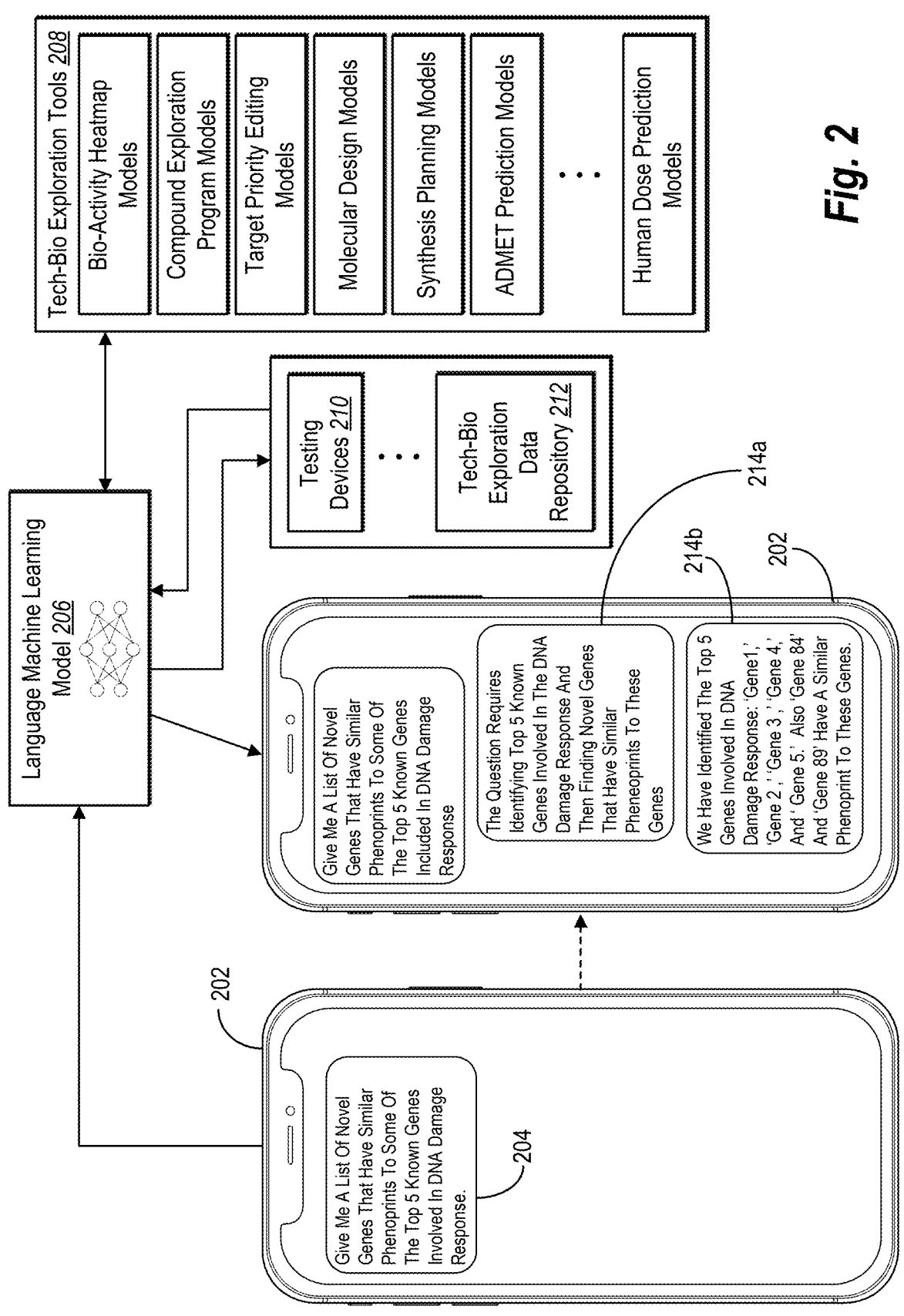
FIG. 2 illustrates an exemplary flow of an AI tech-bio system generating a response to a query in accordance with one or more embodiments.

As shown in FIG. 2, the AI tech-bio system 106 receives a prompt 204 for a tech-bio query within a client device 202 (e.g., as a chat message). As illustrated in FIG. 2, the prompt 204 describes a tech-bio query request (e.g., "give me a list of novel genes that have similar phenoprints to some of the top 5 known genes involved in DNA Damage Response"). Indeed, as shown in FIG. 2, the AI tech-bio system 106 can utilize the prompt 204 with a language machine learning model 206 to analyze the prompt 204. In addition, as shown in FIG. 2, the AI tech-bio system 106 can cause the language machine learning model 206 to interact with the tech-bio exploration tools 208, the testing devices 210, and/or the tech-bio exploration data repository 212 (e.g., a bio-activity discovery pipeline) to generate and/or retrieve bio-activity data for the tech-bio query request of the prompt 204.

In one or more instances, the AI tech-bio system 106 can receive the prompt 204 from a tech-bio prompt selector having tech-bio query prompt templates. Indeed, the AI tech-bio system 106 can receive the prompt 204 from a selection of a tech-bio query prompt template as described below (e.g., in reference to FIGS. 6A-6C and 7A-7G). Moreover, in some cases, the AI tech-bio system 106 can receive the prompt 204 as a free-form text tech-bio query as described below (e.g., in reference to FIGS. 8A-8L).

As used herein, the term "tech-bio query" includes a prompt representing a request for information and/or execution of one or more tasks for a bio-activity discovery pipeline (e.g., to generate and/or obtain data related to various biological relationships identified from execution of tools in the bio-activity discovery pipeline). For example, a tech-bio query can include a prompt/query requesting phenomics data, compound data, perturbation data, and/or transcriptomics data. In some instances, a tech-bio query can include a prompt requesting a comparison and comparison data between phenomics data, compound data, perturbation data, and/or transcriptomics data. Moreover, a tech-bio query can include a prompt requesting the performance of one or more tasks through the bio-activity discovery pipeline, one or more tech-bio exploration tools corresponding to the tech-bio exploration system, and/or one or more third-party systems.

Indeed, as shown in FIG. 2, the AI tech-bio system 106 generate and/or retrieve bio-activity data by executing various tasks for the prompt 204 on the tech-bio exploration tools 208, the testing devices 210, and/or the tech-bio exploration data repository 212 to generate a response 214*a* and a response 214*b* within the client device 202. For instance, as shown in FIG. 2, the AI tech-bio system 106, utilizing the language machine learning model, generates and displays the response 214*a* to demonstrate an understanding of the prompt 204 by the language machine learning model 206 by generating a set of tasks from the prompt 204 (e.g., "the question requires identifying top 5 known genes involved in the DNA damage response and then finding novel genes that have similar phenoprints to these genes").

Furthermore, as shown in FIG. 2, the AI tech-bio system 106 executes the set of tasks illustrated in the response 214*a* (e.g., via execution requests) through the tech-bio exploration tools 208 and/or the testing devices 210 and the tech-bio exploration data repository 212 to generate and/or obtain bio-activity data for the response 214*b*. For instance, the AI tech-bio system 106 can generate and/or receive bio-activity data from the tech-bio exploration tools 208 and/or the testing devices 210 and the tech-bio exploration data repository 212 (for the set of tasks illustrated in the response 214*a*) and utilize the bio-activity data to generate the response 214*b* (e.g., to answer the query in the prompt 204). Indeed, as shown in FIG. 2, the AI tech-bio system 106 displays the response 214*b* (e.g., "we have identified the top 5 genes involved in DNA damage response: 'Gene 1,' 'Gene 2,' 'Gene 3,' 'Gene 4,' and 'Gene 5.' Also, 'gene 84' and 'gene 89' have a similar phenoprint to these genes.").

As used herein, the term "execution request" refers to an instruction and/or workflow describing one or more tasks to initiate and/or implement via the tech-bio exploration system 104 (and/or one or more tech-bio tools). For instance, an execution request can include a set of instructions that initiate a task at a tech-bio exploration tool (e.g., via inputs, instructions, output formats). In some cases, an execution request can include a set of instructions via a tool-specific API and/or communications protocol (e.g., JSON objects, function calls) to initiate and/or execute the one or more tech-bio exploration tools. In some cases, the AI tech-bio system 106 (via the language machine learning model) generates one or more execution requests for a tech-bio query. In addition, the AI tech-bio system 106 (via the language machine learning model) can also generate (and display) a displayable execution request (e.g., on a client device) to present instructions and/or a workflow utilized by the language machine learning model for a tech-bio query.

To illustrate, in reference to FIG. 2, the AI tech-bio system 106 can cause the language machine learning model 206 to generate a set of tasks (e.g., identify genes involved in DNA damage response, identify top 5 known genes involved in DNA Damage Response, identify additional genes that have similar phenoprints to the top 5 known genes, identify novel genes from the additional genes). Then, the language machine learning model 206 can execute the set of tasks via interactions with the tech-bio exploration tools, testing devices 210, and/or tech-bio exploration data repository 212 (e.g., bio-activity data repository). For instance, the language machine learning model 206 can cause a first tech-bio exploration tool from the tech-bio exploration tools 208 to identify genes involved in DNA damage response and rank the genes based on involvement in DNA damage response (e.g., via bio-activity heatmap models, target gene identification tools). Furthermore, the language machine learning model 206 can cause a second tech-bio exploration tool to compare relationships, based on phenoprint matching, between the identified top 5 genes involved in DNA damage response to additional genes within the tech-bio exploration data repository 212. Furthermore, the language machine learning model 206 can cause a third tech-bio exploration tool to identify novel genes from the additional matching genes (e.g., via comparison to gene and/or compound exploration program models that compare the genes to various networks and/or publications). Upon executing the various tasks, the language machine learning model 206 can utilize the obtained components of bio-activity data (from the various tasks) to generate the response 214*b*.

As shown in FIG. 2, the AI tech-bio system 106 (and/or the language machine learning model 206) can interact with a variety of tech-bio exploration tools. In some cases, tech-bio exploration tools can include, but are not limited to, bio-activity heatmap models, compound exploration program models, target priority editing models, molecular design models, synthesis planning models, ADMET prediction models, and/or human dose prediction models. In addition, the AI tech-bio system 106 can utilize the language machine learning model to determine and display (as part of the thought or action response) one or more tech-bio tools that will be executed to generate an observation (or output) for the prompt 204 (e.g., a tech-bio query).

As an example, the tech-bio exploration tools can include, but are not limited to, perturbation comparison tools and/or bio-activity heatmap models as described in UTILIZING MACHINE LEARNING MODELS TO SYNTHESIZE PERTURBATION DATA TO GENERATE PERTURBATION HEATMAP GRAPHICAL USER INTERFACES, U.S. patent application Ser. No. 18/526,707, filed Dec. 1, 2023, ADMET prediction models and/or drug-likeness matching tools as described in UTILIZING COMPOUND-PROTEIN MACHINE LEARNING REPRESENTATIONS TO GENERATE BIOACTIVITY PREDICTIONS, U.S. patent application Ser. No. 18/505,728, filed Nov. 9, 2023, compound exploration program models as described in UTILIZING BIOLOGICAL MACHINE LEARNING REPRESENTATIONS AND A LANGUAGE MACHINE LEARNING MODEL FOR INITIATING COMPOUND EXPLORATION PROGRAMS, U.S. patent application Ser. No. 18/521,910, filed Nov. 28, 2023, digital maps of biology models as described in UTILIZING MACHINE LEARNING AND DIGITAL EMBEDDING PROCESSES TO GENERATE DIGITAL MAPS OF BIOLOGY AND USER INTERFACES FOR EVALUATING MAP EFFICACY, U.S. patent application Ser. No. 18/392,989, filed Dec. 21, 2023, microscopy representation autoencoder models as described in UTILIZING MASKED AUTOENCODER GENERATIVE MODELS TO EXTRACT MICROSCOPY REPRESENTATION AUTOENCODER EMBEDDINGS, U.S. patent application Ser. No. 18/545,399, filed Dec. 19, 2023, and/or a mechanism of action prediction model tool as described in n GENERATING A MECHANISM OF ACTION REPRESENTATION FROM CELL REPRESENTATION EMBEDDINGS TO PREDICT A MECHANISM OF ACTION FOR A PERTURBATION, U.S. patent application Ser. No. 18/663,819, filed May 14, 2024 (hereinafter "application Ser. No. 18/663,819"), each of which are incorporated by reference in their entirety herein.

The tech-bio exploration tools can also include, liability prediction tools as described in CLASSIFYING COMPOUND LIABILITIES UTILIZING A MULTI-MODAL MACHINE LEARNING MODEL WITH MULTI-MODAL DIGITAL BIOMARKER DATA, U.S. patent application Ser. No. 18/637,970, filed Apr. 17, 2024, molecular large language generative tools as described in GENERATING LARGE-LANGUAGE-MODEL COMPATIBLE SEQUENTIAL ATTACHMENT-BASED FRAGMENT EMBEDDING MOLECULAR REPRESENTATIONS, U.S. patent application Ser. No. 18/750,828, filed Jun. 21, 2024, novel molecule generation tools as described in UTILIZING FLOW MEASURES OF A GENERATIVE STOCHASTIC MODEL AND ACTION VALUES OF AN ACTION-VALUE MODEL TO GENERATE STRUCTURAL REPRESENTATIONS, U.S. patent application Ser. No. 18/633,693, filed on Apr. 12, 2024, bioactivity prediction tools (e.g., compound graph neural networks), as described in TRAINING AND UTILIZING COMPOUND GRAPH NEURAL NETWORKS TO GENERATE BIOLOGICAL ACTIVITY PREDICTIONS FROM INPUT CHEMICAL COMPOUNDS, U.S. patent application Ser. No. 18/750,813, filed on Jun. 21, 2024, multimodal prediction tools (e.g., tools for generating perturbation scores across phenomic and transcriptomics), as described in MULTI-MODAL PAIR MATCHING FOR A MULTI-MODAL MACHINE LEARNING MODEL LEARNING PROCESS, U.S. patent application Ser. No. 18/672,492, filed May 23, 2024, cellular perturbation comparison tools (e.g., gene/compound phenomic comparison prediction tools), as described in DETERMINING PHENOMIC RELATIONSHIPS BETWEEN COMPOUNDS AND CELL PERTURBATIONS UTILIZING MACHINE LEARNING MODELS, U.S. patent application Ser. No. 18/753,906, filed on Jun. 25, 2024, binding prediction tools (e.g., tools for predicting binding affinities between compounds and proteins), as described in TRAINING AND USING GENERATIVE THERMODYNAMICS NEURAL NETWORKS TO DETERMINE BINDING AFFINITIES FROM ENERGY DISTRIBUTIONS, U.S. patent application Ser. No. 18/825,331, filed Sep. 5, 2024, causal prediction tools (e.g., generating causation predictions utilizing clinical data and machine learning models), as described in UTILIZING A CLINICAL-PHENOMICS CAUSAL DISCOVERY FRAMEWORK TO GENERATE CAUSAL DISCOVERY PREDICTIONS, U.S. patent application Ser. No. 18/738,927, filed Jun. 10, 2024, compound activity prediction tools (e.g., compound-perturbation anomaly detection models) as described by UTILIZING A COMPOUND-PERTURBATION ANOMALY DETECTION MODEL TO IDENTIFY OUTLIER COMPOUND-PERTURBATION RELATIONSHIPS, U.S. patent application Ser. No. 18/887,587, filed on Sep. 17, 2024 (hereinafter "application Ser. No. 18/887,587"), contrastive molecular structure and phenomic image comparison tools, as described in UTILIZING CONTRASTIVE MACHINE LEARNING MODELS TO EXTRACT JOINT-SPACE MOLECULAR-PHENOMIC EMBEDDINGS FROM MOLECULAR STRUCTURES OR PHENOMIC IMAGES, U.S. patent application Ser. No. 18/930,066, filed on Oct. 29, 2024, each of which are incorporated by reference in their entirety herein.

Furthermore, the tech-bio exploration tools can also include, experiment design interfacing tools as described in DETECTING ANALYSIS MODEL COMPATIBILITIES WITH COMPLEX EXPERIMENT DESIGNS TO GENERATE EXPERIMENT DESIGN AND ANALYSIS MODEL COMPATIBILITY GRAPHICAL USER INTERFACES, U.S. patent application Ser. No. 18/390,989, filed on Dec. 20, 2023, assay protocol and execution queue user interface tools as described in GENERATING ASSAY PROTOCOL AND EXECUTION QUEUE USER INTERFACES FOR EFFICIENT EXECUTION AND METADATA TRACK-ING OF COMPLEX AUTOMATED EXPERIMENTS, U.S. patent application Ser. No. 18/415,397, filed on Jan. 17, 2024, graphical user interface tools for defining and matching experimental purposes and conditions to generate well plate layouts and well compositions as described in SYSTEMS AND GRAPHICAL USER INTERFACES FOR GENERATING AND TRANSMITTING WELL PLATE LAYOUTS AND WELL COMPOSITIONS FOR PERTURBATION EXPERIMENT WORKFLOWS, U.S. patent application Ser. No. 18/640,343, filed Apr. 19, 2024, a tractability machine learning model tool that generates tractability scores for a multi-domain machine learning model for generating improved machine learning predictions as described in UTILIZING A TRACTABILITY MACHINE LEARNING MODEL TO GENERATE TRACTABILITY SCORES FOR A MULTI-DOMAIN MACHINE LEARNING MODEL FOR IMPROVED MACHINE LEARNING PREDICTIONS, U.S. patent application Ser. No. 18/590,057, filed Feb. 28, 2024, representation learning tools for active learning of pairwise interactions between perturbations as described in ACTIVE LEARNING FOR DISCOVERING PAIRWISE INTERACTIONS VIA REPRESENTATION LEARNING, U.S. patent application Ser. No. 18/639,146, filed Apr. 18, 2024, user interface tools for designing cell-based screening assay experiments as described in METHODS AND USER INTERFACES FOR DESIGNING CELL-BASED SCREENING ASSAY EXPERIMENTS, U.S. patent application Ser. No. 18/640,702, filed Apr. 19, 2024, neural network tools for generating quantum mechanics property predictions for molecular dynamics simulations of compound geometries as described in TRAINING AND UTILIZING NEURAL NETWORK POTENTIAL MODELS HAVING A MULTI-TASK ARCHITECTURE TO GENERATE QUANTUM MECHANICS PROPERTY PREDICTIONS, U.S. patent application Ser. No. 18/913,456, filed Oct. 11, 2024, and an active machine learning tool for biological data acquisition as described in ACTIVE LEARNING TECHNIQUES FOR DEVELOPING MAP PREDICTION MACHINE LEARNING MODELS TO GENERATE MAPS OF BIOLOGY, U.S. patent application Ser. No. 18/990,261, filed Dec. 20, 2024, each of which are incorporated by reference in their entirety herein.

In addition, the tech-bio exploration tools can also include, computational drug target selection tools as described in COMPUTATIONAL DRUG TARGET SELECTION, U.S. patent application Ser. No. 18/138,705, filed on Apr. 24, 2023, active learning-based computational drug design tools as described in DRUG OPTIMIZATION BY ACTIVE LEARNING, U.S. patent application Ser. No. 18/231,219, filed on Aug. 7, 2023, coverage score-based active learning computational drug design tools as described in ACTIVE LEARNING USING COVERAGE SCORE, U.S. patent application Ser. No. 18/138,021, filed on Apr. 21, 2023, computational drug target selection tools as described in COMPUTATIONAL DRUG TARGET SELECTION, International Pub. No. WO 2024/194479, filed on Mar. 22, 2024, and/or tools for determining interaction between biological cells as described in METHODS FOR DETERMINING INTERACTION BETWEEN BIOLOGICAL CELLS, U.S. patent application Ser. No. 16/488,196, filed on Feb. 23, 2018, each of which are incorporated by reference in their entirety herein.

Furthermore, the tech-bio exploration tools can also include a platform that utilizes artificial intelligence (e.g., deep learning and/or knowledge graphs) to ingest biological data to identify drug targets across disease areas for drug development by extracting insights from the public corpus of biological data. In addition, the tech-bio exploration tools can also include a platform that utilizes artificial intelligence to automatically design and prioritize novel drug compounds for synthesis (via iterative optimization of synthesis and testing cycles). Indeed, the AI tech-bio system 106 can enable the language machine learning model to interact with such platforms in accordance with one or more implementations herein.

Although one or more particular tech-bio exploration tools are described above, in one or more instances, the AI tech-bio system 106 can enable the language machine learning model to interact with a variety of tech-bio exploration tools. For example, as shown in FIGS. 7A-7G and 8A-8L, the AI tech-bio system 106 can enable the language machine learning model to interact with (or execute tasks via) tech-bio exploration tools, such as, a compound-gene activity modeling tool, a compound liability prediction tool, a compound generation tool, a pheno-similarity prediction tool, a binding prediction model, a molecular pair series assignment tool, a phenomic clustering tool, a cluster analysis comparison tool, a mechanism-of-action modeling tool, a phenotype to target determination tool, phenoprint comparison tool, ADMET prediction models and/or drug-likeness matching tools, and/or compound (or chemical) neighborhood identification tool.

In addition, the AI tech-bio system 106 can enable the language machine learning model to interact with a variety of third-party (or external) tools, such as, third-party vendor systems, third-party automated lab tools, and/or third-party image editing tools. For example, the AI tech-bio system 106 can utilize APIs and other execution requests (via the language machine learning model) to cause third-party (or external tools) to execute one or more automated lab experiments, generate or retrieve phenomic images and/or other images, and/or initiate purchases of compounds or other material related to the workflow within the computerized bio-activity discovery pipeline initiated and/or utilized by the language machine learning model.

In some implementations, the AI tech-bio system 106 facilitates a front-end application that displays an interactive interface to query the tech-bio exploration system 104. For instance, the AI tech-bio system 106 provides, for display within an interactive user interface, options to select, type, and/or dictate prompts as tech-bio queries. Then, the AI tech-bio system 106 utilizes the prompts with the language machine learning model to access one or more tech-bio exploration tools and/or tech-bio exploration data repositories of the tech-bio exploration system 104 to generate and/or obtain a response to the tech-bio queries (in accordance with one or more implementations herein). Indeed, in some cases, the AI tech-bio system 106 can provide a response with relevant bio-activity data for the tech-bio query in the interactive user interface without providing direct access to the tech-bio exploration system 104 and/or the tech-bio exploration tools. Indeed, in some cases, the AI tech-bio system 106 provides the interactive user interface with tech-bio query prompts as a plug-in and/or application accessible to third-party applications and/or users (externally from the tech-bio exploration system 104).

Figure 3:
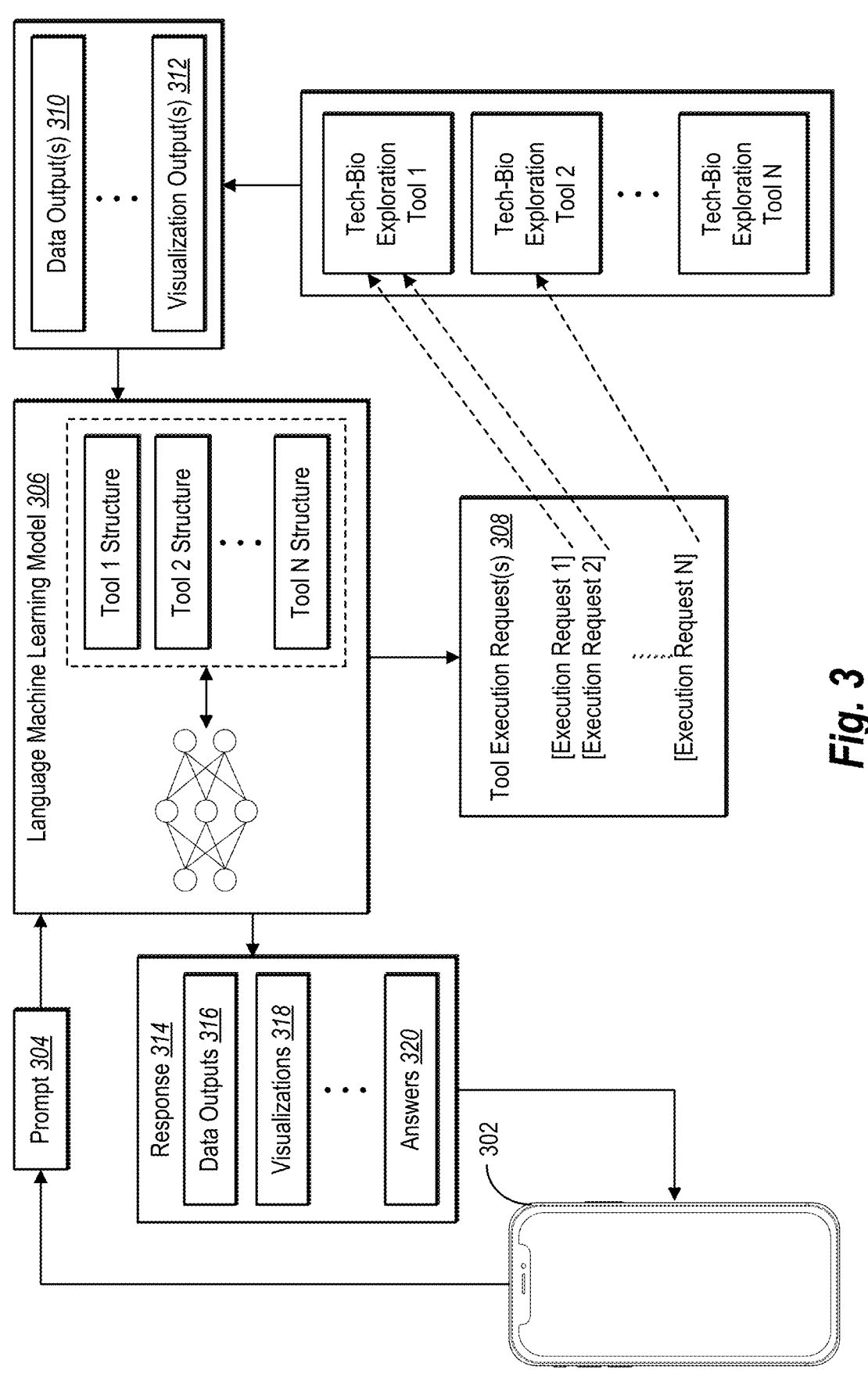
FIG. 3 illustrates an AI tech-bio system utilizing a language machine learning model to execute various tech-bio exploration tools for prompt-based tech-bio queries in accordance with one or more embodiments.

Furthermore, FIG. 3 illustrates the AI tech-bio system 106 utilizing a language machine learning model to execute various tech-bio exploration tools for prompt-based tech-bio queries to generate a response for the prompt-based tech-bio queries. For instance, FIG. 3 illustrates the AI tech-bio system 106 training a language machine learning model to understand and execute various tech-bio exploration tools. Moreover, FIG. 3 illustrates the AI tech-bio system 106 receiving a prompt and generating tool execution requests for the prompt to perform one or more tasks in one or more tech-bio exploration tools to generate a response for the prompt (e.g., a tech-bio query).

For instance, as shown in FIG. 3, the AI tech-bio system 106 utilizes tool structures of tech-bio exploration tools to train (or teach) a language machine learning model 306. For example, the AI tech-bio system 106 can train the language machine learning model 306 by exposing the language machine learning model 306 to the tool structures of the tech-bio exploration tools (e.g., tool structures 1-N for the tech-bio exploration tools 1-N). In some cases, the AI tech-bio system 106 utilize single shot or few shot learning to cause the language machine learning model 306 to ingest (or read) the tool structure of a tech-bio exploration tool to learn context for the tech-bio exploration tool, to learn how to execute the tech-bio exploration tool (e.g., specific execution requests and/or calls), and/or to learn when to apply the tech-bio exploration tool (for specific prompts).

In one or more implementations, the tool structure can include descriptions corresponding to the tech-bio exploration tool that defines and/or instructs various aspects of the tech-bio exploration tool (e.g., purpose of the tech-bio tool, inputs of the tech-bio tool, outputs of the tech-bio tools, dependencies of the tech-bio tool). In some cases, the tool structure can include a catalog (or library) of API calls and/or other calls for the tech-bio exploration tool. In one or more instances, the AI tech-bio system 106 can utilize source code of the tech-bio tool as part of the tool structure.

In some embodiments, the AI tech-bio system 106 can fine tune a language machine learning model for a particular tool structure of a tech-bio tool. For instance, the AI tech-bio system 106 can iteratively train a language machine learning model utilizing training prompts and ground truth calls to the particular tech-bio tool to fine tune the language machine learning models predictions on utilizing the tech-bio tool for particular prompts. As an example, the AI tech-bio system 106 can train a language machine learning model via back propagation of a loss between a predicted instruction to a tech-bio tool and a ground truth instruction to tech-bio tool for a particular training prompt.

In one or more cases, the AI tech-bio system 106 can train (or teach) (e.g., via single shot learning, few shot learning, iterative training) a single language machine learning model for multiple tech-bio exploration tools, multiple language machine learning models for various combinations of tech-bio exploration tools, and/or a language machine learning model for a tech-bio exploration tool. Indeed, the AI tech-bio system 106 can train the language machine learning model as an advanced reasoner model that analyzes prompts to understand a task, break the task down into component parts, generating a plan or list of tasks to execute the task, and interact with one or more tech-bio exploration tools to execute the task (e.g., to generate and/or obtain bio-activity data from the tools).

Additionally, in some implementations, the AI tech-bio system 106 can utilize the language machine learning model to generate recommended descriptors (and/or other tool structures) for one or more tech-bio exploration tools. In particular, the AI tech-bio system 106 can utilize the language machine learning model to analyze a tool structure of a tech-bio exploration tool to generate a recommended tool structure that improves the utilization of one or more language machine learning models on the tech-bio exploration tool. For instance, the language machine learning model can generate recommended descriptions and/or API call library descriptions for an existing tech-bio exploration tool to improve interactions between the tech-bio exploration tool and one or more language machine learning models (in accordance with one or more implementations herein).

In addition, in one or more instances, the AI tech-bio system 106 can provide, for display within one or more interactive user interfaces, tools to add a tech-bio exploration tool as a recognized tool by the language machine learning model. For example, the AI tech-bio system 106 can enable user interface interactions to receive or generate tech-bio exploration tool structures (e.g., tool name, tool descriptors, tool inputs, tool input formats, tool output formats) to integrate a tech-bio exploration tool with the large language machine learning model of the AI tech-bio system 106. For instance, the AI tech-bio system 106 can enable the addition of a tech-bio exploration tool as described below (e.g., with reference to FIG. 12).

Furthermore, in one or more implementations, the AI tech-bio system 106 can generate (or utilize) one or more prompts to teach a language machine learning model to accurately interact with one or more tech-bio exploration tools to generate outputs for a tech-bio query. For instance, the AI tech-bio system 106 can generate role framing prompts that instruct (or teach) the language machine learning model to approach an analysis for a tech-bio query from a perspective or style (to influence a tone, style, or depth of responses generated by the language machine learning model). As an example, the AI tech-bio system 106 can generate role framing prompts instructing the language machine learning model to respond as a specialized chemist, a specialized biologist, scientist, engineer, and/or a pharmacist. In some instances, the AI tech-bio system 106 can generate (or utilize) one or more prompts to teach or instruct a language machine learning model to generate particular responses utilizing, but not limited to, specific formatting, content types, and/or lengths. For example, the AI tech-bio system 106 can generate prompts to specify a particular output format (e.g., a visual diagram, a dataset table, a list, a CSV file, a text-based response).

Furthermore, as shown in FIG. 3, the AI tech-bio system 106 receives a prompt 304 from a client device 302. In some instances, the prompt 304 can include a free-form text query from the client device 302 (e.g., as shown in FIGS. 8A-8L). In one or more instances, the prompt 304 can include a prompt built from one or more tech-bio query templates (e.g., as shown in FIGS. 6A-6C and FIGS. 7A-7G). For instance, the prompt 304 can include a template-based text query that provides a particular set of instructions (e.g., "find me all the genes that are phenotypically similar to [input x]," "identify genes involved in [input y]"). Indeed, the AI tech-bio system 106 can receive text input from the client device 302 to complete the template prompt (e.g., provide inputs for "[input x]" and/or "[input y]"). For instance, the AI tech-bio system 106 can display and receive selections from a menu of prompt templates in which variables are editable (e.g., [input x], [input y]).

Then, as further shown in FIG. 3, the AI tech-bio system 106 utilizes the prompt 304 with the language machine learning model 306 to generate tool execution request(s) 308. For example, the AI tech-bio system 106 can, utilizing the language machine learning model 306, select one or more tech-bio tools in response to the prompt 304 (e.g., the tech-bio query). Indeed, the AI tech-bio system 106 can match language from the prompt 304 to one or more appropriate tech-bio exploration tools. For instance, in some cases, the AI tech-bio system 106 can utilize pre-defined mappings between prompt templates and one or more tech-bio tools. In particular, the AI tech-bio system 106 can select tech-bio tools associated with a selected tech-bio prompt template (selected by a user) and generate execution requests for the selected tech-bio tools to accomplish one or more tasks associated with the tech-bio query template selected by a user.

Moreover, in some instances, the AI tech-bio system 106 selects tech-bio tools for a tech-bio query based on the language in the prompt 304 (e.g., the tech-bio query) and descriptions of the one or more tech-bio exploration tools. For instance, the AI tech-bio system 106, via the language machine learning model 306, analyzes the prompt 304 to determine a workflow or tasks to initiate to accomplish a tech-bio query corresponding to the prompt 304. Moreover, the AI tech-bio system 106, via the language machine learning model 306, predicts or identifies tech-bio tools (based on the tech-bio tool structure descriptions of the tech-bio tools) that are utilized to perform the determined workflow or tasks. For example, the AI tech-bio system 106, via the language machine learning model 306, can utilize a mapping between particular tasks (or tasks descriptions) and tech-bio tools to select a tech-bio tool for a tech-bio query by identifying matching the task described in the tech-bio query to the one or more mapped task descriptions.

In some instances, the AI tech-bio system 106, via the language machine learning model 306, utilizes a description comparison to select tech-bio tools for the tech-bio query. For example, the AI tech-bio system 106 compares the tech-bio query in the prompt 304 to one or more descriptors corresponding to the tech-bio tools to identify similar descriptions (e.g., via similarity distances, such as, cosine similarities, Euclidean distances, or clustering). Moreover, the AI tech-bio system 106 utilizes similar descriptions between tech-bio tools and the prompt 304 (e.g., descriptions that meet a threshold similarity score or distance) to identify (or select) tech-bio tools for the prompt 304.

In some instances, the AI tech-bio system 106 utilizes a shared embedding space to select tech-bio tools for the tech-bio query. For instance, the AI tech-bio system 106 generates embeddings for the descriptions corresponding to the tech-bio tools and the descriptions corresponding to the prompt 304. Moreover, the AI tech-bio system 106 compares the embeddings (e.g., word embeddings) in a shared embedding space to determine similarity distances (e.g., cosine similarities, clustering, Euclidean distance) between the embeddings. Moreover, the AI tech-bio system 106 can utilize tech-bio tool description embeddings that satisfy a threshold similarity distance with the tech-bio query description from the prompt 304 to select the tech-bio tools for the prompt 304 (e.g., via the tech-bio tools corresponding to the tech-bio tool description embeddings).

In addition, the AI tech-bio system 106 (via the language machine learning model 306) can utilize the tech-bio query (from the prompt 304) and/or the selected tech-bio tools to generate modified prompts and/or execution requests. For example, the AI tech-bio system 106 can generate the modified prompts as displayable execution requests that indicate a workflow or approach taken by the language machine learning model to generate an observation or response to the tech-bio query in the prompt 304. In addition, the AI tech-bio system 106 can also generate execution requests to transmit to the tech-bio tools to cause the tech-bio tools to execute one or more functions to generate observations and/or output results for the tech-bio query from the prompt 304.

For instance, the AI tech-bio system 106 can generate a modified prompt that includes the user-filled template prompt appended with descriptions for one or more tech-bio exploration tools corresponding to the template prompt. For example, the AI tech-bio system 106 can modify a query prompt by adding a description of the purpose or function of each tech-bio exploration tools and a description of the format of requests for each tool. In some instances, the AI tech-bio system 106 can utilize mappings of tasks to the template prompts to generate a modified prompt that includes descriptions for multiple tasks to accomplish the query in the template-based prompt. For instance, for a template-based prompt that provides a particular set of instructions (e.g., "find me all the genes that are phenotypically similar to [input x]"), the AI tech-bio system 106 can identify multiple tasks corresponding to the template-based prompt. As an example, the AI tech-bio system 106 can identify tasks, such as, access a list of genes, identify phenotype mappings/comparisons between the list of genes and [input x] gene, select genes from the list of genes that are phenotypically similar to the [input x] gene. Then, the AI tech-bio system 106 can generate a modified prompt that includes the identified tasks and descriptions for one or more tech-bio exploration tools corresponding to the template prompt (and/or all available tech-bio exploration tools).

In some cases, the AI tech-bio system 106 can generate a modified prompt from a free-form text prompt. For example, the AI tech-bio system 106 can append descriptions (e.g., tool structures) from one or more tech-bio exploration tools to the free-form text prompt to generate the modified prompt. In some cases, the AI tech-bio system 106 can identify one or more tasks described in the free-form text prompt. Subsequently, the AI tech-bio system 106 can generate the modified prompt by reformatting the prompt to describe the identified one or more tasks and descriptions (e.g., tool structures) from one or more available tech-bio exploration tools.

For example, the AI tech-bio system 106 can generate the modified prompt as a displayable execution request. In particular, the AI tech-bio system 106 can generate a modified prompt that describes one or more tasks determined, via the language machine learning model 306, for the tech-bio query (e.g., to utilize one or more tech-bio tools to execute tasks for the tech-bio query). In one or more implementations, the AI tech-bio system 106 generates a modified prompt that includes one or more tech-bio tools selected for the tech-bio query (by the language machine learning model). In particular, the AI tech-bio system 106, utilizing the language machine learning model, selects one or more tech-bio tools (based on learned descriptions or structures of the tech-bio tools) and generates a modified prompt (or displayable execution request) that indicates the selected one or more tech-bio tools. Indeed, the AI tech-bio system 106 can display the modified prompt (or execution request) within a query interface (e.g., as a chat response) as a response from the language machine learning model to indicate to a user the tech-bio tools selected to execute one or more tasks for the user selected (or provided) tech-bio query. In some implementations, the AI tech-bio system 106 displays a modified prompt (or execution request) that describes one or more actions or tasks to be taken in response to the tech-bio query and also indicates the selected (or to be utilized) tech-bio tools for the one or more actions. In some cases, the AI tech-bio system 106 also displays, as part of the modified prompt (utilizing the language machine learning model), inputs (e.g., selected perturbations, output data from previous responses created from tech-bio tools and the language machine learning model) provided to (or to be provided to) the one or more selected tech-bio tools.

Furthermore, the AI tech-bio system 106, via the language machine learning model, can generate execution requests for one or more tech-bio exploration tool by utilizing instructions (as execution request) that are compatible (or understood) by the tech-bio exploration tool. For instance, the language machine learning model can utilize a reformatted and/or modified prompt (having task descriptions and/or tech-bio tool descriptions) to generate the execution requests. In some cases, the language machine learning model 306 can generate a string of instructions or code (e.g., Python code, Java code, Javascript) as execution requests based on analyzing the modified prompt having one or more task descriptions and tech-bio tool descriptions. For example, in some cases, the language machine learning model 306 generate a set of API calls (based on API calls in a library of the tech-bio exploration tool) that match the requests and description in a modified version of the prompt 304 as tool execution request(s).

For instance, the AI tech-bio system 106, via the language machine learning model 306, analyzes a modified prompt (having descriptions for one or more tech-bio tools) from the prompt 304 to determine one or more tasks for the tech-bio exploration tools to generate and/or obtain bio-activity data in response to the prompt 304. Based on the determined one or more tasks, the language machine learning model 306 generates the tool execution request(s) 308 as execution requests that cause the tech-bio exploration tools to perform the one or more determined tasks.

As an example, the AI tech-bio system 106 can read an input prompt and match it to one or more tech-bio tool descriptions to identify one or more tech-bio tools to utilize for the prompt. Subsequently, the AI tech-bio system 106 can generate a modified prompt that appends information (from tool structures) of various tech-bio tools (e.g., matched tech-bio tools and/or all available tech-bio tools) to include descriptions of the tech-bio tools within the modified prompt. Moreover, the language machine learning model 306 can analyze the modified prompt to select appropriate tech-bio tools for the tasks described in the prompt.

Furthermore, the language machine learning model 306 can construct the input for API calls associated with the tech-bio tool utilizing an API library (or dictionary) of the tech-bio tool. Indeed, the language machine learning model 306 can generate key value pairs for a particular API call of a tech-bio tool and generate a string of the key value pairs to transmit to the tech-bio tool (as one or more execution requests). In some instances, the language machine learning model 306 can generate a JSON structure that includes one or more values or other data as input data for a tech-bio tool (e.g., to transmit to the tech-bio tool perform one or more tasks).

Although one or more embodiments illustrate the AI tech-bio system 106 appending tech-bio tool descriptions to a prompt to assist the language machine learning model to generate execution requests for one or more tech-bio tools, in some implementations, the AI tech-bio system 106 can train (or tune) the language machine learning model to automatically generate execution requests from input prompts. For instance, the language machine learning model can utilize training (or ingestion) of tool structures of the tech-bio exploration tools to analyze a prompt to determine tasks described in the prompt, determine or predict appropriate tech-bio tools for the tasks, and generate execution requests (as described herein) to accomplish the determined tasks on the one or more tech-bio exploration tools. Furthermore, in some implementations, the language machine learning model can generate execution request(s) and display the execution request(s) within a client device (e.g., as a chat message in a graphical user interface).

Upon transmitting the string of API calls (e.g., execution requests), the AI tech-bio system 106 causes a tech-bio exploration tool to analyze the string of API calls, execute appropriate tasks (or models) for the API calls using the included key value pairs, and generate bio-activity data from executing the appropriate tasks. Moreover, upon execution of the tech-bio exploration tool based on the transmitted tool execution request, the language machine learning model 306 can receive output from the tech-bio exploration tool. Indeed, the language machine learning model 306 can receive, from a tech-bio exploration tool, string output that includes one or more data output(s) 310, visualization output(s) 312 (e.g., string output instructions to generate a display of a visualization), and/or one or more artifacts created from the data output(s) 310) (e.g., as a response 314).

In some instances, the AI tech-bio system 106 (via the language machine learning model 306) generates execution requests that are tech-bio tool specific. For example, the AI tech-bio system 106 can generate execution requests that include input formats, instruction formats, output format instructions, and/or other tool configurations that are specific to a particular tech-bio tool or a particular tech-bio tool API. For instance, the AI tech-bio system 106 can generate execution requests that include varying numbers of input data based on the number of inputs a particular tech-bio tool utilizes. Additionally, the AI tech-bio system 106 can instructions (as part of an execution request) to indicate instructions for a particular tech-bio tool to generate outputs in a specified format (e.g., a specific table size, table style, cluster size, list size). In addition, the AI tech-bio system 106 can generate an execution request having configuration data (for a tech-bio tool), such as, but not limited to, cluster size settings, similarity distance threshold settings, and/or confidence threshold settings.

Furthermore, in one or more instances, the AI tech-bio system 106 can determine (or generate), utilizing the language machine learning model, a thought, action, or input (as described above) and utilize the thought, action, or input as part of the modified prompt (or displayable execution request). For instance, the AI tech-bio system 106 can utilize the language machine learning model to generate a justification and/or reasoning (as the thought) to describe a workflow or approach determined by the language machine learning model to generate a response for the tech-bio query and/or for the tech-bio tool selection in the execution request. In addition, the AI tech-bio system 106 can utilize the language machine learning model to determine (and/or display) one or more selected tech-bio tools to utilize as actions. In some cases, the AI tech-bio system 106 can display an execution requestion as an action taken by the language machine learning model. In addition, the AI tech-bio system 106 can also utilize the language machine learning model to display (or determine) inputs utilized with the selected tech-bio tools (or in a workflow) to generate a response for the tech-bio query.

Moreover, the AI tech-bio system 106 can utilize the various thoughts, actions, and/or inputs generated via the language machine learning model to determine (or execute) one or more tasks in response to a tech-bio query. For instance, the AI tech-bio system 106 can, upon executing one or more tasks using one or more tech-bio tools for the tech-bio query, further utilize the language machine learning model to select between generating the response to the tech-bio query or executing one or more additional tech-bio tools. For example, the AI tech-bio system 106 can execute additional tasks, via the language machine learning model, for the tech-bio query response (using outputs or observations from completed tasks in the workflow) and/or determine that a final response or observation (or output) is available for the tech-bio query to utilize as a response to the tech-bio query.

As an example, as part of the execution flow logic, a tech-bio exploration tool can generate a string output that lists a number of genes. Upon transmitting the string output to the language machine learning model 306, the language machine learning model 306 can parse the list of genes and understand (or identify) the genes listed in the string output. Then, the language machine learning model 306 can utilize the list of genes to generate the response 314 (e.g., an answer to a query for a particular set of genes).

In some cases, as part of the execution flow logic, the language machine learning model 306 can utilize output from a tech-bio exploration tool as input in another tech-bio exploration tool (e.g., when multiple tasks are identified from the prompt 304). For instance, the language machine learning model 306 can initiate an additional execution request by generate the execution request that uses the output from the tech-bio exploration tool as an input for the additional tech-bio exploration tool. As an example, the language machine learning model 306 can generate an execution request that utilizes a list of genes (output by a tech-bio tool) as input into another tech-bio tool that identifies target compounds for the list of genes, identifies novel genes from the list of genes, and/or determines liability scores for the list of genes. Indeed, the language machine learning model 306 can utilize various combinations of outputs from one or more tasks provided to tech-bio exploration tools (e.g., via generated tool execution requests) as inputs to one or more additional tech-bio exploration tools for additional (subsequent) tasks identified for the prompt 304.

Indeed, as shown in FIG. 3, the language machine learning model 306 can generate various combinations of tool execution request(s) 308 (e.g., execution requests 1-N) for the prompt 304. Moreover, as shown in FIG. 3, the language machine learning model 306 can utilize the tool execution request(s) 308 with the tech-bio exploration tools 1-N to generate various data output(s) 310 and/or visualization output(s) 312. Indeed, the language machine learning model 306 can utilize the tool execution request(s) 308 simultaneously, in sequential order, upon satisfying a dependency (e.g., receiving output data from one tech-bio tool to use as an input in another tech-bio tool), and/or in random order to generate or obtain the data output(s) 310 and/or the visualization output(s) 312 (e.g., as bio-activity data). Furthermore, as mentioned above, the AI tech-bio system 106 can display the one or more tool execution request(s) 308 as language machine learning model thoughts (or workflows) to (transparently) indicate the tasks or process taken by the language machine learning model.

Indeed, the AI tech-bio system 106 can receive a variety of prompts and utilize the language machine learning model (in accordance with one or more implementations herein) to execute requests with one or more tech-bio exploration tools to generate and/or obtain bio-activity data in response to the prompts. To illustrate, in some cases, the AI tech-bio system 106 can receive a prompt ("give me 10 novel targets for disease X using tech-bio exploration system maps, such as heatmaps and/or maps of biology) and, in response, the AI tech-bio system 106 can utilize the language machine learning model to identify novel targets for disease X by querying and leveraging a tech-bio exploration tool for tech-bio exploration system maps. As another example, the AI tech-bio system 106 can receive a second prompt ("given the target(s) identified above, give me 10 chemical starting points"). In response to the second prompt, the language machine learning model of the AI tech-bio system 106 can utilize a first tech-bio exploration tool for tech-bio exploration system maps to identify compound(s) or gene(s), utilize a second tech-bio exploration tool (e.g., a compound-protein machine learning representation tool) to identify compound(s), utilize a third tech-bio exploration tool (e.g., for generative models) to identify novel compounds, utilize a fourth tech-bio exploration tool to apply one or more medicinal chemistry filters, and utilize a fifth tech-bio exploration tool to optimize compound(s) and/or continuously propose new compounds.

Additionally, as shown in FIG. 3, the language machine learning model 306 receives the data output(s) 310 (and/or visualization output(s) 312) from the tech-bio exploration tools 1-N (e.g., upon execution of one or more tool execution request(s) 308). Indeed, the data output(s) 310 can include various bio-activity data generated and/or obtained from the tech-bio exploration tools (e.g., lists of genes, lists of compounds, disease to target identifications, ADMET properties, drug-likeness determinations). Moreover, the visualization output(s) 312 can include various visual bio-activity data generated and/or obtained from the tech-bio exploration tools (e.g., perturbation images, maps of biology, perturbation heatmaps).

In one or more instances, the language machine learning model 306 can analyze the data output(s) 310, visualization output(s) 312, and/or other outputs of the tech-bio exploration tools to generate a response 314 to the prompt 304. As shown in FIG. 3, the response 314 can include data outputs 316, visualizations 318, and/or answers 320. Indeed, the language machine learning model 306 can generate the response 314 to list bio-activity data that is requested from a query in the prompt 304. In some cases, the language machine learning model 306 can generate the response 314 to illustrate and/or present a visualization for a query in the prompt 304. Moreover, in some instances, the language machine learning model 306 can generate the response 314 to be an answer 320 to a question presented in the prompt 304 (e.g., the language machine learning model 306 can analyze bio-activity data retrieved using the tech-bio exploration tools to determine an answer to a question within a query).

Furthermore, the AI tech-bio system 106 can utilize the response 314 to provide, for display within a graphical user interface of the client device 302, one or more visual responses to the tech-bio query presented in the prompt 304. For example, the AI tech-bio system 106 can display a chat message for the response 314 within the client device 302. Indeed, the AI tech-bio system 106 can display a chat message for the response 314 to display one or more results of the tech-bio tools or for executing the tech-bio query and/or a data presentation (e.g., in a requested format, such as, but not limited to a list, a matrix, and/or a table). In some cases, the AI tech-bio system 106 can display charts, graphs, images, and/or reports generated utilizing bio-activity data (or outputs) from the response 314.

In some instances, the AI tech-bio system 106 can generate a variety of artifacts (and/or links to artifacts) that represent data outputs generated by the tech-bio tools. For example, the AI tech-bio system 106 can generate files (e.g., image files, CSV files, text files) to represent output data generated by a tech-bio tool. Indeed, in one or more instances, the AI tech-bio system 106 can generate files (e.g., CSV files) to provide larger output data sets in response to a tech-bio query (e.g., a data set that is unable to fit in a chat message and/or is difficult to navigate within a chat user interface).

In some cases, the AI tech-bio system 106 can generate various types of visualization data. For instance, the AI tech-bio system 106 can utilize a language machine learning model to generate visuals that include, but are not limited to, spider plots, molecule images, tables, graphs, charts, heatmaps, and other forms of visualizations (e.g., for bio-activity and/or target interactions and relationships, ligands, molecule structures, phenotypes, mechanisms of action). In one or more instances, the AI tech-bio system 106 can generate visualization data that visually (e.g., via one or more visuals described above) represents output data from one or more tech-bio exploration tool (in accordance with one or more implementation herein).

Moreover, in one or more implementations, the AI tech-bio system 106 generates interactive visualization data. For example, the AI tech-bio system 106 can generate interactive visualization data that includes one or more interactive graphical user interface elements to enable functionality and/or additional data within the visualization data. For example, the AI tech-bio system 106 can generate interactive visualization data that enables navigation within the visualization (e.g., zooming, rotation, movement around one or more axis). In some instances, the AI tech-bio system 106 can generate interaction visual diagrams that enable hovering interactions to display additional data for a particular data point in the visualization, and/or links to navigate to specific data for the particular data point represented in data visualization.

In addition, the AI tech-bio system 106 (via the language machine learning model) can generate multiple visual diagrams for a response and enable selectable options (e.g., via a dropdown menu or navigation tab) to navigate between multiple visual diagrams (e.g., visual diagrams representing different aspects of the data, such as, drug likeness, phenomic relationships, toxicity, confidence or accuracy). In some instances, the AI tech-bio system 106 (via the language machine learning model) can generate multiple visual diagrams for a response and enable selectable options to navigate between multiple visual diagrams having different formats, such as, but not limited to, 3D charts, 3D scatter plots, scatter plots, graphs, 3D graphs, bar charts, and/or radar charts. As an example, the AI tech-bio system 106 generating and displaying various responses through visualizations and/or other formats and interactive interfaces is illustrated in FIGS. 7A-7G and 8A-8L).

Furthermore, in some cases, the language machine learning model can also generate and display a rationalization and/or reasoning behind one or more determined steps in the execution of tech-bio exploration tools (e.g., as a thought, action, or input as described herein). As an example, the language machine learning model can describe that a relationship was identified through a biology map because it was phenosimilar to other known proteins with supporting literature and/or describe how the language machine learning model utilized a tech-bio exploration tool to filter and select a top X compounds.

As another example, the AI tech-bio system 106 can receive a prompt ("give me 10 novel targets for X disease (related to DNA damage response) and, in response, the language machine learning model can list known genes associated with disease X and query a cell map for novel and/or similar genes. In some cases, the AI tech-bio system 106 can receive a prompt, such as "help me visualize target relationships through heatmaps, graphs, etc." and the language machine learning model can generate one or more visualizations from bio-activity data in response.

Furthermore, in some cases, the AI tech-bio system 106 can receive a prompt, such as "from the targets identified above, give me a list of 5 chemical starting points (series) with relevant activity" and "expand the list of 5 starting points with novel compounds from the same series." In response to the prompt, the language machine learning model can utilize cell maps tool and/or a gene matching tool (e.g., a tech-bio exploration tool) to identify one or more active compounds and further utilize a generative model tool to identify novel compounds. Moreover, in some instances, the AI tech-bio system 106 can further receive a prompt, such as "filter out non-drug-like molecules." In response to the prompt, the language machine learning model can utilize an ADMET predictions tool to compute ADMET properties and drug-likeness of the identified molecules (e.g., compounds). Moreover, the AI tech-bio system 106 can also receive a prompt to "pick 10 molecules from the filtered list and send a purchase order to a vendor" such that the language machine learning model executes a tech-bio tool (e.g., a third party tool) to initiate a purchase order. Furthermore, the AI tech-bio system 106 can also receive a prompt to "render the 10 molecules in a single markdown image format" and, in response, the language machine learning model can generate visualizations of the 10 selected molecules.

Additionally, in some instances, the AI tech-bio system 106 can receive a prompt, such as "check the status of order number XYXYXYXY. If it has been delivered, schedule the compounds for dose-response phenomics profiling in [relevant cell type]" and, in response, the language machine learning model can interact with third-party tools to determine a status of an order and also interact with a tech-bio exploration tool to cause testing device(s) (e.g., within an automated lab of the tech-bio exploration system 104) to perform the dose-response phenomics profiling for the relevant cell type (for the compounds).

In addition, the AI tech-bio system 106 can receive prompts that query various layers of the bio-activity discovery pipeline and can utilize the language machine learning model (in accordance with one or more implementations herein) to execute requests with one or more tech-bio exploration tools to generate and/or obtain bio-activity data in response to the multi-layer prompts. For example, the AI tech-bio system 106 can receive prompts with multiple layers that request a target from a phenotype. As an example, the AI tech-bio system 106 can receive a sequence of prompts that request targets from a disease (e.g., "give me a list of known targets involved in asthma?"), request pathways from identified targets (e.g., "give me a list of known targets involved in DNA damage response"), request a novel target from maps of biology (e.g., "what are some novel targets involved in DNA damage response?"), and request target prioritization (e.g., "which target is the most druggable? How does Target X compare to Target Y?"). Indeed, the AI tech-bio system 106 can utilize the language machine learning model to respond to the above-mentioned layers of prompts by autonomously executing various tech-bio exploration tools in accordance with one or more implementations herein.

As another example of the AI tech-bio system 106 receiving prompts with multiple layers, the AI tech-bio system 106 can receive prompts that request a compound for a particular target. To illustrate, the AI tech-bio system 106 can receive a sequence of prompts that request known drugs from a target (e.g., "give me the list of known drugs for EGFR?"), request compounds for the target from a drug-likeness matching tool (e.g., "what are some compounds that have activity for EGFR?"), and request compounds from maps of biology for a target (e.g., "what are some compounds that show similar phenoprints as knocking down EGFR?"). Indeed, the AI tech-bio system 106 can utilize the language machine learning model to respond to the above-mentioned layers of prompts by autonomously executing various tech-bio exploration tools in accordance with one or more implementations herein.

Moreover, the AI tech-bio system 106 can also receive prompts that request a compound from a particular compound. For example, the AI tech-bio system 106 can receive prompts that request similar compounds to other compounds, such as "what are some compounds with a similar structure as compound 1?," "what are some compounds with the same scaffold as compound 1?," "are there compounds with opposite phenoprint as compound 1 in the maps of biology for cell 1?" Indeed, the AI tech-bio system 106 can utilize the language machine learning model to respond to the above-mentioned prompts by autonomously executing various tech-bio exploration tools in accordance with one or more implementations herein.

Additionally, the AI tech-bio system 106 can also receive prompts that request an action for a particular compound. For instance, the AI tech-bio system 106 can receive prompts that request molecular properties and activity from compounds, such as "what is the solubility of compound 1?" and/or "does compound 1 bind to enzyme 1?" Furthermore, the AI tech-bio system 106 can receive prompts that request targets from compounds, such as "what are the top 10 targets with similar phenoprints as compound 1?" In addition, the AI tech-bio system 106 can receive prompts that request availability and/or purchasing for particular compounds, such as "here is a list of 10 compounds, check if they are commercially available on vendor 1 and order them." Indeed, the AI tech-bio system 106 can utilize the language machine learning model to respond to (and/or take actions from) the above-mentioned prompts by autonomously executing various tech-bio exploration tools in accordance with one or more implementations herein.

As another example, the AI tech-bio system 106 can receive prompts, such as "generate X compounds for Y disease, optimized for Z properties" (e.g., where X, Y, and Z are variable inputs). The AI tech-bio system 106 can utilize the above-mentioned prompt with the language machine learning model to respond to the above-mentioned prompts by autonomously executing various tech-bio exploration tools in accordance with one or more implementations herein.

As another example, the AI tech-bio system 106 can receive a prompt, such as "propose 100 novel and not-commercially available compounds that can modulate cell morphogenesis mechanisms." In response, the language machine learning model (in accordance with one or more implementations herein) can generate a set of tasks (or execution requests) to execute (e.g., identify a target from a phenotype, identify compounds for the target, identify compounds similar to the identified compounds for the target, and determine whether the identified compounds are commercially available). Indeed, the AI tech-bio system 106 (through the language machine learning model) can execute requests to various tech-bio exploration tools (as described herein) to find targets involved in cell morphogenesis pathway, find existing drugs and/or compounds with similar phenoprints and/or compounds with activity to the target identified in the pathway, starting from the known drugs, design new compounds that have activity (e.g., scaffolds and/or similar structure to the starting points) and compute the ADMET and drug-likeness of the compounds to rank the compounds, and check if the ranked compounds are commercially available or not.

Indeed, examples of the AI tech-bio system 106 utilizing a template-based tech-bio query and free-flow text tech-bio queries to generate and/or output responses to workflows (as described above) are described in greater detail below (e.g., with reference to FIGS. 7A-7G and 8A-8L).

Figure 4:
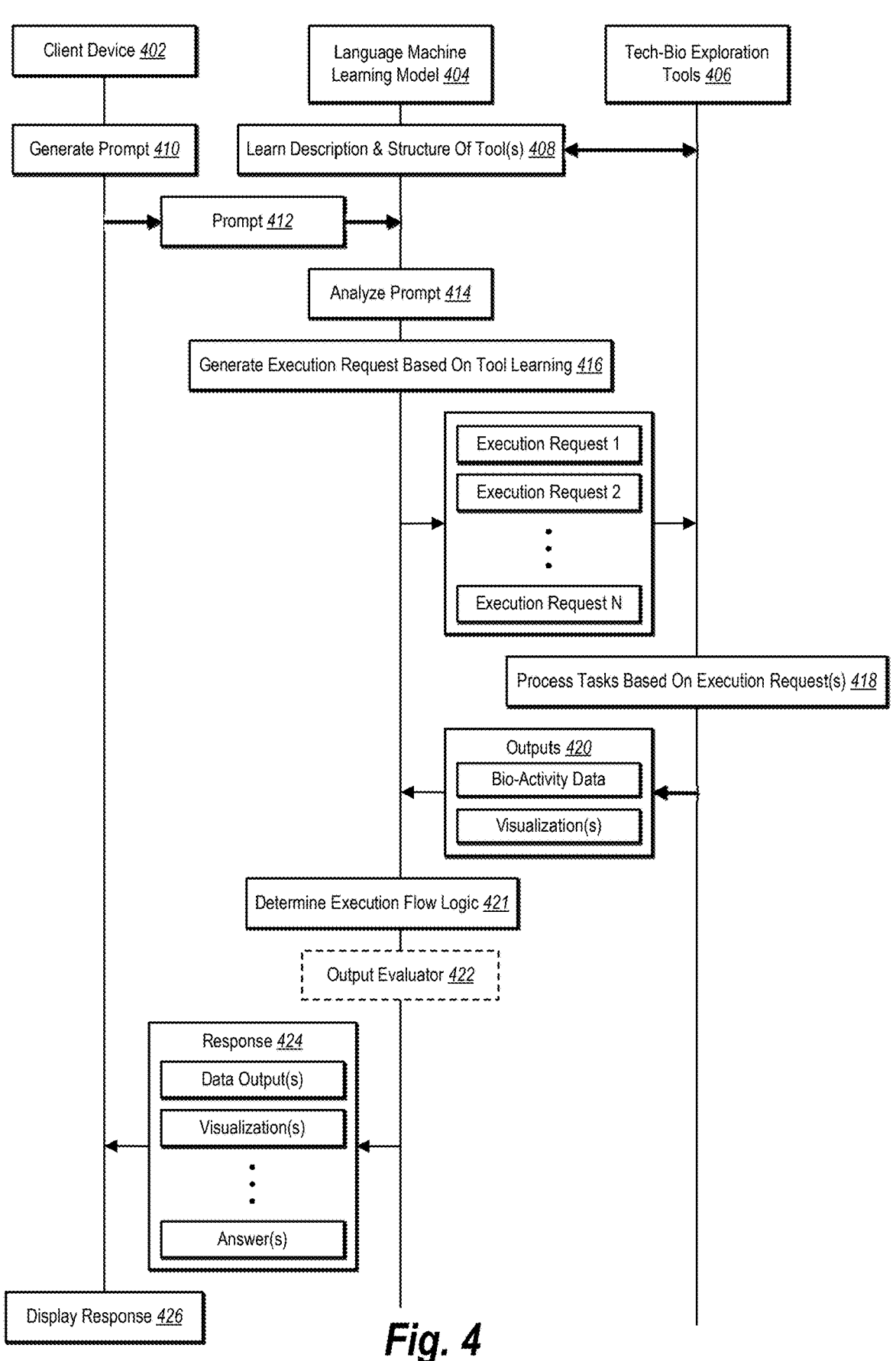
FIG. 4 illustrates a flow diagram of an AI tech-bio system utilizing a prompt for a tech-bio query with language machine learning model in accordance with one or more embodiments.

In addition, FIG. 4 illustrates a flow diagram of the AI tech-bio system 106 utilizing a prompt for a tech-bio query with language machine learning model. In particular, FIG. 4 illustrates one or more steps or acts of the AI tech-bio system 106 enabling a query prompt with a language machine learning model that interacts with one or more tech-bio exploration tools as described herein (e.g., in relation to FIG. 3).

As shown in FIG. 4, a language machine learning model 404 interacts with tech-bio exploration tools 406 to learn descriptions and/or structures of the tools (in an act 408) in accordance with one or more implementations herein. Furthermore, as shown in an act 410 of FIG. 4, the client device 402 generates a prompt (e.g., a user submitted tech-bio query as described above). Moreover, as shown in FIG. 4, the AI tech-bio system 106 provides the prompt 412 to the language machine learning model 404. In some cases, as mentioned above, the AI tech-bio system 106 analyzes the prompt 412 to append task descriptions and/or tech-bio tool descriptions (as described above) to the prompt 412 (e.g., as modified prompt with appropriate context for interacting with the various tools).

Additionally, as shown in act 414 of FIG. 4, the language machine learning model 404 analyzes the prompt (e.g., the prompt 412). Indeed, as shown in act 416, the language machine learning model 404 analyzes the prompt with a learning of the description and structure of the tech-bio exploration tools (e.g., from the act 408) to generate an execution request(s). Moreover, as shown in FIG. 4, the language machine learning model 404 provides the execution requests (e.g., execution requests 1-N) to the tech-bio exploration tools 406 to process tasks based on the execution request(s) (in an act 418). In turn, the tech-bio exploration tools 406 generate outputs 420 based on processing the execution requests (in the act 418). Indeed, as shown in FIG. 4, the outputs 420 from the tech-bio exploration tools 406 can include bio-activity data and/or visualization(s).

Moreover, as shown in FIG. 4, the language machine learning model 404 utilizes the outputs 420 to generate a response 424 for the client device 402. As shown in FIG. 4, the response 424 can include, but is not limited to, data output(s), visualization(s), and/or answer(s) generated by the language machine learning model 404 by analyzing the outputs 420 of the tech-bio exploration tools 406 (in accordance with one or more implementations herein). Then, in an act 426, the client device 402 displays the response 424 (in accordance with one or more implementations herein). For example, the language machine learning model 404 can generate the response 424 as illustrated in FIGS. 7A-7G and 8A-8L.

In addition, as shown in act 421 of FIG. 4, the language machine learning model 404 determines an execution flow logic for the prompt. In particular, the language machine learning model 404 can determine a thought, action, and/or input for the tech-bio query of the prompt. Indeed, the language machine learning model 404 (as part of the act

421) can generate a justification and/or reasoning (as the thought) for the workflow or approach determined for the prompt, determine (and/or display) one or more selected tech-bio tools to utilize as actions, and/or determine inputs utilized with the selected tech-bio tools (or in a workflow) to generate a response for the tech-bio query. Indeed, the language machine learning model 404 can determine a thought, action, and/or input (as part of the execution flow logic for the prompt) at various phases of the illustrated flow (e.g., while analyzing the prompt in the act 414, while generating the execution request, while receiving outputs 420 from the tech-bio exploration tools 406, while generating the response 424). In some implementations, the language machine learning model 404 utilizes the thought, action, and/or input generated while determining the execution flow logic (in the act 421) as part of the response 424.

In addition, the language machine learning model 404 (in the act 421) determines the execution flow logic by selecting between generating a (final) response to the tech-bio query or executing one or more additional tech-bio tools towards the response to the tech-bio query (e.g., based on thoughts, actions, or inputs generated by the language machine learning model 404). For instance, the language machine learning model 404 can determine that the outputs 420 include data that satisfies (or fulfills) the tech-bio query represented in the prompt 412 and, accordingly, the language machine learning model 404 generates the response 424 as a final response to the tech-bio query (as described below).

In one or more instances, the language machine learning model 404 determines that additional tasks are remaining to satisfy (or fulfill) the tech-bio query represented in the prompt 412. In response, the language machine learning model 404 (e.g., using thoughts, actions, or inputs) can generate (or continue to execute) one or more additional execution requests (e.g., the execution requests 1-N or additional execution request(s)) for the additional tasks. In some cases, the language machine learning model 404 can utilize the outputs 420 from one or more tech-bio exploration tools 406 (as inputs) to generate the additional execution requests for additional tech-bio exploration tools. In particular, the language machine learning model 404 can generate and/or utilize execution requests (which can include previous outputs) that build on one or more data outputs from utilized tech-bio exploration tools 406 to continuously process tasks at additional tech-bio exploration tools to satisfy (or fulfill) the tech-bio query represented in the prompt 412.

Moreover, as shown in FIG. 4, in some implementations, the language machine learning model 404 utilizes an output evaluator 422. In one or more embodiments, the AI tech-bio system 106 utilizes custom language machine learning model (or other machine learning model) evaluators trained to evaluate (or assess) scientific information. In particular, the output evaluator 422 can include a language machine learning model evaluator that evaluates a language machine learning models trajectory and/or output. For instance, the output evaluator 422 can determine whether output responses of the language machine learning model are correct (or sound).

In some cases, the language machine learning model utilizes an output evaluator 422 that is trained using expert annotations of output data from the language machine learning model (e.g., expert annotations of generated scientific information or statements). In one or more implementations, the AI tech-bio system 106 utilizes an output evaluator 422 that is trained to assess a trajectory of the language machine learning model (e.g., via the outputs 420 and/or one or more thoughts, actions, or inputs generated by the language machine learning model 404). For instance, the output evaluator 422 assesses whether a language machine learning model is correctly predicting steps (or tasks) based on an input prompt. For example, the AI tech-bio system 106 can utilize predefined trajectories for training prompts as training data. Then, the AI tech-bio system 106 trains the output evaluators to predict when the language machine learning model is utilizing a correct and/or incorrect trajectory (e.g., predicting a sequence of steps for utilizing tech-bio exploration tools) for a particular prompt. Indeed, the output evaluator 422 analyzes the tasks generated by the language machine learning model 404 for a prompt 412 and outputs a prediction to indicate the sequence of tasks as a correct and/or incorrect trajectory for the language machine learning model 404.

In some cases, the AI tech-bio system 106 utilizes output data from an output evaluator to perform various actions for the language machine learning model and/or the prompts. For instance, the AI tech-bio system 106 can utilize the output data from the output evaluator to fine tune the language machine learning model (e.g., based on correct and incorrect output determinations, correct and incorrect trajectory determinations). Furthermore, the AI tech-bio system 106 can utilize the output data from the output evaluator to fine tune and/or modify a provided prompt to improve the utilization of the language machine learning model with the prompt. Moreover, in some cases, the AI tech-bio system 106 can terminate the tasks and/or process generated by the language machine learning model based on output data from an output evaluator (e.g., terminate the process upon detecting an incorrect trajectory and/or incorrect result).

In some instances, the AI tech-bio system 106 utilizes the output evaluator 422 to analyze a tech-bio tool selection of the language machine learning model. For instance, the output evaluator 422 can analyze the tech-bio tool selected by the language machine learning model for a particular prompt to determine an accuracy (or correctness) of the selection. In some implementations, the AI tech-bio system 106 trains the output evaluator 422 by utilizing a variety of input prompts (with ground truth tech-bio tool selections or associations) as training data to teach the output evaluator 422 to detect a correct and/or incorrect tech-bio tool selection based on a prompt. For instance, the output evaluator 422 can utilize a number of varying input prompts (e.g., hundreds, thousands of prompts) for each tech-bio exploration tool to learn tech-bio query prompt to tech-bio tool associations. In some cases, the output evaluator 422 can utilize similar input prompts with varying input perturbations for each tech-bio exploration tool to learn tech-bio query prompt to tech-bio tool associations.

In one or more instances, the output evaluator 422 can utilize an expected output for a prompt as ground truth to determine an accuracy of the language machine learning model with an input training prompt. For instance, the output evaluator 422 can compare the output of the language machine learning model (e.g., a tech-bio tool selection, a response, a received output) to an expected ground truth outcome to correct and/or adjust the language machine learning model and/or indicate that the language machine learning model utilized an incorrect process (while rerunning the task). In some instances, the output evaluator 422 can compare the expected output to the actual output by utilizing a natural language comparison. Indeed, the output evaluator 422 can utilize a threshold similarity measure (e.g., a cosine similarity) to determine the similarity between the expected output to the actual output. For example, when the expected output to the actual output satisfies a threshold similarity measure, the output evaluator 422 can indicate a correct response by the language machine learning model.

In some cases, the output evaluator 422 can also analyze tech-bio tool descriptions to determine whether the tech-bio tool descriptions (e.g., tech-bio tool structures) are distinct between tech-bio tools (e.g., to enable accurate tech-bio tool selection by the language machine learning model). For instance, the output evaluator 422 can determine distinctiveness of tech-bio tool structures to enable the language machine learning model(s) to accurately select tech-bio tools (e.g., with reduced errors for variance in prompts).

Although one or more embodiments describe utilizing the output evaluator 422 to check for a correct tech-bio tool selection, the output evaluator 422 can also determine correct input data or format for the tech-bio tool (by the language machine learning model) and/or an output of the tech-bio tool. In addition, the output evaluator 422 can also identify correct usage of input data prioritization (e.g., prioritizing a compound as requested in a prompt) by the language machine learning model (in accordance with one or more implementations herein).

In addition, the output evaluator 422 can trigger notifications and/or flags for incorrect tech-bio tool selections by the language machine learning model. For example, the output evaluator 422 can indicate a low confidence tech-bio tool selection by the language machine learning model and cause the language machine learning model to display a prompt to indicate the low confidence tech-bio tool selection. In some cases, the language machine learning model can display a selectable option to request approval (or confirmation) of a tech-bio tool selection when the tech-bio tool selection is determined as incorrect by the output evaluator 422. In some cases, the output evaluator 422 can flag the incorrect tech-bio tool selection and cause the language machine learning model to update a tech-bio tool selection (e.g., execute tasks utilizing an updated tech-bio tool selection). Indeed, the output evaluator 422 can also trigger notifications and/or flags for incorrect outputs, incorrect workflows, and/or incorrect input data by the language machine learning model.

In some cases, the AI tech-bio system 106 can enable user interactions to modify a trajectory of the language machine learning model (e.g., via the outputs 420 and/or one or more thoughts, actions, or inputs generated by the language machine learning model 404). For instance, the AI tech-bio system 106 can receive, as an input prompt, user input indicating an incorrect trajectory, workflow, and/or tech-bio tool selection to cause the language machine learning model to update the trajectory, workflow, and/or tech-bio tool selection in accordance with one or more implementations herein (e.g., as described above in relation to the output evaluator). In addition, the AI tech-bio system 106 can receive, as an input prompt, user input indicating an incorrect input and/or input format for a tech-bio tool selection to cause the language machine learning model to update the incorrect input and/or input format for the tech-bio tool selection in accordance with one or more implementations herein.

Although FIG. 4 illustrates a particular number of client devices and/or prompts, in one or more embodiments, the AI tech-bio system 106 can utilize (or communicate) with a various numbers of client devices for various combinations and/or types of prompts. In addition, in one or more implementations, the AI tech-bio system 106 can utilize various numbers of and/or combinations of tech-bio exploration tools and generate a variety of outputs and/or visuals.

Furthermore, although FIGS. 3 and 4 illustrate the AI tech-bio system 106 utilizing a singular language machine learning model to generate responses to prompts from client devices (e.g., tech-bio queries), the AI tech-bio system 106 can utilize multiple language machine learning models to generate responses for a prompt from a client device. Indeed, the AI tech-bio system 106 can utilize multiple language machine learning models as described herein (e.g., in relation to FIG. 8) to generate a bio-activity data response to one or more prompt-based tech-bio queries (in accordance with one or more implementations herein).

Figure 5:
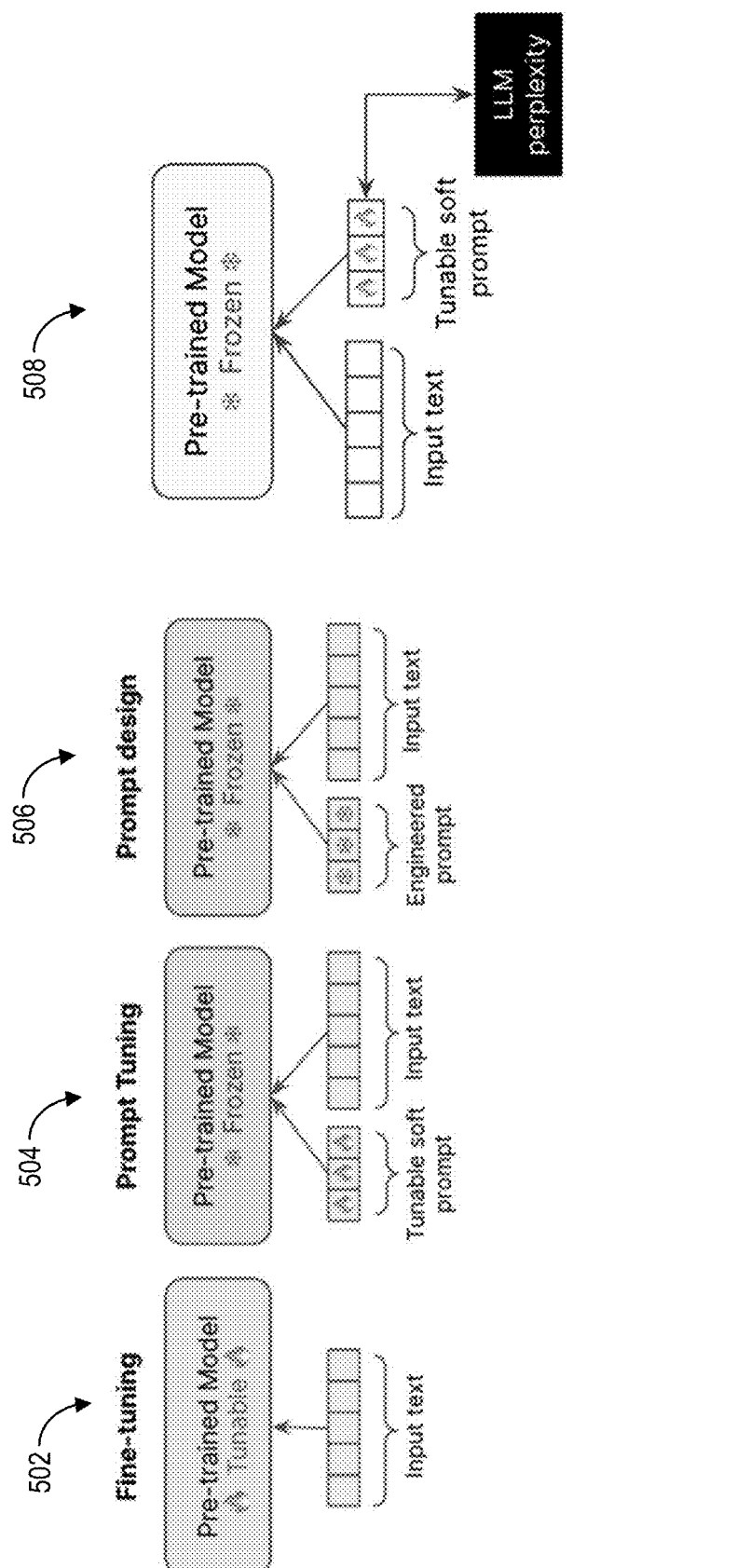
FIG. 5 illustrates an AI tech-bio system tuning language machine learning models in accordance with one or more embodiments.

In some cases, the AI tech-bio system 106 can tune language machine learning models utilizing various approaches of tunable prompts, input text, and/or engineered prompts between tunable and/or frozen pre-trained language machine learning models. For instance, FIG. 5 illustrates the AI tech-bio system 106 tuning language machine learning models. As shown in FIG. 5, the AI tech-bio system 106 can, in some cases, fine tune a language machine learning model 502 utilizing a tunable pre-trained model with input text. In particular, the AI tech-bio system 106 can utilize a pre-trained model to generate predictions from input text (e.g., predicted tools, generated calls to APIs, predicted responses, as described herein). The AI tech-bio system 106 can compare the predictions to ground truth results (e.g., a ground truth tool, known calls, or known response) utilizing a loss function. Moreover, the AI tech-bio system 106 can determine a measure of loss (utilizing the loss function) and modify parameters of the large language model (e.g., utilizing back-propagation and/or gradient descent). In this manner, the AI tech-bio system 106 can fine-tune a large language model to select tech-bio exploration tools, call tech-bio exploration tools, and generate various responses.

In some instances, as shown in FIG. 5, the AI tech-bio system 106 can prompt tune a language machine learning model 504 by utilizing a tunable soft prompt and input text with a frozen pre-trained model. For example, the AI tech-bio system 106 can improve a series of continuous embeddings (i.e., vectors) that act as "soft prompts". These embeddings are tuned to steer model behavior without changing the models internal weights/parameters. For example, the AI tech-bio system 106 can take a set of trainable embeddings as input alongside a task-specific text. The AI tech-bio system 106 can then optimize these embeddings during training (e.g., based on comparing predictions to ground truth results as described above) to achieve better performance on a given task. The AI tech-bio system 106 can also utilize other prompt tuning approaches, such as prefix tuning, instruction tuning, chain-of-thought prompting, few-shot prompting, or auto-prompting (e.g., reinforcement learning or gradient-based techniques to modify prompts). In one or more instances, the language machine learning model 502 and the language machine learning model 504 often result in strong performance but with low interpretability.

Furthermore, as shown in FIG. 5, the AI tech-bio system 106 can prompt design with a language machine learning model 506 by utilizing an engineered prompts (e.g., template prompts, non-tunable prompts) and input text with a frozen pre-trained model. For instance, the AI tech-bio system 106 can utilize an engineered prompt and modify placeholders within a template to design a final prompt based on any particular input from a client device. In some instances, the language machine learning model 506 and the language machine learning model 504 result in efficient multitasking models.

As also shown in FIG. 5, the AI tech-bio system 106 can tune a language machine learning model 508 utilizing input text and a tunable soft prompt that accounts for language machine learning perplexity (with a frozen pre-trained model). Indeed, in one or more instances, the language machine learning model 508 results in improved performance, improved interpretability, and improved multitasking capabilities.

As mentioned above, the AI tech-bio system 106 can utilize one or more language machine learning models as autonomous agents to automatically execute a variety of tasks within a bio-activity discovery pipeline to identify and/or generate various bio-activity data via tech-bio exploration tools. For instance, FIG. 6 illustrates the AI tech-bio system 106 facilitating a language machine learning model in an autonomous process to automatically execute various processes, via tech-bio exploration tools, to generate a variety of bio-activity data for the tech-bio exploration system 104.

As mentioned above, the AI tech-bio system 106 can generate and/or obtain bio-activity data utilizing a language machine learning model with one or more tech-bio tools using a user selected tech-bio query prompt template from a set of tech-bio query prompt templates. For example, FIGS. 6A and 6B illustrate the AI tech-bio system 106 utilizing tech-bio query prompt template selection with a language machine learning model to execute one or more tech-bio exploration tools for a tech-bio query.

Figure 6A:
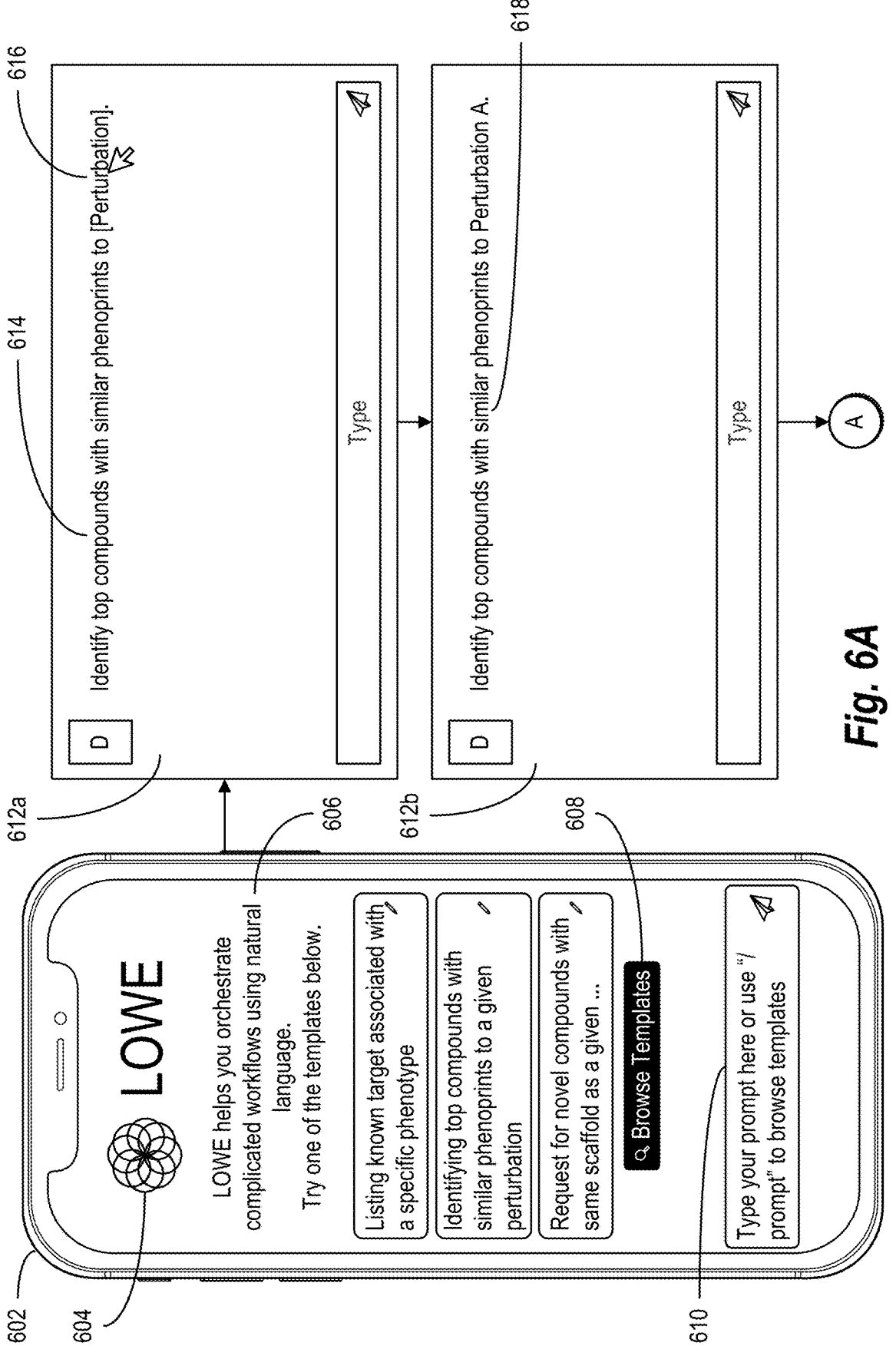

As shown in FIG. 6A, the AI tech-bio system 106 provides, for display within a graphical user interface 604 of a client device 602, a tech-bio prompt selector 606. As shown in FIG. 6A, the AI tech-bio system 106 displays the tech-bio prompt selector 606 with multiple selectable tech-bio query templates. In addition, as shown in FIG. 6A, the AI tech-bio system 106 also displays a selectable option 608 to enable navigation to additional selectable tech-bio query templates (e.g., by expanding the tech-bio prompt selector 606 to display additional selectable tech-bio query templates and/or navigating to a menu of multiple selectable tech-bio query templates). In addition, as shown in FIG. 6A, the AI tech-bio system 106 also displays a text input element 610 to enable user input to search for one or more selectable tech-bio query templates (e.g., by suggesting or recommending tech-bio query templates based on user text input and/or displaying one or more selectable tech-bio query templates based on user text input commands or shortcuts).

Furthermore, as shown in FIG. 6A, the AI tech-bio system 106 receives a selection, via a user interaction, of a selectable tech-bio query template from the tech-bio prompt selector 606. In response, as shown in FIG. 6A, the AI tech-bio system 106 provides, for display within a graphical user interface 612a, a query interface (e.g., a chat interface) between a user of the client device 602 and a language machine learning model of the AI tech-bio system 106. Indeed, as shown in FIG. 6A, the AI tech-bio system 106 displays a selected tech-bio query template prompt 614 within the graphical user interface 612a (e.g., selected from the tech-bio prompt selector 606). In addition, as illustrated in FIG. 6A, the AI tech-bio system 106 also displays a perturbation input element 616 to enable an input (or selection) of a perturbation (or other input for the tech-bio query) from the user of the client device 602. As further shown in FIG. 6A, the AI tech-bio system 106, upon receiving an input of a perturbation within the perturbation input element 616, displays, graphical user interface 612b, a tech-bio query template prompt 618 with the input perturbation.

Figure 6B:
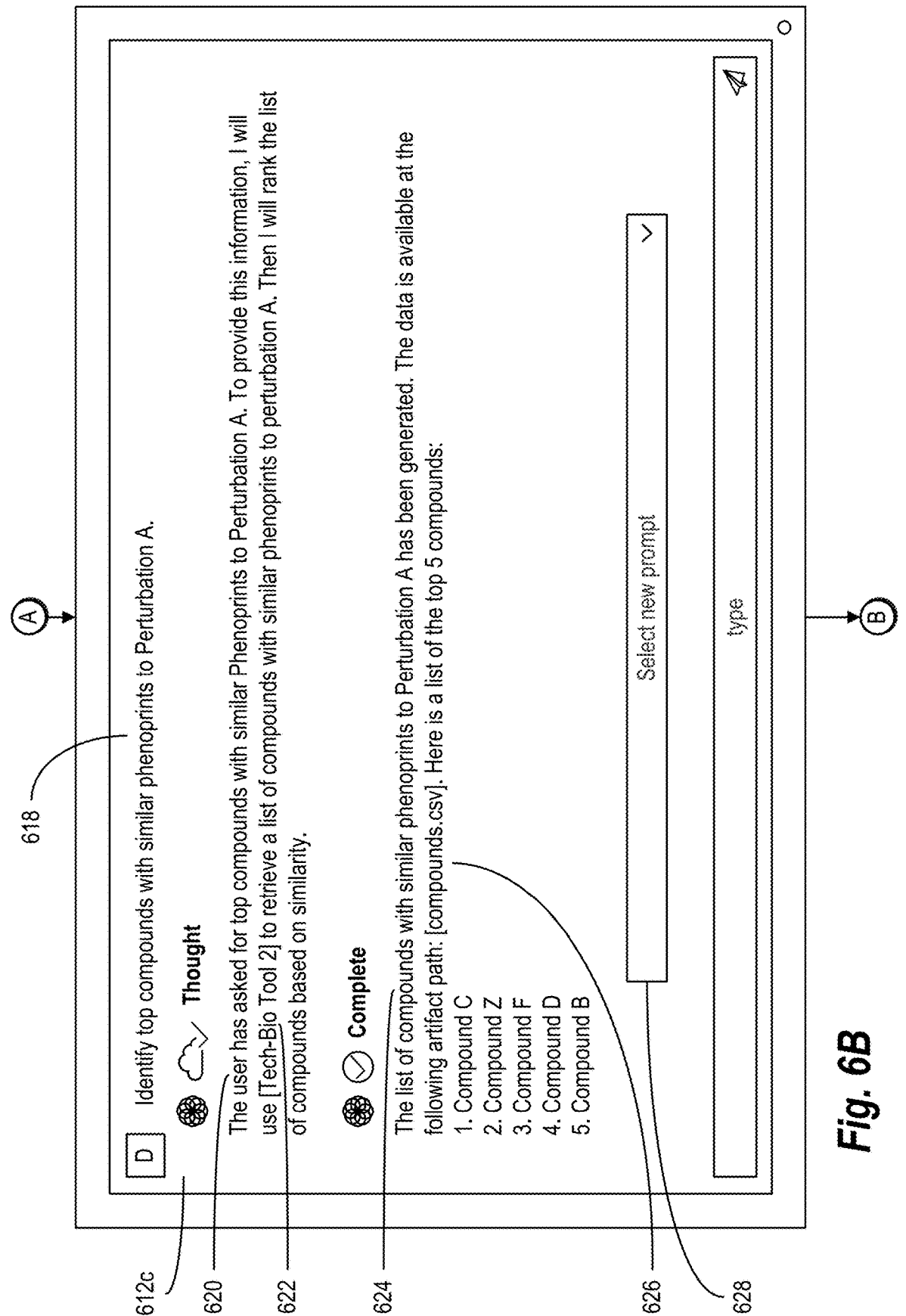

Furthermore, as shown in the transition from FIG. 6A to FIG. 6B, the AI tech-bio system 106 utilizes the tech-bio prompt 618 (e.g., a tech-bio template with an input perturbation) with a language machine learning model. Indeed, as shown in FIG. 6B, the AI tech-bio system 106, utilize the language machine learning model with the tech-bio prompt 618 to generate (and display within a graphical user interface 612c) a prompt 620 (or displayable execution request) that analyzes and generates a workflow (e.g., via selecting tech-bio tools as described herein, generating execution requests as described herein, and/or thoughts, inputs, and/or actions as described herein) for the tech-bio prompt 618. In addition, as shown in FIG. 6B, the AI tech-bio system 106, utilizing the language machine learning model, also determines and displays a tech-bio tool 622 utilized (e.g., tech-bio tool 2) to accomplish (or execute) the tasks determined for the tech-bio prompt 618 (e.g., a tool that retrieves compounds with similar phenoprints as an input perturbation).

In addition, the AI tech-bio system 106, utilizing the language machine learning model, can cause the tech-bio tool to execute one or more tasks based on input perturbations and receive output data from the executed tech-bio tool (e.g., tech-bio tool 2). Moreover, as shown in FIG. 6B, the AI tech-bio system 106, utilizing the language machine learning model, can generate, for display, a response 624 that indicates output data from the executed tech-bio tool while also formatting the tech-bio tool output data to address the prompt 620 (e.g., ranking and listing a top 5 compounds from the tech-bio tool output data). As further shown in FIG. 6B, the AI tech-bio system 106, utilizing the language machine learning model, also generates, for display, a link or reference to an artifact 626 generated for the output data of the tech-bio tool. In particular, the AI tech-bio system 106 generates the artifact 626 to provide a full set of output data from the tech-bio tool (e.g., a CSV file).

Moreover, as shown in FIG. 6B, the AI tech-bio system 106 also, utilizing the language machine learning model, displays a tech-bio prompt selector 628 (e.g., after generating and providing the response 624 for the prompt 620). Upon detecting a user interaction with the tech-bio prompt selector 628, as shown in the transition from FIG. 6B to FIG. 6C, the AI tech-bio system 106 displays, within a graphical user interface 612d, additional selectable tech-bio query templates 630 via the tech-bio prompt selector 628. Indeed, as shown in FIG. 6C, the additional selectable tech-bio query templates 630 include tech-bio query templates that expand on (or build on) the response 624 (and/or the previous prompt 620). For instance, as shown in FIG. 6C, the AI tech-bio system 106, via the language machine learning model, generates selectable tech-bio query templates 630 by utilizing context from the response 624 and/or the previous prompt 620 (e.g., selected input perturbations, output compounds from a tech-bio tool, or other output data from the tech-bio tool(s)).

In addition, as shown in FIG. 6C, the AI tech-bio system 106 receives a selection, via a user interaction of a selectable tech-bio query template from the additional selectable tech-bio query templates 630 via the tech-bio prompt selector 628. In response, as shown in FIG. 6C, the AI tech-bio system 106 provides, for display within a graphical user interface 612e, a selected tech-bio query template prompt 632 (e.g., selected from the tech-bio prompt selector 628). Furthermore, as shown in FIG. 6C, the AI tech-bio system 106 displays, utilizing the language machine learning model, the tech-bio query template prompt 632 with context from the response 624 (e.g., an input perturbation and referencing compounds from the response 624). Indeed, as shown in FIG. 6C, the AI tech-bio system 106, utilizing the language machine learning model, generates and displays a prompt 634 (or displayable execution request) that analyzes and generates a workflow (e.g., via selecting tech-bio tools as described herein, generating execution requests as described herein, and/or thoughts, inputs, and/or actions as described herein) for the tech-bio query template prompt 632. Moreover, the AI tech-bio system 106, utilizing the language machine learning model, generates the prompt 634 utilizing context from the previous prompt 620 and the response 624 (e.g., a list of compounds and the input perturbation). Indeed, as shown in FIG. 6C, the AI tech-bio system 106, utilizing the language machine learning model, also determines and displays a tech-bio tool utilized (e.g., tech-bio tool 13) to accomplish (or execute) the tasks determined for the tech-bio query template prompt 632 (e.g., a tool that identifies molecular pair series for compounds identified in the previous executed query for the input perturbation).

Moreover, the AI tech-bio system 106, utilizing the language machine learning model, can cause the tech-bio tool (e.g., tech-bio tool 13) to execute one or more tasks based on the input data created from the context of the previous prompt 620 and the response 624 (e.g., a list of compounds and the input perturbation) and receive output data from the executed tech-bio tool (e.g., tech-bio tool 13). Additionally, as shown in FIG. 6C, the AI tech-bio system 106, utilizing the language machine learning model, can generate, for display, a response 636 that indicates output data from the executed tech-bio tool (e.g., to address the request in the prompt 634). Indeed, as shown in FIG. 6C, the AI tech-bio system 106 provides, for display, a link or reference to an artifact (e.g., a CSV file) generated for the output data of the tech-bio tool for the prompt 634 in the response 636.

In addition, as shown in FIG. 6C, the AI tech-bio system 106 also, utilizing the language machine learning model, displays a tech-bio prompt selector 638 (e.g., after generating and providing the response 636 for the prompt 634). Indeed, the AI tech-bio system 106 can identify additional user interactions with the tech-bio prompt selector 638 to execute one or more additional tasks via the language machine learning model (in accordance with one or more implementations herein). In particular, the AI tech-bio system 106, via the language machine learning model, can utilize additional selected tech-bio query templates from the tech-bio prompt selector 638 to generate tech-bio queries that expand on (or build on) the one or more responses (and/or the previous prompts) generated in the query interface (via the language machine learning model).

As mentioned above, in one or more implementations, the AI tech-bio system 106 displays a tech-bio query prompt selector. Indeed, the AI tech-bio system 106 can display various types of tech-bio query prompt selectors. For example, the AI tech-bio system 106 can display a dropdown menu with selectable tech-bio query prompt templates as a tech-bio query prompt selector. Additionally, the AI tech-bio system 106 can display a menu of selectable user interface elements (for the selectable tech-bio query prompt templates) as the tech-bio query prompt selector. In some cases, the AI tech-bio system 106 can enable text input into a text input user interface element to search for selectable tech-bio query prompt templates (similar to the input text query from the user) to display search results as a tech-bio query prompt selector.

Moreover, in one or more instances, the AI tech-bio system 106 enables the display and selection of additional selectable tech-bio query prompt templates (e.g., the additional selectable tech-bio query prompt templates 630). In one or more instances, the AI tech-bio system 106 (via the language machine learning model) displays additional selectable tech-bio query templates that relate to a previous tech-bio query template and/or previous response generated by the AI tech-bio system 106 (in accordance with one or more implementations herein). For instance, the AI tech-bio system 106 can display additional selectable tech-bio query templates that build or continue a workflow of a previous tech-bio query template and/or previous response generated by the AI tech-bio system 106 (e.g., as shown in FIGS. 7A-7G). Moreover, in some implementations, the AI tech-bio system 106 can display additional selectable tech-bio query templates that are unrelated to previous tech-bio query templates and/or previous responses (e.g., to initiate a new workflow and/or tech-bio query).

Furthermore, as mentioned above, the AI tech-bio system 106 can receive an input perturbation (or a perturbation selection). For instance, the AI tech-bio system 106 can receive an input perturbation as an input in a tech-bio query prompt template (e.g., as an object of interest in the tech-bio query). In some cases, the AI tech-bio system 106 receives the input perturbation via text input (e.g., within the tech-bio query prompt template, a dropdown menu with selectable perturbations, and/or a search function that enables users to search through a dataset of perturbations).

As used herein, the term "perturbation" (e.g., cell perturbation) refers to an alteration or disruption to a cell or the cell's environment (to elicit potential phenotypic changes to the cell). In particular, the term perturbation can include a gene perturbation (i.e., a gene-knockout perturbation) or a compound perturbation (e.g., a molecule perturbation or a soluble factor perturbation). These perturbations are accomplished by performing a perturbation experiment. A perturbation experiment refers to a process for applying a perturbation to a cell. A perturbation experiment also includes a process for developing/growing the perturbed cell into a resulting phenotype. Indeed, in one or more instances, a perturbation can include a perturbant that causes the alteration or disruption to a cell or the cell's environment. For example, a perturbation can include a particular molecule, gene, protein, or other soluble factor utilized to cause a cell perturbation.

For example, a gene perturbation can include gene-knockout perturbations (performed through a gene knockout experiment). For instance, a gene perturbation includes a gene-knockout in which a gene (or set of genes) is inactivated or suppressed in the cell (e.g., by CRISPR-Cas9 editing).

Moreover, a compound perturbation can include a cell perturbation using a molecule and/or soluble factor. For instance, a compound perturbation can include reagent profiling such as applying a small molecule (e.g., pharmaceutical drug) to a cell and/or adding soluble factors to the cell environment. Additionally, a compound perturbation can include a cell perturbation utilizing the compound or soluble factor at a specified concentration. Indeed, compound perturbations performed with differing concentrations of the same molecule/soluble factor can constitute separate compound perturbations. A soluble factor perturbation is a compound perturbation that includes modifying the extracellular environment of a cell to include or exclude one or more soluble factors. Additionally, soluble factor perturbations can include exposing cells to soluble factors for a specified duration wherein perturbations using the same soluble factors for differing durations can constitute separate compound perturbations.

Although one or more embodiments herein illustrate the AI tech-bio system 106 receiving an input perturbation, the AI tech-bio system 106 (via the language machine learning model) can receive various types of inputs to process the inputs in accordance with one or more implementations herein. For example, the AI tech-bio system 106 can utilize inputs, such as, but not limited to, experiment design identifiers, phenomic image identifiers, mechanisms of action, tech-bio exploration tool identifiers. In some cases, the AI tech-bio system 106 can also utilize inputs, such as, parameters for tech-bio exploration tools (e.g., thresholds, iterations, dataset size, output size).

Moreover, in one or more instances, the AI tech-bio system 106 (via the language machine learning model) can utilize context from previous tech-bio query prompts and/or previous tech-bio responses in subsequent execution requests. For example, the AI tech-bio system 106, upon receiving an additional tech-bio query prompt (or tech-bio query prompt template selection), can utilize context from previous tech-bio responses (e.g., tech-bio exploration tool outputs, data responses generated by the language machine learning model). Additionally, in one or more implementations, the AI tech-bio system 106, upon receiving an additional tech-bio query prompt (or tech-bio query prompt template selection), can utilize context from previous tech-bio prompts, such as, but not limited to, input perturbations, input requests (e.g., requests to rank, requests to filter), and/or input parameters (e.g., data output size settings, ranking size settings, filtering size settings, filter parameters).

Additionally, in one or more instances, the AI tech-bio system 106 (via the language machine learning model) can generate modified prompts (or displayable execution requests) that include thoughts, actions, and/or inputs indicating multiple tech-bio exploration tools. For instance, the AI tech-bio system 106 (via the language machine learning model) can generate a prompt to describe a workflow of the process utilized to accomplish one or more tasks for the tech-bio query (e.g., from the tech-bio query prompt template and/or free-form text tech-bio query prompt). For example, the AI tech-bio system 106 can generate a prompt to describe a workflow of the process utilized to accomplish one or more tasks for the tech-bio query via one or more tech-bio exploration tools as described and illustrated in FIGS. 7A-7G and 8A-8L.

Additionally, the AI tech-bio system 106 (via the language machine learning model) can execute multiple tasks, through one or more tech-bio tools, within a workflow determined by the language machine learning model (e.g., multiple thoughts, actions, and/or inputs). Indeed, the AI tech-bio system 106 can execute multiple tasks, through one or more tech-bio tools, within a workflow determined by the language machine learning model prior to enabling additional tech-bio query prompt selections (or input of free-form text tech-bio query prompt selections). For instance, the AI tech-bio system 106 (via the language machine learning model) can execute multiple tasks as described and illustrated in FIGS. 7A-7G and 8A-8L.

Figure 7A:
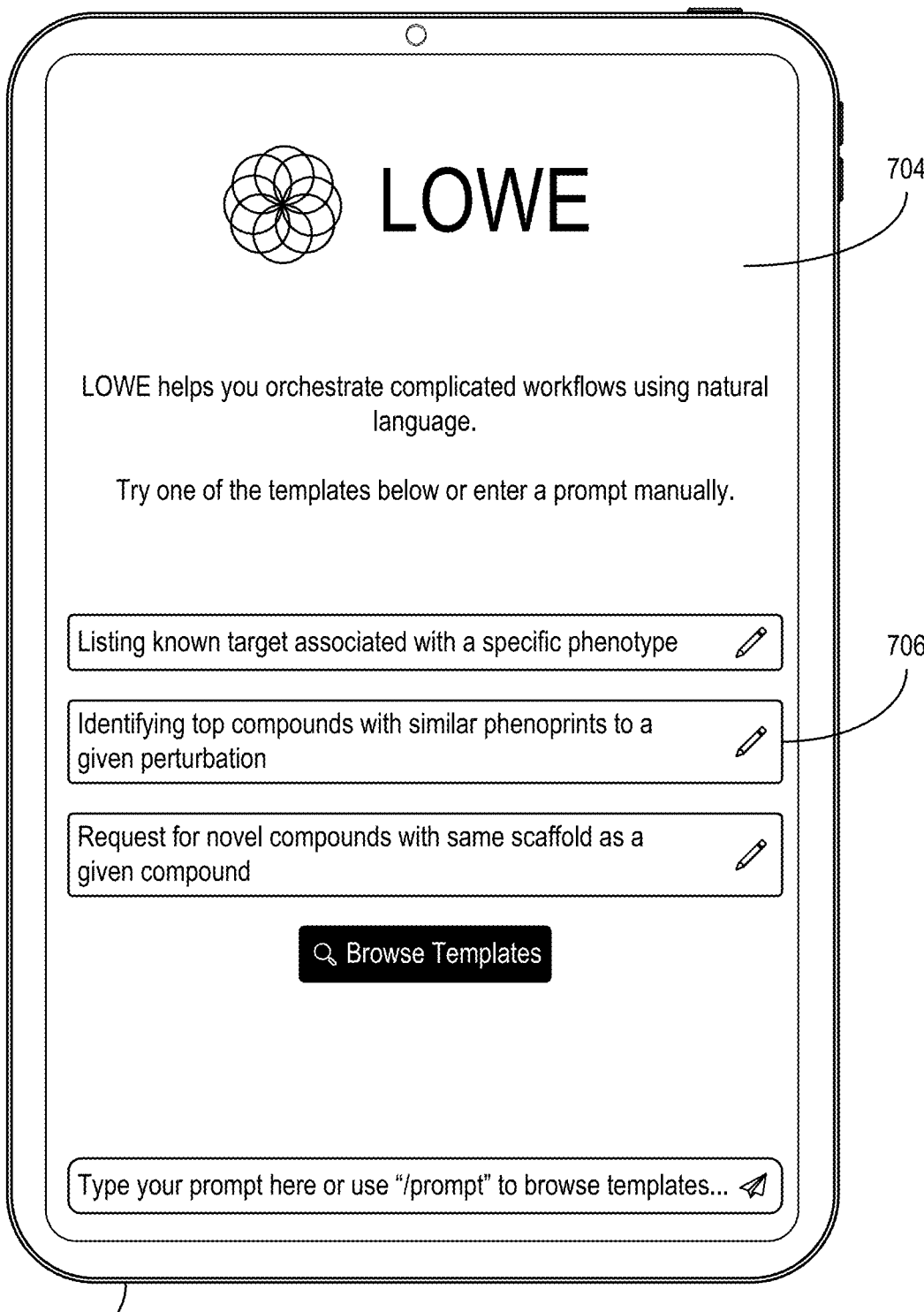
Figure 7B:
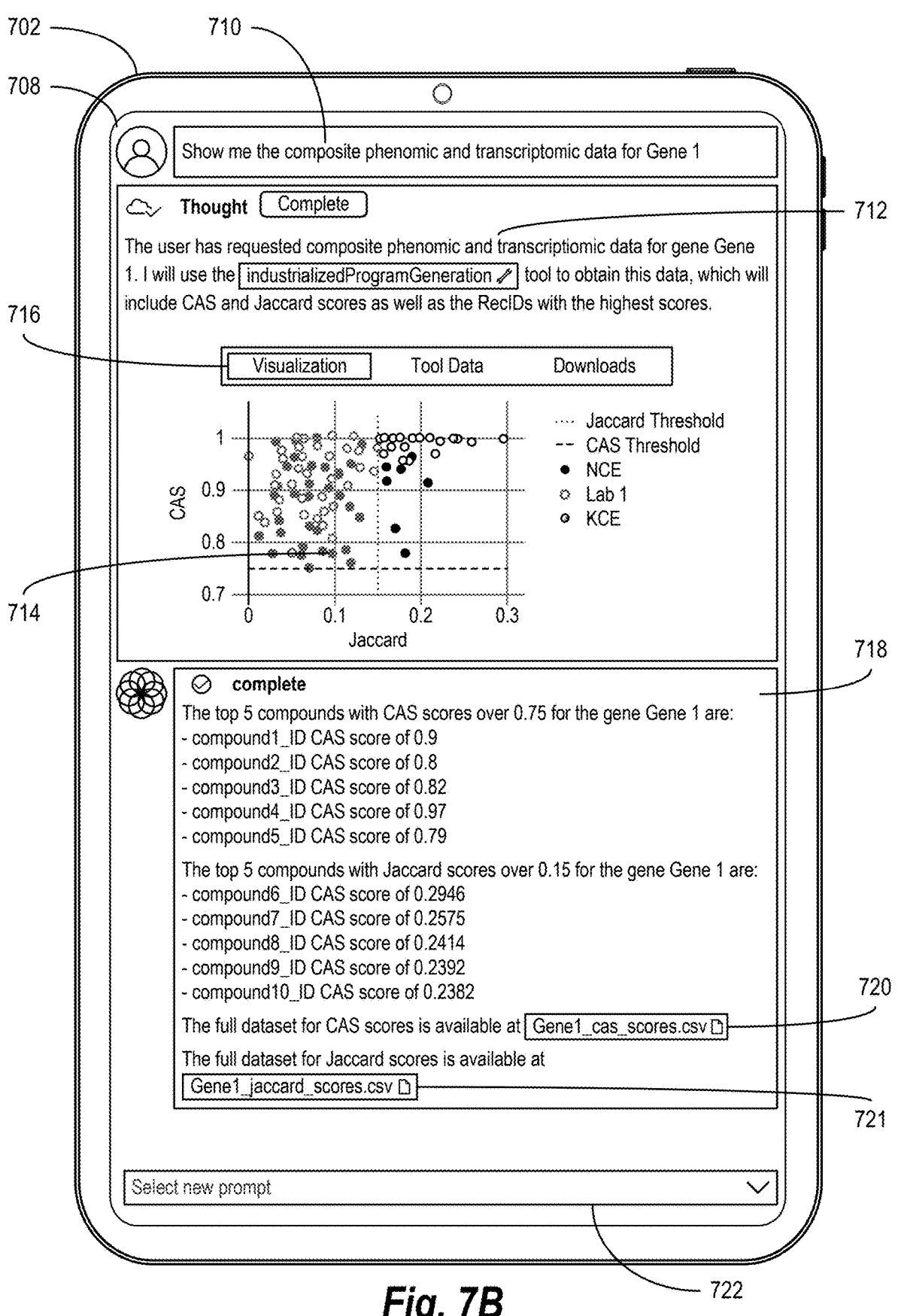

For example, FIGS. 7A-7G illustrate an example of the AI tech-bio system 106 providing an interactive query prompt interface with a tech-bio prompt selector having tech-bio query prompt templates to execute one or more tech-bio exploration tools for a tech-bio query output response. For example, as shown in FIG. 7A, the AI tech-bio system 106 provides, for display within a graphical user interface 704 of a client device 702, a tech-bio prompt selector 706 having tech-bio query prompt templates. Furthermore, as shown in the transition between FIGS. 7A and 7B, the AI tech-bio system 106, upon receiving a selection of a tech-bio query prompt template (e.g., a compound-gene activity query prompt template) from the tech-bio prompt selector 706, provides, for display within the graphical user interface 704, a tech-bio query prompt 710 with an input perturbation (e.g., Gene1). Indeed, as shown in FIG. 7B, the compound-gene activity query prompt template includes a tech-bio query requesting composite phenomic and/or transcriptomic data for an input perturbation.

Indeed, in accordance with one or more implementations herein, the AI tech-bio system 106 utilizes the language machine learning model to generate a modified prompt 712 (as a displayable execution request) for the tech-bio query prompt 710. As shown in FIG. 7B, the modified prompt 712 indicates a selected tech-bio tool (e.g., a compound-gene activity modeling tool) and a workflow to process the compound-gene activity tech-bio query from the compound-gene activity query prompt template. For instance, the AI tech-bio system 106, utilizing the language machine learning model in accordance with one or more implementations herein, causes the compound-gene activity modeling tool with the input perturbation (e.g., Gene1) to generate perturbation activity scores between the input perturbation and the compounds (e.g., CAS scores and/or Jaccard scores) for compounds (e.g., to indicate compound-gene activity between the input perturbation and various compounds).

For example, as shown in FIG. 7B, the AI tech-bio system 106, utilizing the language machine learning model, generates (from output of the compound-gene activity modeling tool) visualizations 714 (for display). In particular, the visualizations 714 display a chart of perturbation activity score data and perturbation activity score thresholds for a variety of compounds (e.g., using various samplings, such as novel chemical entities (NCE), known chemical entities (KCE), and/or lab specific chemical entities). In some instances, the AI tech-bio system 106 displays the visualization 714 as an interactive chart that, upon detecting a hover action over a compound data point, displays a compound identifier and Jaccard/CAS values for the compound. In addition, as shown in FIG. 7B, the AI tech-bio system 106, via the language machine learning model, generates multiple outputs via varying visualization formats, tech-bio tool data or structure information, and/or artifacts and, further, displays an interactive user interface element 716 to navigate between the generated data for the outputs of the compound-gene activity modeling tool.

Furthermore, as shown in FIG. 7B, the AI tech-bio system 106, via the language machine learning model, also generates a response 718 from the data obtained via the compound-gene activity modeling tool. For example, the AI tech-bio system 106, utilizing the language machine learning model, generates a response in a format as described in the prompt 712 (e.g., an execution workflow of the language machine learning model). For instance, as shown in FIG. 7B, the AI tech-bio system 106, utilizing the language machine learning model, generates and displays the response 718 which identifies compounds from the data output of the compound-gene activity modeling tool to identify compounds that have perturbation activity scores between the input perturbation and the compounds that satisfy a threshold perturbation activity score(s). In addition, as shown in FIG. 7B, the AI tech-bio system 106, utilizing the language machine learning model, generates (as part of the response 718, links 720, 721 for an artifact that includes output data of the compound-gene activity modeling tool (e.g., a CSV file having the perturbation activity score data between the input perturbation and various compounds).

In one or more implementations, the AI tech-bio system 106 (via the language machine learning model) causes a compound-gene activity modeling tool to generate one or more perturbation activity scores (to identify compounds for a perturbation). For instance, the AI tech-bio system 106 can cause the compound-gene activity modeling tool to generate a compound activity score (CAS) and/or a Jaccard score.

To illustrate, in one or more instances, the compound-gene activity modeling tool can identify perturbation-compound activity signals (e.g., gene-compound activity signals) through phenomics data (e.g., phenomic validation data). For example, the compound-gene activity modeling tool generates a CAS score that estimates the likelihood of an anomalous gene-compound interaction being more significant (statistically significant) than background noise. Indeed, the compound-gene activity modeling tool can solve a rare outlier problem associated with drug discovery (e.g., using existing medicines as examples while at the same time not over-fitting models that can identify novel treatments).

For example, the compound-gene activity modeling tool generates CAS scores utilizing a two stage process. In particular, the compound-gene activity modeling tool can generate multiple pairwise gene-compound features from phenomics data (e.g., phenomic validation data) and utilize the features to train a predictive machine learning model to identify (or select) which features are related to (or most essential) for predicting gene-compound interactions. Moreover, in the second phase, the compound-gene activity modeling tool can utilize the selected features to build an anomaly detection model for one or more genes. Indeed, the compound-gene activity modeling tool can threshold the unsupervised anomaly detection model by sampling (e.g., random sampling) known and novel chemical entities (KCEs and NCEs) from data of the tech-bio exploration system. In some instances, the compound-gene activity modeling tool trains the anomaly detection model on an empirical null distribution representing the noise range for inactive compounds which is then used to predict the probability that test compounds are outliers from that noise distribution.

In response to fitting the anomaly detection model, the compound-gene activity modeling tool can utilize the anomaly detection model on a per-gene basis to estimate the likelihood of any given compound being an anomaly. For instance, in some cases, the compound-gene activity modeling tool can utilize a maximum of rolling averages of pairwise interactions (e.g., rolling window averages) between a gen and a compound over several doses as CAS features (as input to the anomaly detection model). In some cases, the compound-gene activity modeling tool can utilize a max value for the pairwise interaction measure from three rolling window averages for cosine similarity, projection, and delta ratio.

In some cases, the compound-gene activity modeling tool can train classifiers on a curated set of KCEs with target annotations, coupled with sampling (e.g., randomly sampling) annotation-free KCEs. Indeed, in one or more instances, the compound-gene activity modeling tool utilized the trained classifiers to inform feature selection for CAS scores to identify likely active NCEs. For example, in one or more implementations, the AI tech-bio system 106 utilizes the approach described in application Ser. No. 18/887,587 to generate the CAS scores.

In one or more implementations, the compound-gene activity modeling tool generates CAS scores that represent indicate a probability or confidence of a gene-compound interaction. For instance, the compound-gene activity modeling tool can utilize a CAS threshold (e.g., 0.75, 0.8, 0.85) to identify confirmations of positive gene-compound interactions. Indeed, the compound-gene activity modeling tool can utilize a measure of true positive rates (TPR) and false positive rates (FPR) at different CAS probability thresholds. In some instances, the compound-gene activity modeling tool generates CAS scores that retain information regarding effect magnitude, address issues related to usage of sigmoid fits for assessing response in high-dimensional cellular assays, and enhance feasibility of identifying potential outliers. In some cases, the compound-gene activity modeling tool filters based on compound concentration to generate consistent CAS scores (e.g., utilizing compound concentrations that satisfy a threshold concentration).

In some instances, the compound-gene activity modeling tool can generate CAS scores for a group of compounds from a matched molecular pair series (e.g., for grouped compounds that differ by a threshold number of chemical transformations). In some implementations, the compound-gene activity modeling tool can utilize the CAS scores from group of compounds from a matched molecular pair series to identify whether compounds having a CAS score that satisfies a threshold CAS score also share chemical properties (e.g., from the matched molecular pair series).

Additionally, in some cases, the compound-gene activity modeling tool determines a Jaccard score. For example, the compound-gene activity modeling tool can assess (or screen) compounds (or a subset of compounds) and genes through a transcriptomics assay of the tech-bio exploration system. Indeed, in one or more instances, the compound-gene activity modeling tool utilizes outputs from the transcriptomics assay as a DEG Jaccard score. In some implementations, the compound-gene activity modeling tool can screen compounds through a transcriptomics assay by utilizing a transcript relation model that relates transcriptomic profiles to different perturbation classes. Indeed, the compound-gene activity modeling tool can utilize a transcriptomics assay that is generated from transcriptomic embeddings for each perturbation class. Moreover, the compound-gene activity modeling tool can utilize a transcript relation model to determine relationships between the perturbation classes using the transcriptomic embeddings (e.g., to determine a relationship between the transcriptomic embedding of the compound perturbation and/or the gene perturbation). For example, the AI tech-bio system 106 can utilize a transcriptomics assay as described in UTILIZING MACHINE LEARNING AND DIGITAL EMBEDDING PROCESSES TO GENERATE DIGITAL MAPS OF BIOLOGY AND USER INTERFACES FOR EVALUATING MAP EFFICIENCY, U.S. patent application Ser. No. 18/392,989, filed Dec. 21, 2023, which is incorporated herein by reference in its entirety.

Indeed, in one or more instances, the DEG Jaccard score represents a metric computed by finding genes that significantly change between "healthy" and "disease" conditions. For example, the compound-gene activity modeling tool can perform a comparison for each compound screening via the transcriptomics assay. Moreover, the compound-gene activity modeling tool can utilize a size overlap between the compound DEGs and "disease" DEGs in comparison to the size of all DEGs in either the compound or "disease" (e.g., via division) to generate the Jaccard scores. For example, the compound-gene activity modeling tool can generate the DEG Jaccard score utilizing the ratio of the intersection to the union of origin and/or compound DEG sets and origin and/or target DEG sets.

In some cases, the compound-gene activity modeling tool determines a subset of compounds that satisfy a CAS threshold and screens the subset of compounds through the transcriptomics assay to generate Jaccard scores (as described above). In some instances, the compound-gene activity modeling tool (or language machine learning model) identifies compounds that satisfy both a CAS threshold and a Jaccard threshold (e.g., 0.1, 0.15, 0.2) (as shown in the upper quadrant of the visualization 714) as compound hits for the input perturbation (e.g., Gene1).

Moreover, as shown in FIG. 7B, the AI tech-bio system 106 also, utilizing the language machine learning model, displays a tech-bio prompt selector 722 (e.g., after generating and providing the response 718 for the prompt 712). Indeed, as illustrated in the transition between FIGS. 7B and 7C, upon detecting a user interaction with the tech-bio prompt selector 722, the AI tech-bio system 106 displays, within the graphical user interface 708, a bio query prompt 724 (e.g., a molecular pair series prompt template) (e.g., with an input perturbation Gene1 as identified in the previous response). Indeed, as shown in FIG. 7C, the molecular pair series prompt template includes a tech-bio query requesting matched molecular pair series for compounds identified for the selected (input) perturbation (e.g., based on perturbation activity scores).

Additionally, as shown in FIG. 7C, the AI tech-bio system 106 utilizes the language machine learning model to generate a modified prompt 726 (as a displayable execution request) for the tech-bio query prompt 724 (in accordance with one or more implementations herein). As shown in FIG. 7C, the modified prompt 726 indicates a selected tech-bio tool (e.g., a molecular pair series assignment tool) and a workflow to process the molecular pair series tech-bio query from the molecular pair series prompt template. In particular, FIG. 7C illustrates the AI tech-bio system 106, utilizing the language machine learning model (in accordance with one or more implementations herein), causes the molecular pair series assignment tool with the input perturbation (e.g., Gene1) and compounds for the input perturbation to generate matched molecular pair series from compound groupings of the compounds (e.g., based on a network graph).

Indeed, as further shown in FIG. 7C, the AI tech-bio system 106, utilizing the language machine learning model, generates (from output of the molecular pair series assignment tool) visualizations 728 (for display). Indeed, as shown in FIG. 7C, the AI tech-bio system 106 generates a visualization 728 to display a clustering of matched molecular pair series (e.g., an interactive 3D UMAP that represents different clusters and individual compound data points that indicate compound identifiers, CAS values, and/or cluster numbers upon hovering or interacting with the compound data points). Additionally, as illustrated in FIG. 7C, the AI tech-bio system 106, via the language machine learning model, generates multiple outputs via varying visualization formats, tech-bio tool data or structure information, and/or artifacts with selectable options to navigate between the generated data for the outputs of the molecular pair series assignment tool. In addition, as shown in FIG. 7C, the AI tech-bio system 106, via the language machine learning model, also generates a response 730 from the data obtained via the molecular pair series assignment tool. For instance, as shown in FIG. 7C, the AI tech-bio system 106, via the language machine learning model, generates and displays the response 730 which indicates a link to artifacts for the matched molecular pair data (e.g., via a CSV file) and also highlights information from the matched molecular pair output data.

In one or more embodiments, the AI tech-bio system 106 (via the language machine learning model) causes a molecular pair series assignment tool to determine one or more molecular pair series from compounds associated with a perturbation. For example, the molecular pair series assignment tool can group compounds that differ by a single chemical transformation or fragment. In some cases, the molecular pair series assignment tool utilizes a matched molecular pair analysis to identify matched molecular pairs as described in Andrew Dalke et al., MMPDB: An Open-Source Matched Molecular Pair Platform for Large Multi-property Data Sets, Journal of Chemical Information and Modeling, Volume 56, Issue 5 (2018), which is incorporated herein by reference in its entirety. Moreover, the molecular pair series assignment tool can utilize the matched molecular pairs to generate a network graph composed of nodes (representing compounds) and edges (indicating matched molecular pair relations). Furthermore, the molecular pair series assignment tool can utilize a community detection algorithm to divide the connected network graph into (distinct) chemical series. Indeed, the molecular pair series assignment tool identifies compounds with similar structures and clusters the compounds.

Additionally, as illustrated in FIG. 7C, the AI tech-bio system 106 also displays a tech-bio prompt selector 732 (e.g., after generating and providing the response 730 for the prompt 726). As shown in the transition between FIGS. 7C and 7D, upon detecting a user interaction with the tech-bio prompt selector 732, the AI tech-bio system 106 displays, within the graphical user interface 708, a bio query prompt 734 (e.g., a phenomic clustering query prompt template with an input perturbation Gene1 and/or compounds, or hits, as identified in the previous response(s)). In particular, as shown in FIG. 7D, the phenomic clustering query prompt template includes a tech-bio query requesting a clustering of compounds identified for the selected (input) perturbation based on phenomic properties.

Figure 7D:
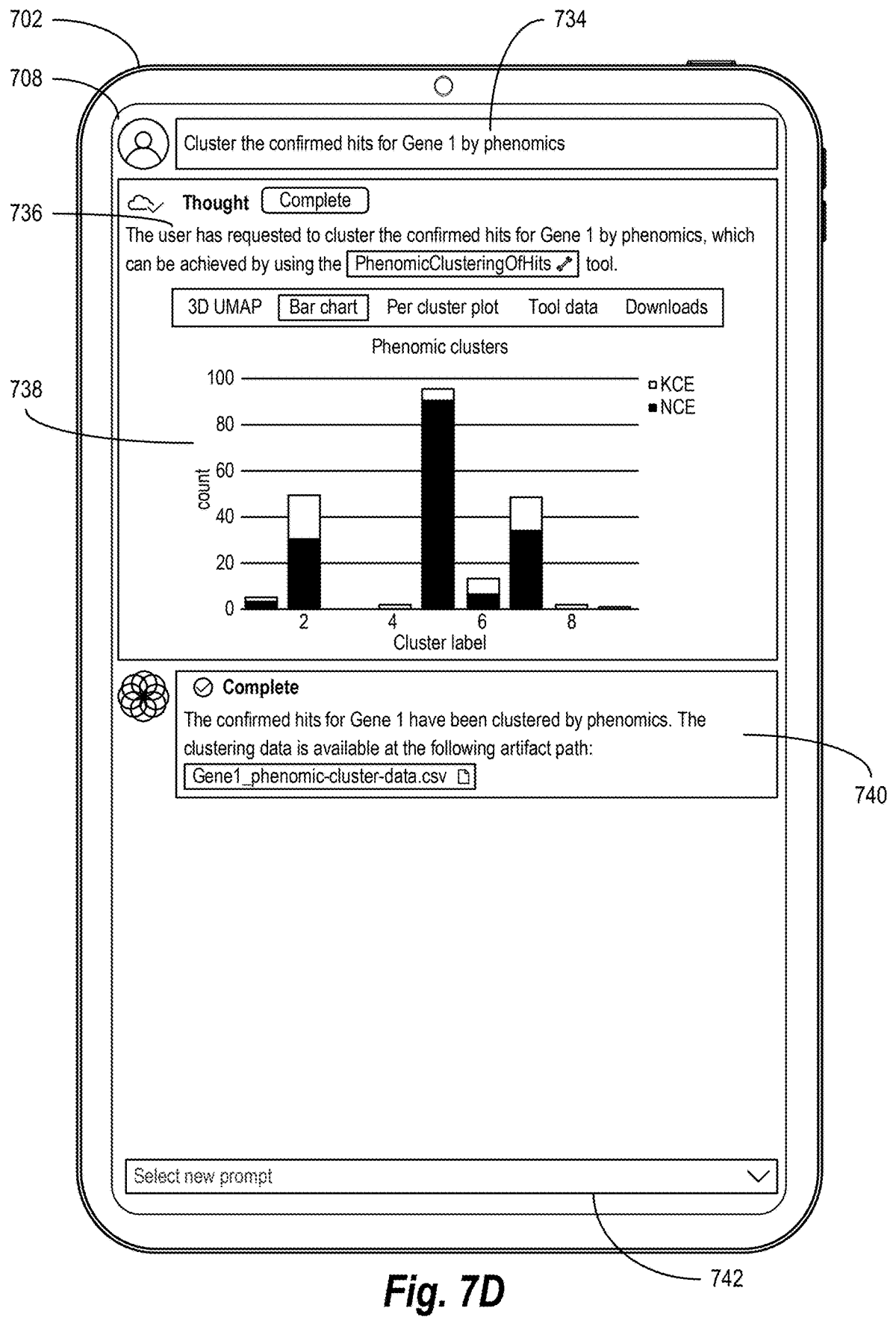

Furthermore, as shown in FIG. 7D, the AI tech-bio system 106 utilizes the language machine learning model to generate a modified prompt 736 (as a displayable execution request) for the tech-bio query prompt 734 (in accordance with one or more implementations herein). As shown in FIG. 7D, the modified prompt 736 indicates a selected tech-bio tool (e.g., a phenomic clustering tool) and a workflow to process the phenomic clustering tech-bio query from the phenomic clustering query prompt template. Indeed, as shown in FIG. 7D, the AI tech-bio system 106, utilizing the language machine learning model (in accordance with one or more implementations herein), causes the phenomic clustering tool with the input perturbation (e.g., Gene1) and identified compounds for the input perturbation to generate phenomic compound clusters based on phenomic properties.

Additionally, as further shown in FIG. 7D, the AI tech-bio system 106, via the language machine learning model, generates (from output of the phenomic clustering tool) visualizations 738 (for display). In particular, as shown in FIG. 7D, the AI tech-bio system 106 generates a visualization 738 to display cluster counts of phenomic clusters generated by the phenomic clustering tool (e.g., for NCEs and KCEs). Additionally, as illustrated in FIG. 7D, the AI tech-bio system 106, via the language machine learning model, also generates multiple outputs via varying visualization formats (e.g., an interactive 3D UMAP for compound clusters with navigational interactions and hovering interactions for compound data, such as compound identifiers and cluster identifiers), tech-bio tool data or structure information, and/or artifacts with selectable options to navigate between the generated data for the outputs of the phenomic clustering tool. Moreover, as shown in FIG. 7D, the AI tech-bio system 106, via the language machine learning model, also generates a response 740 from the data obtained via the phenomic clustering tool. For instance, as shown in FIG. 7D, the AI tech-bio system 106, via the language machine learning model, generates and displays the response 740 which indicates a link to artifacts for the phenomic clustering data (e.g., via a CSV file) for the input perturbation (e.g., Gene1).

In one or more implementations, the AI tech-bio system 106 (via the language machine learning model) causes a phenomic clustering tool to generate one or more phenomic clusters. For instance, the phenomic clustering tool can cluster data in a map to condense a number of compounds profiled by groupings that behave in a similar functional manner (e.g., measured by phenomic properties). For example, the phenomic clustering tool can utilize a variety of phenomic properties from a variety of tools or programs as the basis for clustering the compounds.

In one or more instances, the phenomic clustering tool can perform phenomic clustering utilizing compounds that associate with an input perturbation (e.g., via CAS, Jaccard, and/or toxicity thresholds). For example, the phenomic clustering tool can cluster compound data in a map embedding space utilizing a similarity distance measurement (e.g., cosine similarity, Euclidean distance) utilizing hierarchical clustering. Moreover, the phenomic clustering tool can select a clustering cutoff that maximizes a silhouette score of the data representing a ratio of how similar each data point is to other data points within a cluster to how similar the data point is to data points in different clusters. Indeed, based on the maximum silhouette score, the phenomic clustering tool utilizes the parameters to fit the compound data for a hypothesis and assigns each compound-concentration to a cluster. In one or more instances, the phenomic clustering tool can utilize the compound cluster assignments to observe (or determine) similarities (or relations) between compounds in a phenomic space.

As further illustrated in FIG. 7D, the AI tech-bio system 106 also displays a tech-bio prompt selector 742 (e.g., after generating and providing the response 740 for the prompt 736). As shown in the transition between FIGS. 7D and 7E, upon detecting a user interaction with the tech-bio prompt selector 742, the AI tech-bio system 106 displays, within the graphical user interface 708, a bio query prompt 744 (e.g., a comparison diagram prompt template with an input perturbation, matched molecular pair series associated with the input perturbation, and/or phenomic clusters associated with the input perturbation as identified in the previous response(s)). Indeed, as shown in FIG. 7E, the comparison diagram prompt template includes a tech-bio query requesting a comparison diagram (e.g., a Sankey diagram) between matched molecular pair series associated with the input perturbation and/or phenomic clusters associated with the input perturbation.

Figure 7E:
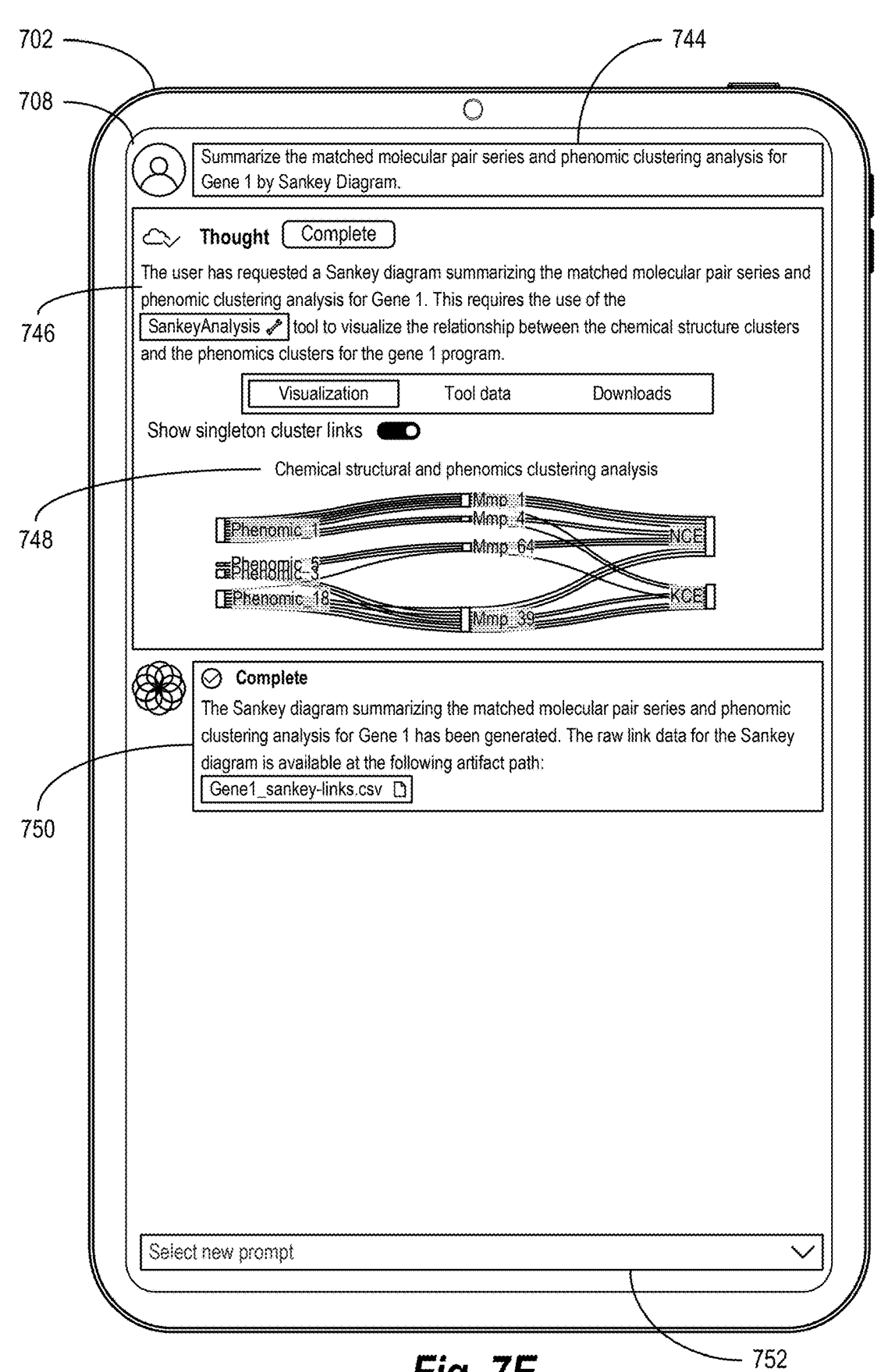

Additionally, as shown in FIG. 7E, the AI tech-bio system 106 utilizes the language machine learning model to generate a modified prompt 746 (as a displayable execution request) for the tech-bio query prompt 744 (in accordance with one or more implementations herein). As shown in FIG. 7E, the modified prompt 746 indicates a selected tech-bio tool (e.g., a cluster analysis comparison tool) and a workflow to process the comparison diagram tech-bio query from the comparison diagram prompt template. In particular, as shown in FIG. 7E, the AI tech-bio system 106, via the language machine learning model (in accordance with one or more implementations herein), causes the cluster analysis comparison tool to generate a comparison diagram (e.g., a Sankey diagram) utilizing the input perturbation (e.g., Gene1), matched molecular pair series associated with the input perturbation, and/or phenomic clusters associated with the input perturbation identified compounds for the input perturbation.

As also shown in FIG. 7E, the AI tech-bio system 106, via the language machine learning model, generates (from output of the cluster analysis comparison tool) visualizations 748 (for display). In particular, as shown in FIG. 7E, the AI tech-bio system 106 generates a visualization 748 to display a Sankey diagram (i.e., a comparisons diagram) between phenomic clusters, matched molecular pairs, and NCEs and/or KCEs generated by the cluster analysis comparison tool. Moreover, as illustrated in FIG. 7E, the AI tech-bio system 106, via the language machine learning model, also generates multiple outputs via varying visualization formats, tech-bio tool data or structure information, and/or artifacts with selectable options to navigate between the generated data for the outputs of the cluster analysis comparison tool. In addition, as shown in FIG. 7E, the AI tech-bio system 106, via the language machine learning model, also generates a response 750 from the data obtained via the cluster analysis comparison tool. For example, as illustrated in FIG. 7E, the AI tech-bio system 106, via the language machine learning model, generates and displays the response 750 which indicates a link to artifacts for the cluster analysis comparison data (e.g., via a CSV file).

In one or more instances, the AI tech-bio system 106 (via the language machine learning model) causes a cluster analysis comparison tool to generate a comparison between one or more datasets generated from (or for) the input perturbation and/or one or more compounds associated with the input perturbation. For example, the cluster analysis comparison tool generates a comparison diagram that compares or relates data on one or more properties (or information) generated from the input perturbation and/or one or more compounds associated with the input perturbation. As an example, the cluster analysis comparison tool can compare one or more phenomic compound clusters and matched molecular pair series (and novel and known chemical entities) to generate a comparison diagram. For instance, a comparison diagram can include, but is not limited to, charts, UMAPS, flow diagrams that represents relationships between different entities or categories, chord diagrams, and/or network diagrams.

As an example, the cluster analysis comparison tool can generate a Sankey diagram of matched molecular pair series and phenomic clustering analysis (e.g., as shown in the visualization 748). In particular, the cluster analysis comparison tool can generate a Sankey diagram that visually represents relationships (or flow) between phenomic compound clusters (as described herein), matched molecular pair series (as described herein), and novel chemical entities (NCEs) and/or known chemical entities (KCEs). Indeed, the cluster analysis comparison tool can generate a Sankey diagram that utilizes line thickness in the flow to represent varying quantities (or strength) of relationships between the phenomic compound clusters (as described herein), matched molecular pair series (as described herein), and novel chemical entities (NCEs) and/or known chemical entities (KCEs).

As further shown in FIG. 7E, the AI tech-bio system 106 also displays a tech-bio prompt selector 752 (e.g., after generating and providing the response 750 for the prompt 746). As shown in the transition between FIGS. 7E and 7F, upon detecting a user interaction with the tech-bio prompt selector 752, the AI tech-bio system 106 displays, within the graphical user interface 708, a bio query prompt 754 (e.g., a mechanism-of-action query template with an input perturbation and one or more compound clusters associated with the input perturbation as identified in the previous response(s)). Indeed, as shown in FIG. 7F, the mechanism-of-action query template includes a tech-bio query requesting a mechanism of action data (e.g., mechanism of action predictions) for compounds (or compound clusters) associated with the input perturbation.

Moreover, as shown in FIG. 7F, the AI tech-bio system 106 utilizes the language machine learning model to generate a modified prompt 756 (as a displayable execution request) for the tech-bio query prompt 754 (in accordance with one or more implementations herein). As shown in FIG. 7F, the modified prompt 756 indicates a selected tech-bio tool (e.g., a mechanism-of-action modeling tool) and a workflow to process a mechanism-of-action tech-bio query from the mechanism-of-action query template. For instance, as shown in FIG. 7F, the AI tech-bio system 106, via the language machine learning model (in accordance with one or more implementations herein), causes the mechanism-of-action modeling tool to generate a one or more mechanism of action predictions (e.g., via a heatmap) utilizing compounds or compound clusters corresponding to the input perturbation.

As also shown in FIG. 7F, the AI tech-bio system 106, via the language machine learning model, generates (from output of the mechanism-of-action modeling tool) visualizations 758 (for display). Indeed, as shown in FIG. 7F, the AI tech-bio system 106 generates a visualization 758 to display a heatmap between compounds of a compound cluster associated with the input perturbation and one or more detectable mechanisms of action (MOAs) generated (or determined) by the mechanism-of-action modeling tool. Moreover, as illustrated in FIG. 7F, the AI tech-bio system 106, via the language machine learning model, also generates multiple outputs via varying visualization formats, tech-bio tool data or structure information, and/or artifacts with selectable options to navigate between the generated data for the outputs of the mechanism-of-action modeling tool. Furthermore, as shown in FIG. 7F, the AI tech-bio system 106, via the language machine learning model, also generates a response 760 from the data obtained via the mechanism-of-action modeling tool. For instance, as illustrated in FIG. 7F, the AI tech-bio system 106, via the language machine learning model, generates and displays the response 760 which indicates a link to artifacts for the mechanism-of-action prediction data (e.g., via a CSV file).

In addition, as illustrated shown in FIG. 7F, the AI tech-bio system 106 also displays a tech-bio prompt selector 762 (e.g., after generating and providing the response 760 for the prompt 756). Furthermore, in some cases, the AI tech-bio system 106 enables a selection or input of a particular compound input within the bio query prompt 764 (e.g., via a text input bar and/or a dropdown menu) for the mechanism-of-action query template. As shown in the transition between FIGS. 7F and 7G, upon detecting a user interaction with the tech-bio prompt selector 762, the AI tech-bio system 106 displays, within the graphical user interface 708, a bio query prompt 764 (e.g., a mechanism-of-action query template with an input (or selected) compound associated with the input perturbation as identified in the previous response(s)). Indeed, as shown in FIG. 7G, the mechanism-of-action query template includes a tech-bio query requesting, mechanism of action data (e.g., mechanism of action predictions) for a specific (selected or input) compound.

Figure 7G:
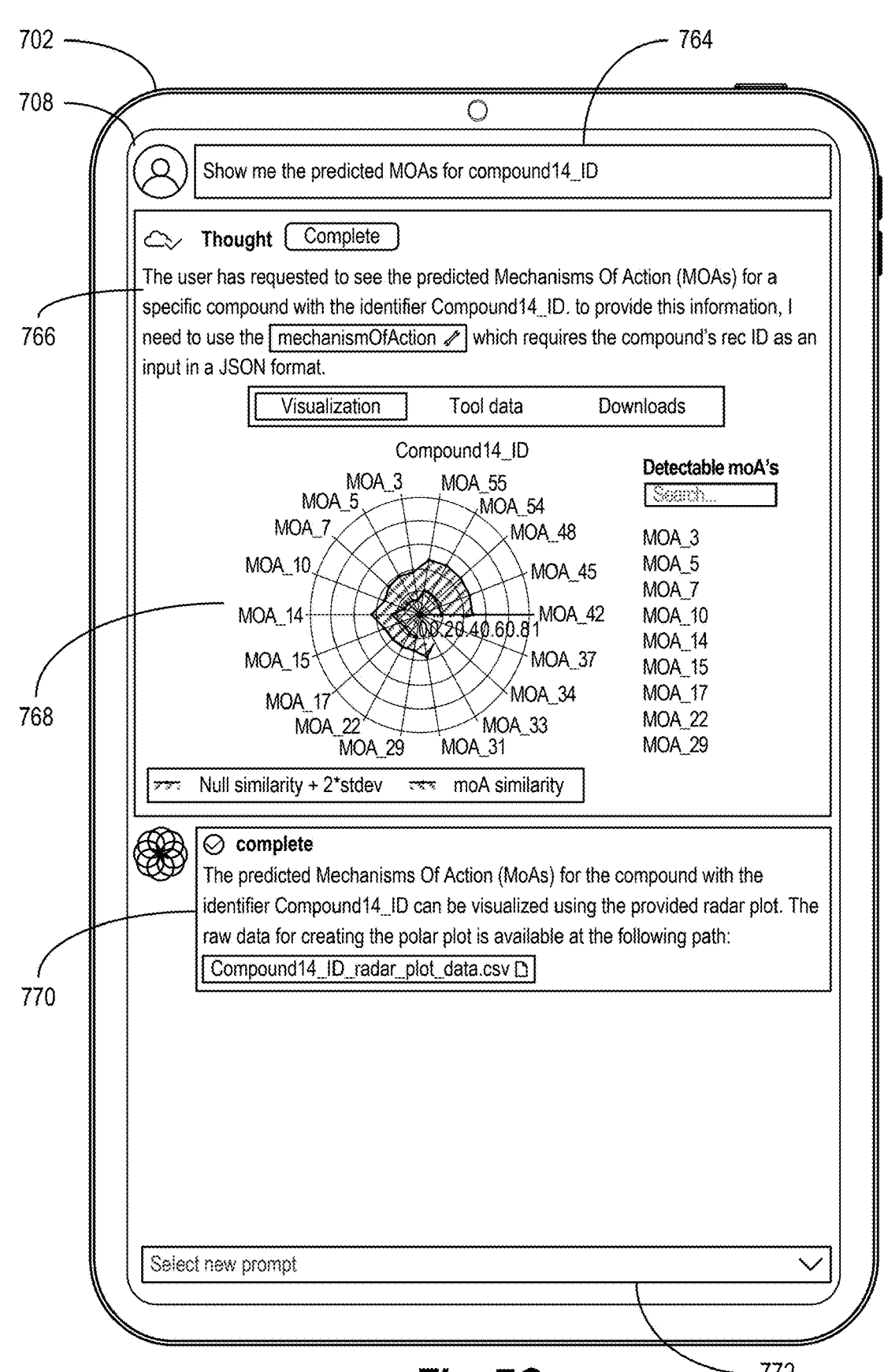

Additionally, as shown in FIG. 7G, the AI tech-bio system 106 utilizes the language machine learning model to generate a modified prompt 766 (as a displayable execution request) for the tech-bio query prompt 764 (in accordance with one or more implementations herein). As shown in FIG. 7G, the modified prompt 766 indicates a selected tech-bio tool (e.g., a mechanism-of-action modeling tool) and a workflow to process a mechanism-of-action tech-bio query from the mechanism-of-action query template. For instance, as shown in FIG. 7G, the AI tech-bio system 106, via the language machine learning model (in accordance with one or more implementations herein), causes the mechanism-of-action modeling tool to generate a one or more mechanism of action predictions (e.g., via a radar or polar map) for the identified for the input perturbation.

As also shown in FIG. 7G, the AI tech-bio system 106, via the language machine learning model, generates (from output of the mechanism-of-action modeling tool) visualization 768 (for display). Indeed, as shown in FIG. 7G, the AI tech-bio system 106 generates a visualization 768 to display a radar (or polar) map between multiple predicted mechanisms of action in relation to a particular compound associated with the input perturbation. Additionally, as illustrated in FIG. 7G, the AI tech-bio system 106, via the language machine learning model, also generates multiple outputs via varying visualization formats, tech-bio tool data or structure information, and/or artifacts with selectable options to navigate between the generated data for the outputs of the mechanism-of-action modeling tool. Furthermore, as shown in FIG. 7G, the AI tech-bio system 106, via the language machine learning model, also generates a response 770 from the data obtained via the mechanism-of-action modeling tool. For instance, as illustrated in FIG. 7G, the AI tech-bio system 106, via the language machine learning model, generates and displays the response 770 which indicates a link to artifacts for the mechanism-of-action prediction data (e.g., via a CSV file) for a particular compound (e.g., Compound14_ID).

Furthermore, as illustrated shown in FIG. 7G, the AI tech-bio system 106 also displays a tech-bio prompt selector 772 (e.g., after generating and providing the visualization 768 for the prompt 766). Indeed, the AI tech-bio system 106 can continuously display a tech-bio prompt selector to continuously receive prompt template selections until one or more user tech-bio queries are answered and/or upon detecting an exit accession by the user. In some instances, the AI tech-bio system 106, via the language learning model, decides that the response from the one or more tech-bio tools is the final (or completed) response for the tech-bio query.

In one or more implementations, the AI tech-bio system 106 (via the language machine learning model) causes a mechanism-of-action modeling tool to generate mechanism of action (MOA) predictions for compounds in a compound cluster and/or matched molecular pair series. In one or more instances, the mechanism-of-action modeling tool utilizes MOA representations with corresponding detection confidence scores that indicate whether cell representations in an MOA representation provide a meaningful signal to predict the MOA generated utilizing mechanism-of-action annotations on cell representation embeddings that correspond to the known MOAs in a shared feature space. Indeed, the mechanism-of-action modeling tool detects MOAs for compounds by identifying compounds with phenoprints within an MOA representation (generated from MOA annotations). Indeed, the mechanism-of-action modeling tool can generate a confidence score by comparing the similarity measure between the MOA representation and the query perturbation against similarity measures between the MOA representation and other sampled query cell representations. For example, the mechanism-of-action modeling tool can generate MOA predictions for compounds in a phenomic compound cluster and/or matched molecular pair series and/or individual compounds as described in application Ser. No. 18/663,819 (as described above).

In one or more instances, the mechanism-of-action modeling tool determines a threshold number (e.g., top 20, top 15) of predicted MOAs ranked by cosine similarity for each compound in a phenomic compound cluster and/or matched molecular pair series. Moreover, in one or more instances, the mechanism-of-action modeling tool utilizes a union of the predicted MOAs lists across compounds in a phenomic compound cluster of interest (or matched molecular pair series) to determine a set of MOAs to visualize in a heatmap (e.g., as shown in the visualization 758). Indeed, the AI tech-bio system 106 (via the language machine learning model) generates the visualization 758 as a heatmap representing an intensity of similarity (e.g., the strength of a cosine similarity) between compound-MOA pairs. In some cases, the AI tech-bio system 106 (via the language machine learning model) also reorders compounds and MOAs based on their similarity of predicted scores (e.g., utilizing hierarchical clustering on their Euclidean distances) to highlight (or emphasize) common MOAs at the cluster level. In one or more embodiments, the AI tech-bio system 106 (via the language machine learning model) generates the visualization 758 as a heatmap that includes an indication of MOAs displayed in a radar plot for a specific compound via highlighting of the detectable MOAs.

In one or more instances, the mechanism-of-action modeling tool detects MOAs for an individual compound by determining whether the compound is significantly similar to a detected MOA utilizing a null distribution of randomly sampled compounds (e.g., hundreds or thousands of compounds). For instance, the mechanism-of-action modeling tool can generate a null distribution by computing the similarities between each randomly sampled compound concentration to an average MOA vector. Moreover, the mechanism-of-action modeling tool can select a maximum cosine similarity across the compound concentrations to compute a mean and standard deviation of the null cosine similarity distribution.

In addition, for a particular queried compound (e.g., a selected compound), the mechanism-of-action modeling tool can determine a maximum cosine similarity to the average MOA vector across compound concentrations. Indeed, the mechanism-of-action modeling tool can determine that a queried compound is significantly similar to an MOA when the max similarity of the query compound to the MOA satisfies (e.g., equals and/or exceeds) a null mean and/or a null standard deviation of the null distribution. For example, the AI tech-bio system 106 (via the language machine learning model) generates the visualization 768 as a radar (or polar) plot that indicates a particular compound detected MOAs and whether the particular compound is significantly similar (e.g., using cosine similarities) to one or more MOAs (using a null mean and/or a null standard deviation of the null distribution). In some instances, the mechanism-of-action modeling tool can generate (or utilize) radar (or polar) plots for detecting MOAs as described in application Ser. No. 18/663,819 (as described above).

Although FIGS. 7A-7G illustrates a particular workflow or order of tasks, the AI tech-bio system 106 (via the language machine learning model) can receive selections of tech-bio query prompt templates in various orders and execute various combinations of tasks in accordance with one or more implementations herein.

Furthermore, as mentioned above, the AI tech-bio system 106 can receive a free-form (e.g., open ended) tech-bio query and utilize the language machine learning model to generate and transmit an execution request to one or more tech-bio exploration tools to generate a response for the free-form (e.g., open ended) tech-bio query (or workflow of queries). For example, FIGS. 8A-8L illustrate the AI tech-bio system 106 (via the language machine learning model) utilize free-form tech-bio queries to orchestrate a workflow of tech-bio tools, experiment design, scheduling, and third-party tools to generate responses to the free-form text tech-bio queries.

Figure 8A:
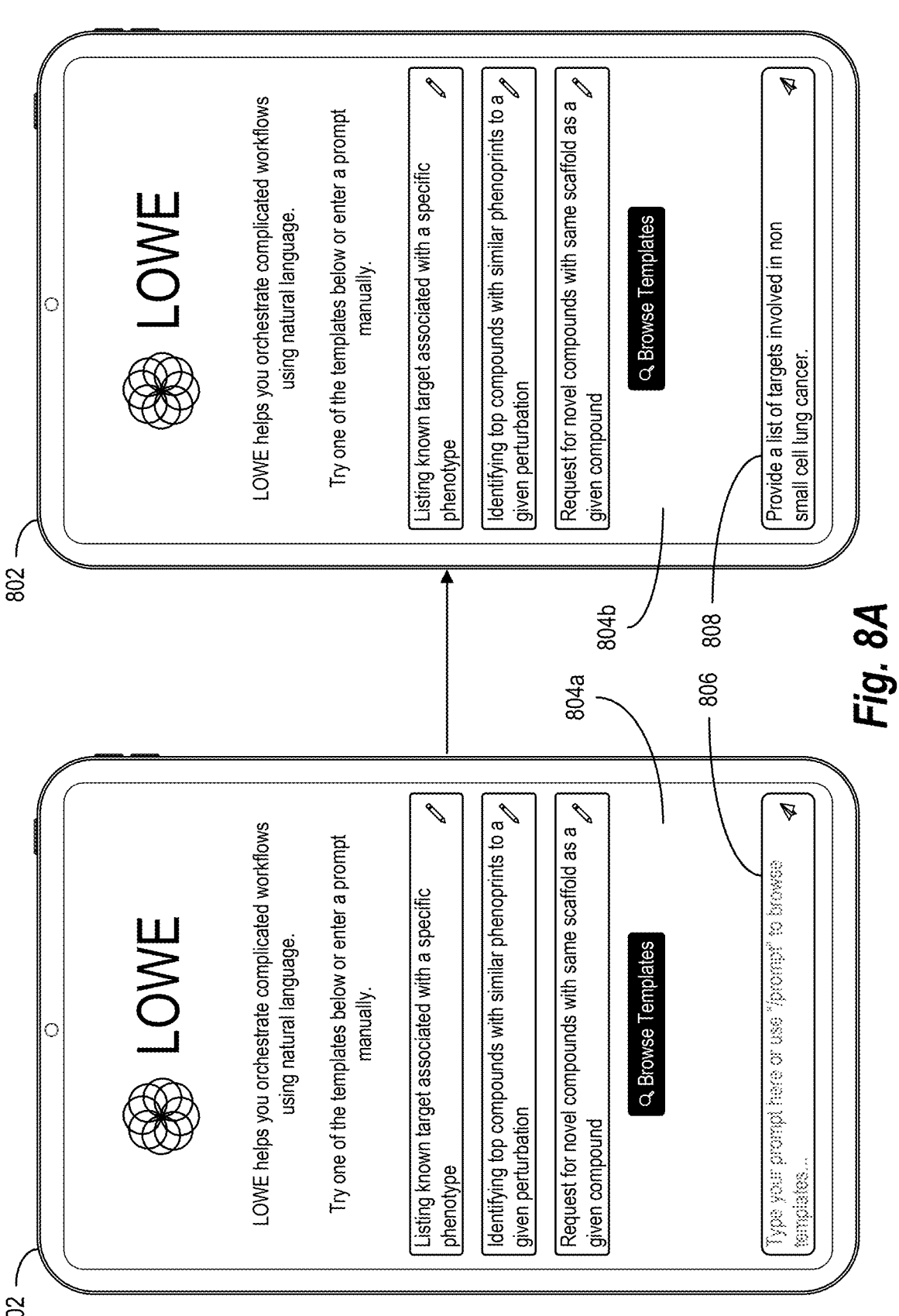
Figure 8B:
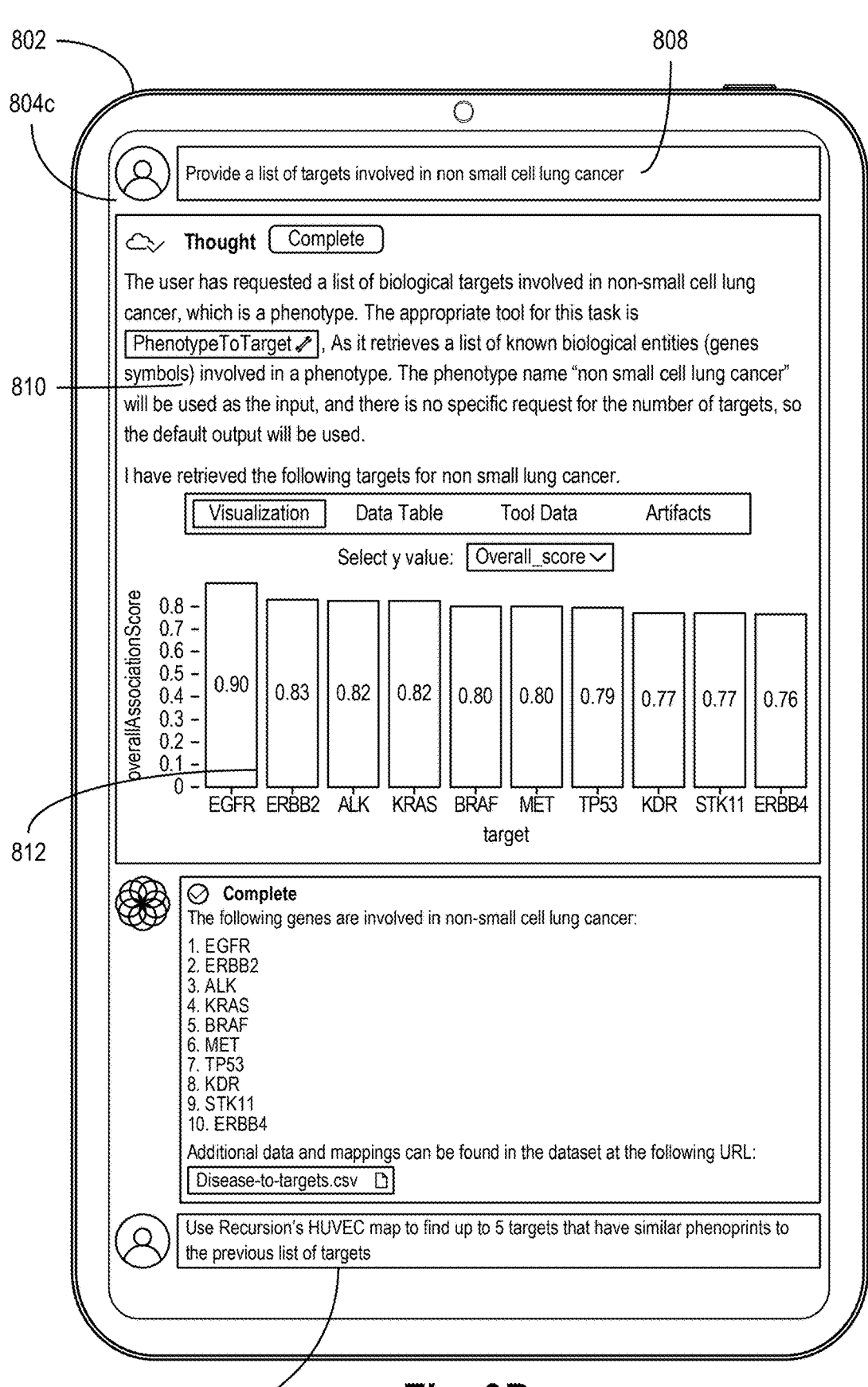

In particular, as shown in FIG. 8A via the transition from graphical user interface 804a and graphical user interface 804b, the AI tech-bio system 106 receives a free-form tech-bio query prompt 808 within a prompt input element 806 (on a client device 802). Indeed, as shown in FIG. 8A, the AI tech-bio system 106 receives the free-form tech-bio query prompt 808 indicating the following prompt: "provide a list of targets involved in non-small cell lung cancer." As further shown in FIG. 8B, the AI tech-bio system 106 (via the language machine learning model) leverages a phenotypeToTarget tool that utilizes datasets on protein targets to identify protein targets associated with a particular phenotype (e.g., non-small cell lung cancer). Indeed, as shown in FIG. 8B, the AI tech-bio system 106 (via the language machine learning model) generates and displays, within a graphical user interface 804c, a modified prompt 810 (for the free-form tech-bio query prompt 808) to demonstrate the workflow utilized by the language machine learning model for the prompt. As further shown in FIG. 8B, the AI tech-bio system 106 (via the language machine learning model) generates a response 812 (e.g., using visualizations, text responses, and artifacts) that provide information based on a retrieval and analysis of outputs of the phenotypeToTarget tool (e.g., association scores for target genes for non-small cell lung cancer).

As further shown in FIG. 8B, the AI tech-bio system 106 receives a free-form tech-bio query prompt 814 (e.g., from a user input) indicating the following prompt: "use Recursion's HUVEC map to find up to 5 targets that have similar phenoprints to the previous list of targets." As further shown in FIG. 8C, the AI tech-bio system 106, in response to the free-form tech-bio query prompt 814, the AI tech-bio system 106 (via the language machine learning model) leverages a phenoprints comparer tool to utilize genome-wide CRISPR knockout data (e.g., from primary human endothelial cells) to query known small cell lung cancer genes to identify if other genes, when knocked out, result in a similar cellular morphological phenotype (from the Recursion HUVEC map, a Neuromap having relationships between genes and phenotypes). Indeed, the AI tech-bio system 106 can query a number (e.g., trillions, billions) of relationships predicted from a number (e.g., hundreds of millions) of experiments conducted via the tech-bio exploration system 104. Indeed, the AI tech-bio system 106 (via the language machine learning model) displays, within a graphical user interface 804d of the client device 802, a prompt 816 to indicate the above-mentioned process.

Figure 8C:
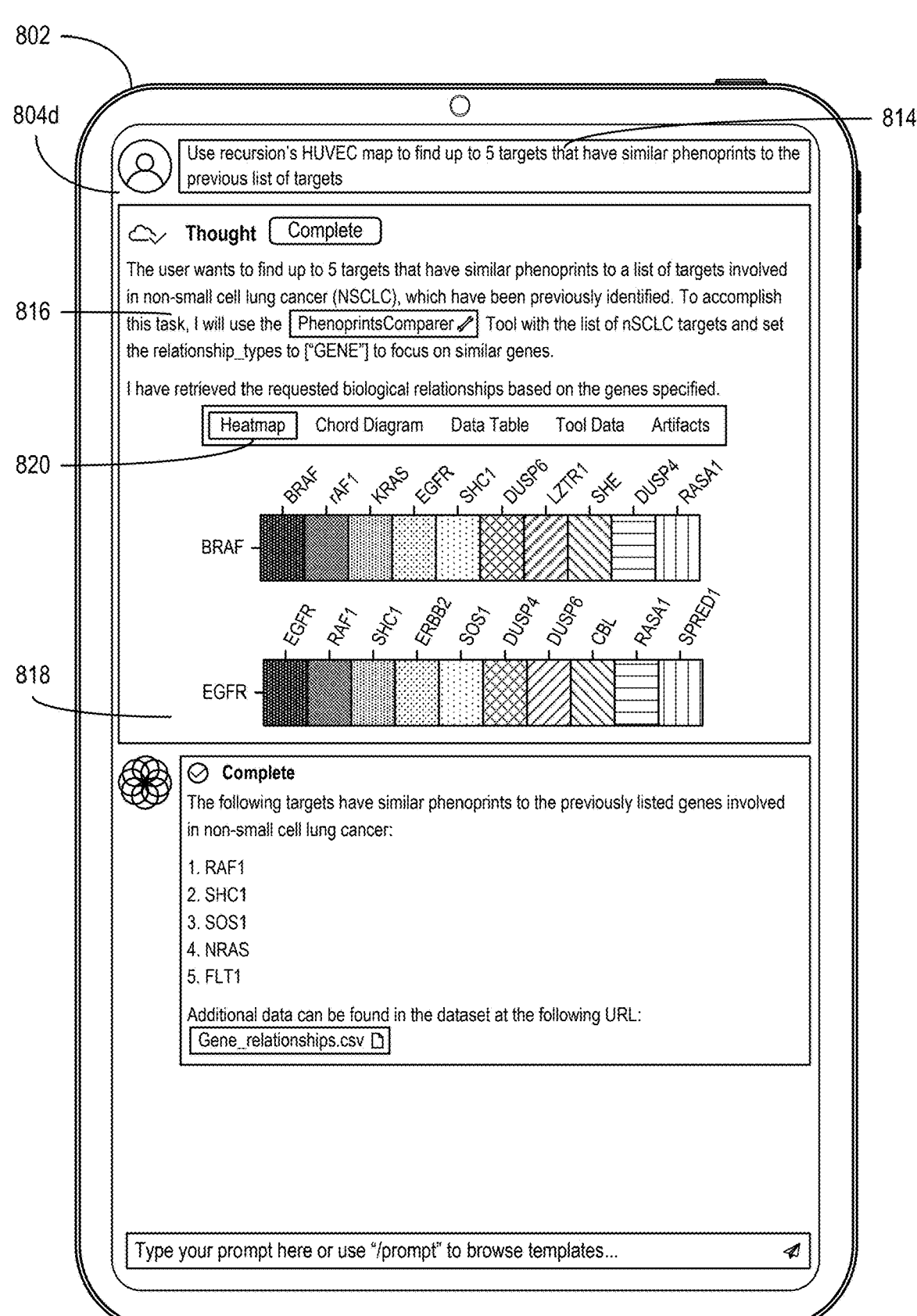

Furthermore, as shown in FIG. 8C, the AI tech-bio system 106 (via the language machine learning model) generates a response 818 to indicate targets with similar phenoprints to the previously listed genes (and a heat map visualization for the identified targets). As an example, the response 818 lists RAFI as related to many of the previously mentioned genes (e.g., a component of the MAPK signaling pathway). In addition, the response 818 also displays an artifact having a dataset of the output data from the phenoprints comparer tool.

Furthermore, as shown in the transition from FIG. 8C to FIG. 8D, upon receiving a user interaction with the graphical user interface element 820 to navigate between different visualizations generated by the AI tech-bio system 106 (via the language machine learning model), the AI tech-bio system 106 displays, within a graphical user interface 804e of the client device 802, an additional visualization 822 (e.g., a response). Indeed, as shown in FIG. 8D, the visualization 822 represents a chord diagram for the previously determined genes to illustrate cellular morphological phenotype similarities between the genes.

In addition, as shown in FIG. 8E, the AI tech-bio system 106 receives a free-form tech-bio query prompt 821 (e.g., from a user input) indicating the following prompt: "use MatchMaker to find the top 100 active compounds for RAFI, compute their ADMET properties, filter them to keep the top 50 with the highest solubility." Indeed, the tech-bio query prompt 821 includes multiple requests for the AI tech-bio system 106. As shown in FIG. 8E, the AI tech-bio system 106 (utilizing the language machine learning model) analyzes the tech-bio query prompt 821 to generate a prompt 824 to indicate a workflow (e.g., thoughts, actions, inputs, and/or tech-bio tools) to accomplish the tech-bio query prompt 821.

For example, as illustrated in FIG. 8E, the AI tech-bio system 106, in response to the tech-bio query prompt 821, the AI tech-bio system 106 (via the language machine learning model) leverages a MatchMakerAPI tool to predict drug-target interactions between the selected target of RAFI and molecules to identify small molecules. Then, the AI tech-bio system 106 (via the language machine learning model) leverages an ADMET prediction tool to generate ADMET properties for the identified small molecules. Lastly, the AI tech-bio system 106 (via the language machine learning model) leverages a table analysis tool to filter compounds based on solubility. Indeed, the AI tech-bio system 106 (via the language machine learning model) displays, within a graphical user interface 804f of the client device 802, the prompt 824 to indicate the above-mentioned process.

Figure 8F:
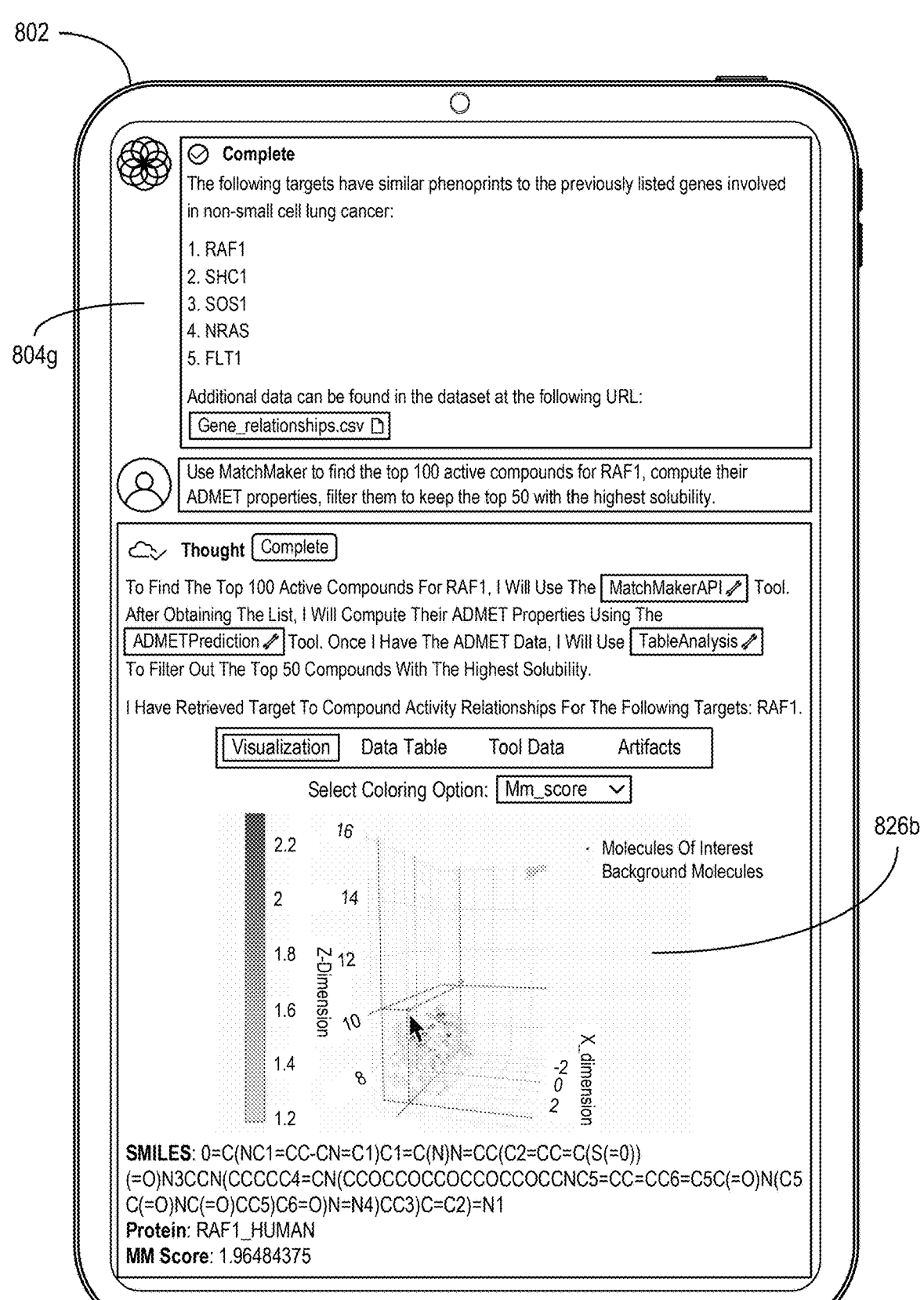

Furthermore, the AI tech-bio system 106 (via the language machine learning model) causes the MatchMakerAPI tool to generate target to compound activity relationships for the selected target (e.g., RAFI). Indeed, the MatchMakerAPI tool can predict interaction probabilities between a number of small molecule and a number of proteins within a proteome. For example, the MatchMakerAPI can focus on individual protein pockets rather than the entire protein to enhance predictive accuracy. As shown in FIG. 8E, upon utilizing the MatchMakerAPI tool, the AI tech-bio system 106 (utilizing the language machine learning model) generates a response 826a from the output of the MatchMakerAPI tool to display retrieved target to compound activity relationships for the selected target of RAFI (e.g., via a visualized chart and text-based response). Furthermore, as shown in FIG. 8F, the AI tech-bio system 106 generates and displays (within a graphical user interface 804g of the client device 802) the response 826b as an interactive plot graph that, upon receiving hover interactions with data points, displays data for a particular molecule (from the output of the MatchMakerAPI tool).

Figure 8G:
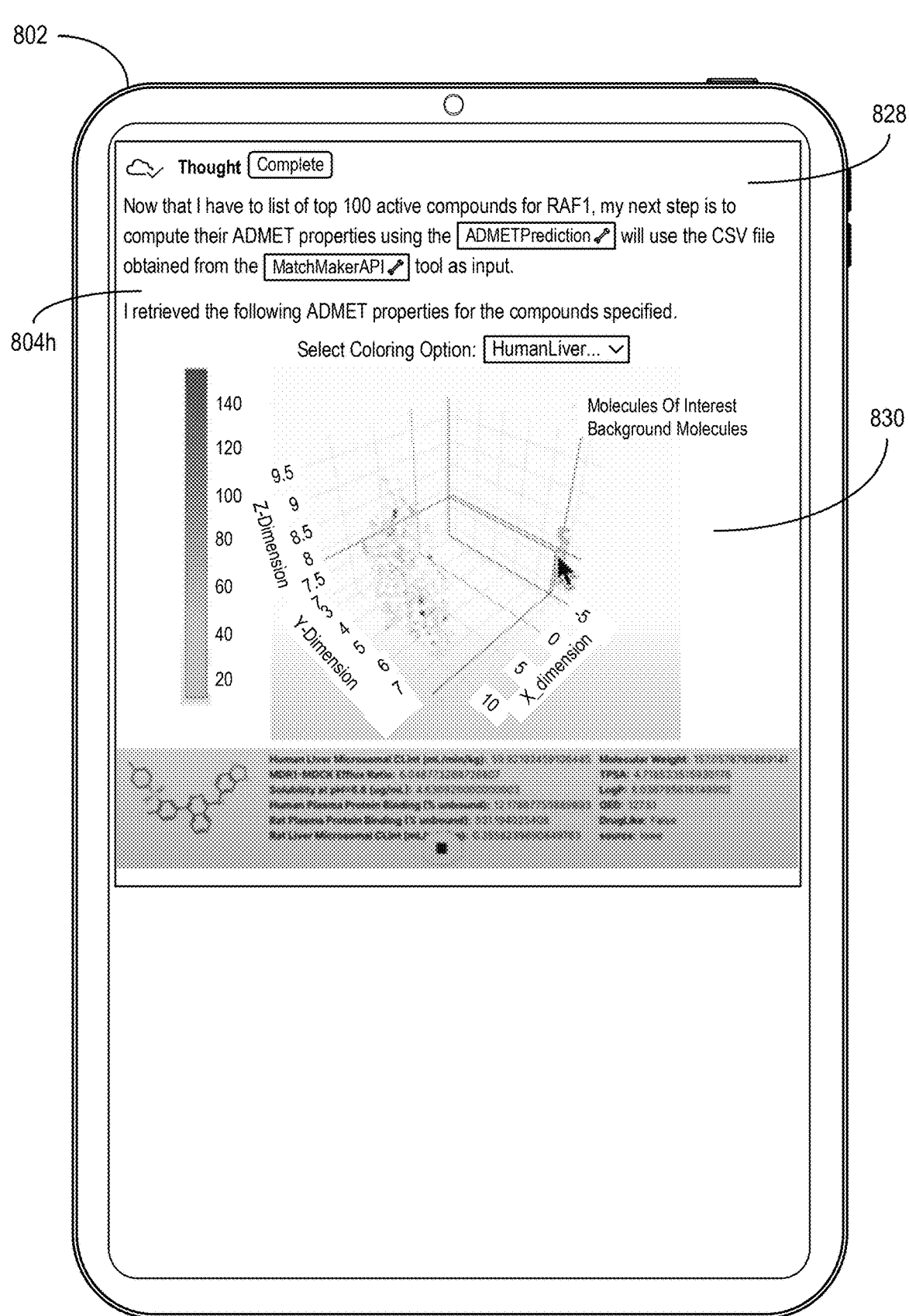

Moreover, as shown in FIG. 8G, the AI tech-bio system 106 continues to execute the workflow described in the prompt 824. For example, as shown in FIG. 8G, the AI tech-bio system 106 (via the language machine learning model) displays, within a graphical user interface 804h of the client device 802, a prompt 828 that indicates the continued execution of the above-mentioned workflow by utilizing the output from the MatchMakerAPI tool with the ADMETPrediction tool to determine ADMET properties for the identified compounds. Furthermore, as shown in FIG. 8G, upon causing the ADMETPrediction tool to generate the ADMET properties, the AI tech-bio system 106 (via the language machine learning model) provides for display, within the graphical user interface 804h, a response 830 that includes a visualization of a 3D scatter plot illustrating fingerprint embeddings for each compound and ADMET properties (e.g., upon detecting an interaction with a particular embedding or molecule within the response 830).

Additionally, as shown in FIG. 8H, the AI tech-bio system 106 (via the language machine learning model) continues to execute tasks for the workflow described in the prompt 824. In particular, as illustrated in FIG. 8H, the AI tech-bio system 106 (via the language machine learning model) displays, within a graphical user interface 804i of the client device 802, a prompt 832 that indicates the continued execution of the above-mentioned workflow by utilizing the output from the ADMETPrediction tool (e.g., the ADMET properties data for the identified compounds from the MatchMakerAPI tool) to filter based on solubility. Indeed, as shown in FIG. 8H, the AI tech-bio system 106 (via the language machine learning model) causes a Table Analysis tool to filter compound data based on specific properties (e.g., ADMET properties) corresponding to the compounds. For example, upon causing the TableAnalysis tool to filter the compounds based on solubility using the ADMET properties data, the AI tech-bio system 106 (via the language machine learning model) provides for display, within the graphical user interface 804i, a response 834 that includes a visualization of the filtered compounds (based on solubility) via SMILES molecular structure strings of the compounds. In addition, as shown in FIG. 8H, the AI tech-bio system 106 (via the language machine learning model) also generates an artifact 836 that includes the complete dataset of filtered compounds (e.g., a CSV file).

Figure 8I:
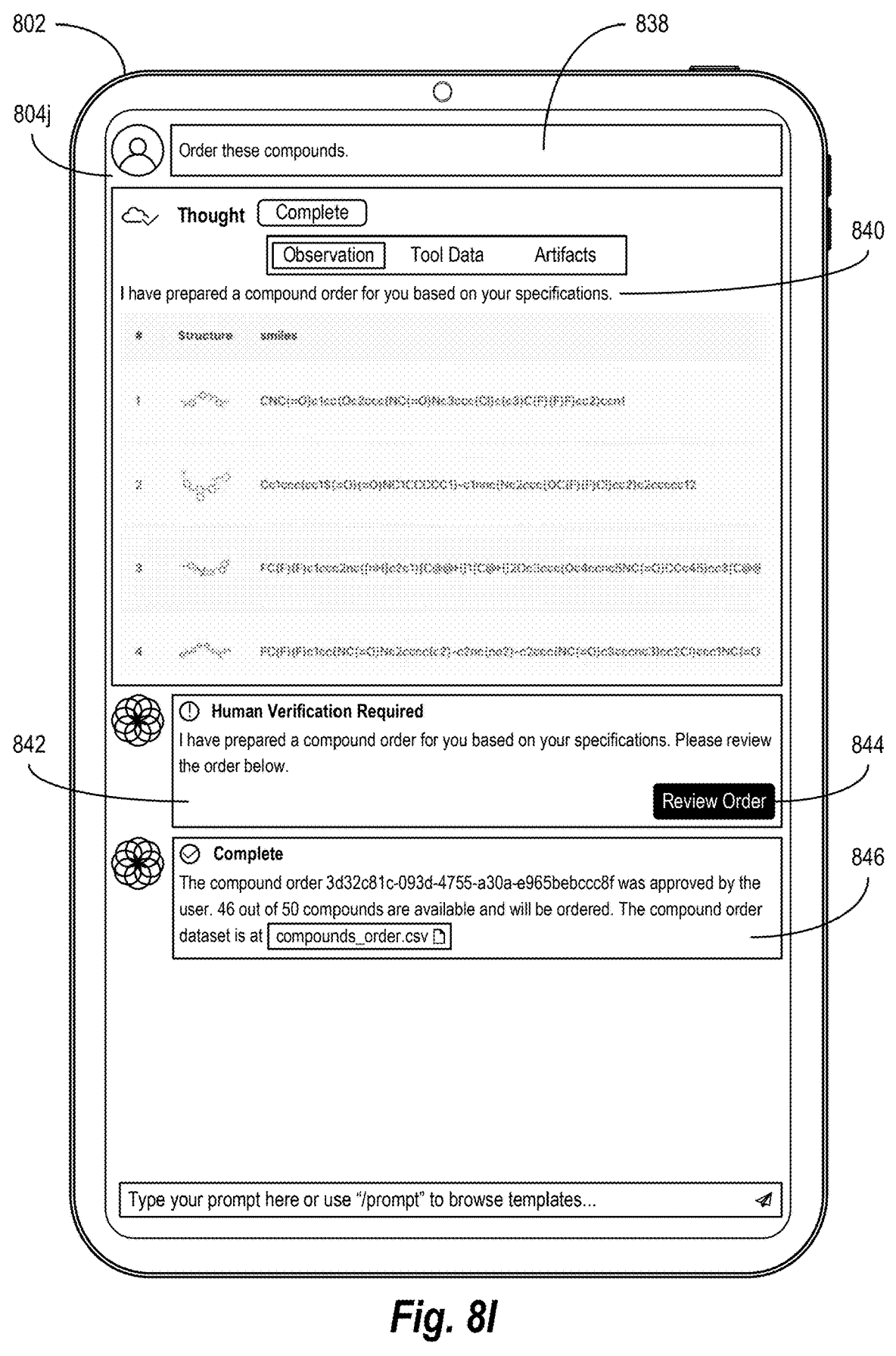

In addition, as shown in FIG. 8I, the AI tech-bio system 106 (via the language machine learning model) can interact with third-party tools (e.g., via APIs). For example, as shown in FIG. 8I, the AI tech-bio system 106 receives a prompt 838 (via user input) indicating a request to order the previously determined compounds (e.g., from response 834 and artifact 836). In response to the prompt 838 (e.g., "order these compounds"), the AI tech-bio system 106 (utilizing the language machine learning model) generates and displays, within a graphical user interface 804j of the client device 802, a prompt 840 (e.g., as a displayable execution request) that represents a compound order request (e.g., for an external third-party chemistry or compound supplier API) for the compounds identified by the language machine learning model in the response 834 and artifact 836.

As further shown in FIG. 8I, the AI tech-bio system 106 (via the language machine learning model) provides, for display within the graphical user interface 804j, a prompt 842 indicating a prepared compound order with a selectable option 844 to review the compound order request. Indeed, in one or more implementations, the AI tech-bio system 106 displays a review of the compound order request (e.g., via a file, a pop up window, an order fulfillment system user interface) upon receiving a user interaction with the selectable option 844 to review the compound order request. Moreover, as shown in FIG. 8I, upon receiving a user interaction that indicates a confirmation (or acceptance) of the compound order request, the AI tech-bio system 106 (via the language machine learning model) executes the compound order request with the third-party tool (or system) by transmitting the compound order request (or communicating the order request via an API) to the third-party system (e.g., a chemistry supply vendor system, compound vendor system). Indeed, as shown in FIG. 8I, the AI tech-bio system 106 (utilizing the language machine learning model) generates and displays a response 846 indicating an executed compound order request and information for the compound order request (e.g., with an order confirmation number, a description of how many compounds were ordered, and an artifact including data on the compound order via a CSV file).

In one or more instances, the AI tech-bio system 106 (via the language machine learning model) can also design and schedule an experiment to test the ordered compounds (e.g., schedule in advance for when the ordered compounds are delivered and/or upon receiving the ordered compounds). For example, the AI tech-bio system 106 (via the language machine learning model) can transmit a notification to a client device indicating that the compounds from the compound order request were delivered and/or stored in a storage system of the tech-bio exploration system 104. Indeed, upon receiving the compounds and ordering the compounds, the AI tech-bio system 106 (via the language machine learning model) can enable designing and/or scheduling an experiment for the ordered compounds to extract various properties and/or bio-activity relationships from the ordered compounds.

For example, FIG. 8J illustrates the AI tech-bio system 106 (via the language machine learning model) enabling the design and scheduling of one or more experiments for the ordered compounds (as part of the workflow from FIG. 8I). In particular, as shown in FIG. 8J, the AI tech-bio system 106 receives a prompt 848 (via user input) indicating a request to design a phenomics experiment in HUVEC cells to test the previously ordered compounds (from the response 846) for phenosimilarity to RAFI (e.g., the target from this workflow). In response to the prompt 848, the AI tech-bio system 106 (utilizing the language machine learning model) generates and displays, within a graphical user interface 804k of the client device 802, a prompt 850 (e.g., as a displayable execution request and/or thought, action, and/or input) to indicate a workflow to initiate a phenomics experiment from the ordered compounds. Moreover, as shown in FIG. 8J, the AI tech-bio system 106 (via the language machine learning model), as part of the prompt 850, confirms that the ordered compounds were retrieved for the phenomics experiment.

As further shown in FIG. 8J, the AI tech-bio system 106 (via the language machine learning model) provides, for display within the graphical user interface 804k, a prompt 852 indicating a phenomics experiment scheduling and experiment information. In addition, as shown in FIG. 8J, the AI tech-bio system 106 (via the language machine learning model) provides, for display within the graphical user interface 804k, a prompt 854 indicating that a phenomics experiment is ready to schedule with a selectable option 856 to review the phenomics experiment. Indeed, in one or more instances, the AI tech-bio system 106 displays a review of the phenomics experiment (e.g., via a file, a pop up window, an experiment design tool user interface) upon receiving a user interaction with the selectable option 856 to review the phenomics experiment.

Furthermore, as shown in FIG. 8J, upon receiving a user interaction indicating a confirmation (or acceptance) of the phenomics experiment on the ordered compounds, the AI tech-bio system 106 (via the language machine learning model) schedules and/or executes the phenomics experiment. For instance, the AI tech-bio system 106 (via the language machine learning model) can communicate with an experiment design tool (of the tech-bio exploration system 104) to design, schedule, and/or execute the phenomics experiment for the ordered compounds. In some cases, the AI tech-bio system 106 (via the language machine learning model) can communicate with an experiment design tool to generate an experiment that utilizes relevant control data for building biology models to generate a reliable dataset that is useable for multiple phenomics modeling and/or experimentation tasks. As shown in FIG. 8J, the AI tech-bio system 106 (via the language machine learning model) displays a prompt 858 to indicate a scheduled phenomics experiment. For instance, in the example of FIG. 8J, the AI tech-bio system 106 (via the language machine learning model) generates and schedules a phenomics experiment for a dose-response analysis to see if the ordered compounds mimic RAFI knockout in primary human endothelial cells.

Furthermore, upon executing and the tech-bio exploration system 104 completing the phenomic experiments for the above-mentioned compounds, the AI tech-bio system 106 (via the language machine learning model) can utilize the data (or observations) from the phenomic experiments to execute one or more additional tasks for one or more additional tech-bio queries. For example, as shown in FIG. 8K, the AI tech-bio system 106 (via the language machine learning model) generates and displays, via a graphical user interface 804*l* of the client device 802, a response 860 to indicate the completion of the phenomic experiments. For example, the response 860 can also include output data on one or more compounds (from the experiment compounds) identified to mimic the RAFI knockout phenotype (suggesting similar biological function). For instance, the AI tech-bio system 106 (via the language machine learning model) can identify one or more compounds from the experiment output data (e.g., via the MatchMakerAPI tool) that mimic the RAFI knockout phenotype.

As further shown in FIG. 8K, the AI tech-bio system 106 receives a prompt 862 indicating a tech-bio query to identify novel molecules in a chemical neighborhood of a selected compound from the experiment output data that mimics the RAFI knockout phenotype (e.g., via an input and/or selection from a list of the compounds) and ADMET properties for the novel molecules. As further shown in FIG. 8K, the AI tech-bio system 106, in response to the prompt 862, the AI tech-bio system 106 (via the language machine learning model) leverages a ChemicalNeighborExploration tool that utilizes a generative machine learning model to expand a chemical space around the input molecule to generate a set of novel molecules by synthesizing custom molecules with an expansion in hit diversity (within the same chemical neighborhood). Furthermore, the AI tech-bio system 106 (via the language machine learning model) leverages the ADMETPrediction tool to predict ADMET properties for the generated set of novel molecules. Indeed, the AI tech-bio system 106 (via the language machine learning model) displays, within the graphical user interface 804*l*, a prompt

864 to indicate the above-mentioned process. Moreover, as shown in FIG. 8K, the AI tech-bio system 106 (via the language machine learning model) generates and displays a response 866 to provide a visualization of the generated set of molecules (e.g., with interactive user interface elements to view SMILES (or SAFE) structures and drug likeness information for the generated molecules). Indeed, the AI tech-bio system 106 can generate various visualizations and/or artifacts to generate a response from the output set of novel molecules (from the ChemicalNeighborExploration tool).

Figure 8L:
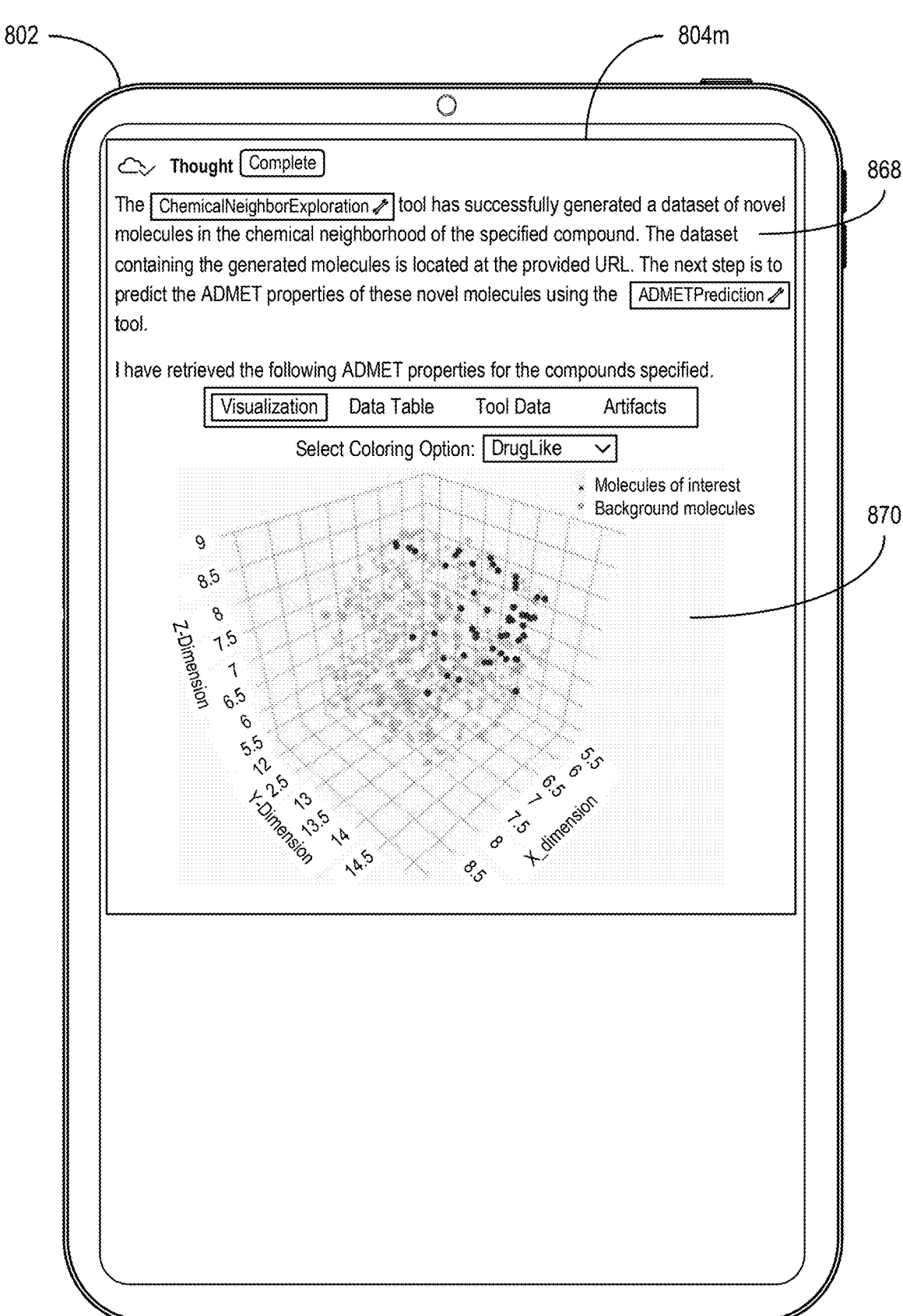

Moreover, as shown in FIG. 8L, the AI tech-bio system 106 continues to execute the workflow described in the prompt 864. For example, as shown in FIG. 8L, the AI tech-bio interface 804*m* of the client device 802, a prompt 868 that indicates the continued execution of the above-mentioned workflow by utilizing the output from the ChemicalNeighborExploration tool with the ADMETPrediction tool to determine ADMET properties for the generated set of novel molecules. Additionally, as shown in FIG. 8L, upon causing the ADMETPrediction tool to generate the ADMET properties, the AI tech-bio system 106 (via the language machine learning model) provides for display, within the graphical user interface 804*m*, a response 870 that includes a visualization of a 3D scatter plot illustrating each molecule and ADMET properties (e.g., upon detecting an interaction with a particular embedding or molecule within the response 870). Indeed, the AI tech-bio system 106 can generate various visualizations and/or artifacts to generate a response from the output ADMET properties for the set of novel molecules (from the ADMETPrediction tool).

Indeed, as shown in FIGS. 8A-8L, the AI tech-bio system 106 utilizes language machine learning models with integration to various tech-bio tools to create a practical application that can quickly initiate, process, visualize, and/or generate data and observations for a digital drug discovery task within a query interface of a tech-bio exploration system (via user query inputs). Indeed, in some cases, the AI tech-bio system 106 (via the language machine learning model) can utilize the executed tasks and data to cause the creation or determination of one or more pharmacological drugs and/or one or more other therapeutic treatments.

Moreover, although FIGS. 8A-8L illustrates a particular workflow or order of tasks, the AI tech-bio system 106 (via the language machine learning model) can receive a variety of tech-bio query prompts (and/or a various orders of prompts) and execute various combinations of tasks in accordance with one or more implementations herein.

In addition, an experiment (or an automated experiment) can include a collection of processes to generate (or create) data to analyze for biological (or chemical) relationships. For instance, an experiment can include experiment components, such as, a collection of machine learning processes, experiment components, testing devices, experiment samples, control variables or configurations, various compound selections or configurations, protein-to-gene mappings, gene imaging, cell imaging, molecular imaging, medical imaging, feature extraction models, and/or data analysis models. Indeed, the experiment design interface system 106 can generate an experiment that includes various inputs and various outputs, from a pipeline of the various experiment components, that are analyzed via one or more data analysis models to determine, predict, and/or observe biological (or chemical) relationships. As an example, a phenomics experiment can include a collection of processes to generate (or create) phenomics data. For example, the tech-bio exploration system 104 can automatically initiate an experiment that utilizes one or more perturbations with one or more cell representations (e.g., in a wet lab or a simulated lab) to generate phenomic images (e.g., images of perturbed cell representations).

Figure 9:
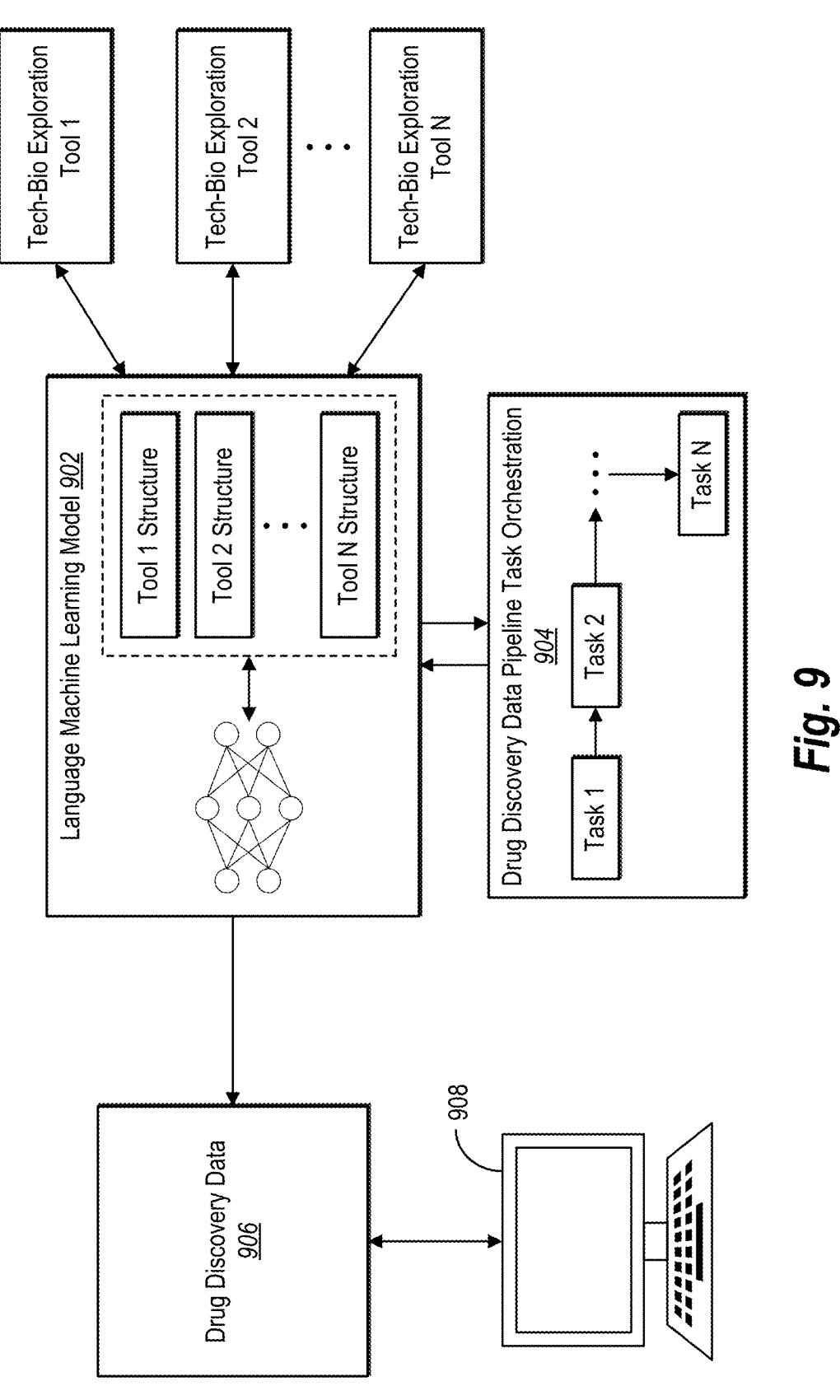
FIG. 9 illustrates an AI tech-bio system facilitating a language machine learning model in an autonomous process to automatically execute various tech-bio exploration tools in accordance with one or more embodiments.

As shown in FIG. 9, the AI tech-bio system 106 utilizes a language machine learning model 902 to learn tool structures of one or more tech-bio exploration tools (e.g., tool structures 1-N for tech-bio exploration tools 1-N). Indeed, the AI tech-bio system 106 can train the language machine learning model 902 in accordance with one or more implementations herein. In particular, the language machine learning model 902 can utilize and/or execute tasks on the tech-bio exploration tools 1-N (as described above).

In one or more instances, the language machine learning model 902 automatically utilizes bio-activity data available via the tech-bio exploration tools 1-N (and/or a bio-activity data repository) to identify various actionable information (e.g., generated hypotheses, queries, target diseases, target compounds). For instance, the language machine learning model 902 can utilize actionable information (in an act 904) and learnings from the tech-bio tool structures to orchestrate drug discovery data pipeline tasks (e.g., tasks 1-N). In particular, the tasks (in the act 904) can include a set of tasks determined by the language machine learning model 902 to execute to test, resolve, and/or generate bio-activity data for the actionable information. In some cases, the set of tasks (in the act 904) can include an experiment design. In some implementations, the language machine learning model 902 identifies previous executions of the tech-bio exploration tools and/or previous experiment designs to generate subsequent and/or variant sets of tasks.

Furthermore, the language machine learning model 902 can automatically generate execution requests for the tasks (e.g., tasks 1-N) based on learning the tech-bio tool structures in accordance with one or more implementations herein. Moreover, the language machine learning model 902 can utilize the generated execution requests to execute one or more processes of the tech-bio exploration tools for the tasks 1-N (in accordance with one or more implementations herein). Indeed, upon execution of the execution requests, the language machine learning model 902 can automatically analyze the outputs of the tech-bio exploration tools 1-N to generate drug discovery data 906 (e.g., bio-activity data, chemistry data). For instance, the generated drug discovery data 906 can include autonomously identified compound-gene relationships, perturbation heatmaps, novel compounds, novel genes, matching genes, matching compounds, targets for particular genes and/or diseases, and/or compounds with similar phenoprints. In particular, the language machine learning model 902 can automatically update a repository of the tech-bio exploration system 104 with the autonomously generated (or discovered) drug discovery data.

In one or more implementations, the AI tech-bio system 106 can, through the language machine learning model 902, continuously and autonomously generate tasks and execute the tasks via the tech-bio exploration tools. Indeed, the AI tech-bio system 106 can utilize the language machine learning model 902 to continuously test for various drug discovery data results, hypotheses, and/or to create drug discovery data (e.g., perturbation maps, perturbation embeddings) for the tech-bio exploration system 104. Indeed, the language machine learning model 902 continuously identifies actionable information and orchestrates tasks to execute on tech-bio exploration tools of the tech-bio exploration system 104 to generate updated drug discovery data for the tech-bio exploration system 104. In addition, the language machine learning model 902 can also continue to learn additional tech-bio exploration tools (e.g., based on updates to existing tech-bio exploration tools and/or identifying a new tech-bio exploration tool).

Moreover, in some cases, as shown in FIG. 9, the AI tech-bio system 106 can receive a request for drug discovery data from a client device. As shown in FIG. 9, the AI tech-bio system 106 can provide drug discovery data 906 (e.g., generated from the autonomous process of the language machine learning model 902) to the client device 908 in accordance with one or more implementations herein. In particular, the AI tech-bio system 106 can provide the drug discovery data 906 to the client device 908 to cause the client device 908 to display the drug discovery data 906.

In addition, as part of the autonomous process of the language machine learning model 902, the AI tech-bio system 106 can automatically transmit drug discovery data to one or more client devices. For instance, the AI tech-bio system 106 can utilize drug discovery data triggers to identify bio-activity data to automatically transmit to one or more client devices. For instance, the AI tech-bio system 106 can configure triggers to identify new compounds, new genes, determinations that satisfy a threshold (e.g., a compound similarity with a satisfied confidence threshold, a threshold number of genes, a threshold number of perturbation heatmaps created), and/or a completion of a particular task. Upon satisfying a trigger, the AI tech-bio system 106 can transmit corresponding drug discovery data to one or more client devices. For instance, the AI tech-bio system 106 can transmit drug discovery data to one or more client devices as notifications, emails, and/or messages.

Figure 10:
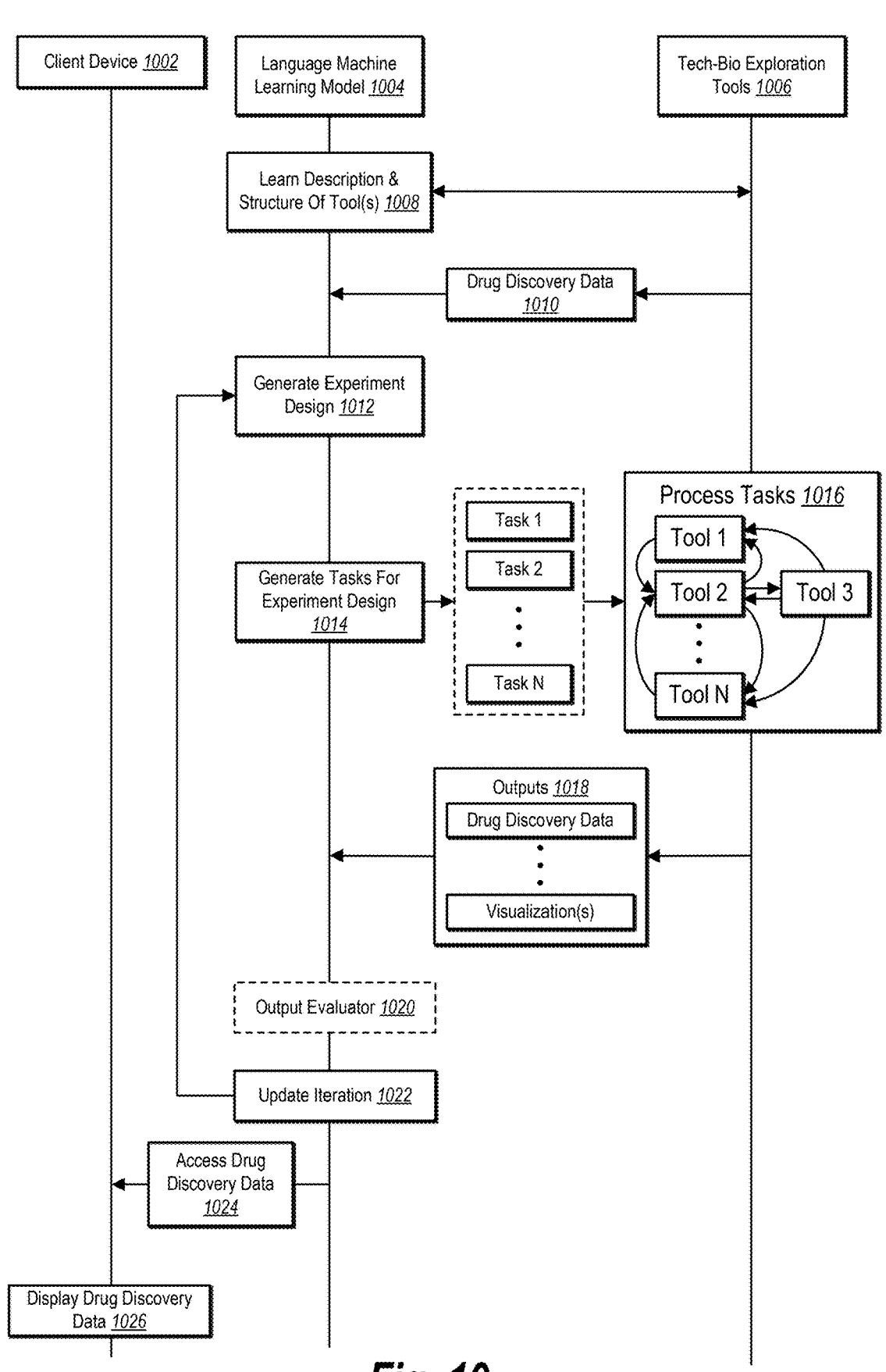
FIG. 10 illustrates a flow diagram of an AI tech-bio system utilizing a language machine learning model within an automated drug discovery data pipeline in accordance with one or more embodiments.

In addition, FIG. 10 illustrates a flow diagram of the AI tech-bio system 106 utilizing a language machine learning model within an automated drug discovery pipeline. Indeed, FIG. 10 illustrates one or more steps or acts of the AI tech-bio system 106 facilitating an autonomous language machine learning model that continuously executes tasks utilizing an understanding of tech-bio exploration tools learned from tech-bio exploration tool structures as described herein (e.g., in relation to FIG. 9).

As shown in FIG. 10, a language machine learning model 1004 interacts with tech-bio exploration tools 1006 to learn descriptions and/or structures of the tools (in an act 1008) in accordance with one or more implementations herein. Moreover, as shown in FIG. 10, the language machine learning model 1004 identifies (or retrieves) drug discovery data 1010 from the tech-bio exploration tools 1006. In some embodiments, the language machine learning model 1004 utilizes the drug discovery data 1010 to determine actionable information (as described above).

Indeed, as shown in an act 1012, the language machine learning model 1004 utilizes drug discovery data 1010 to generate experiment designs (e.g., hypotheses, queries, procedures) to process using the tech-bio exploration tools 1006. Indeed, utilized the experiment design (from the act 1012), the language machine learning model 1004 (in an act 1014) generates tasks for the experiment design (e.g., tasks 1-N) based on the learning of the tech-bio exploration tools (from the act 1008).

Furthermore, as shown in FIG. 10, the language machine learning model 1004 provides the tasks 1-N (as execution requests) to the tech-bio exploration tools 1006 to process tasks in an act 1016 (in accordance with one or more implementations herein). In turn, the tech-bio exploration tools 1006 generate outputs 1018 based on processing the tasks in the act 1016 (e.g., via execution requests). As shown in FIG. 10, the tech-bio exploration tools can process the tasks utilizing various combinations of tools (in the act 1016) in accordance with one or more implementations herein. Furthermore, as shown in FIG. 10, the outputs 1018 from the tech-bio exploration tools 1006 can include drug discovery data and/or visualization(s) for the drug discovery data.

In some cases, the AI tech-bio system 106 (via the language machine learning model 1004) analyzes the outputs 1018 to generate drug discovery data for the tech-bio exploration system 104 (in accordance with one or more implementations). Indeed, in some cases, the language machine learning model 1004 stores the drug discovery data within a drug discovery data repository of the tech-bio exploration system 104.

Moreover, as shown in FIG. 10, the language machine learning model 1004 (in an act 1022) iteratively updates to generate additional experiment designs (in the act 1012) (e.g., as a continuous autonomous process). In particular, the language machine learning model 1004 automatically utilizes updated (or newly obtained) drug discovery data and/or existing drug discovery data to identify additional actionable information. Then, the language machine learning model 1004 automatically generates an experiment design and tasks for the experiment design to utilize with the tech-bio exploration tools as described above.

As further shown in FIG. 10, the client device 1002 (in an act 1024) accesses drug discovery data generated by the (autonomous) language machine learning model 1004. Indeed, the client device 1002 can independently request (or access) the drug discovery data (in an act 1024) while the (autonomous) language machine learning model 1004 continues to generate tasks for the tech-bio exploration tools 1006. As further shown in FIG. 10, the client device 1002, in an act 1026, displays accessed drug discovery data (in accordance with one or more implementations herein). In some cases, the language machine learning model 1004 (or the AI tech-bio system 106) can automatically transmit the drug discovery data (in the act 1024) for display on the client device (in the act 1026) in accordance with one or more implementations herein.

As also shown in FIG. 10, the language machine learning model 1004 can utilize an output evaluator 1020 to evaluate an output of the language machine learning model 1004. For instance, the output evaluator 1020 can analyze an output of the language machine learning model 1004 and/or a trajectory of the language machine learning model 1004 (via a generated sequence of tasks) to determine whether the language machine learning model 1004 is utilizing correct outputs and/or correct trajectories as described above (e.g., in relation to FIG. 4).

Although FIG. 10 illustrates a particular number of client devices, in one or more embodiments, the AI tech-bio system 106 can utilize (or communicate) with a various numbers of client devices. In addition, in one or more implementations, the AI tech-bio system 106 can utilize various numbers of and/or combinations of tasks, execution requests, and/or tech-bio exploration tools and/or generate a variety of outputs and/or visuals from an autonomous language machine learning model(s).

In some implementations, the AI tech-bio system 106 utilizes multiple language machine learning models to autonomously execute tasks and/or tech-bio exploration tools. Indeed, in one or more instances, the AI tech-bio system 106 can utilize specialized language machine learning models that are assigned to particular tech-bio exploration tools to execute, extract, and/or perform tasks on the particular tech-bio exploration tools. Moreover, in one or more embodiments, the AI tech-bio system 106 enables the specialized language machine learning models to communicate and/or interact with each other to autonomously and intelligently navigate and/or generate drug discovery data between the various tech-bio exploration tools.

Figure 11:
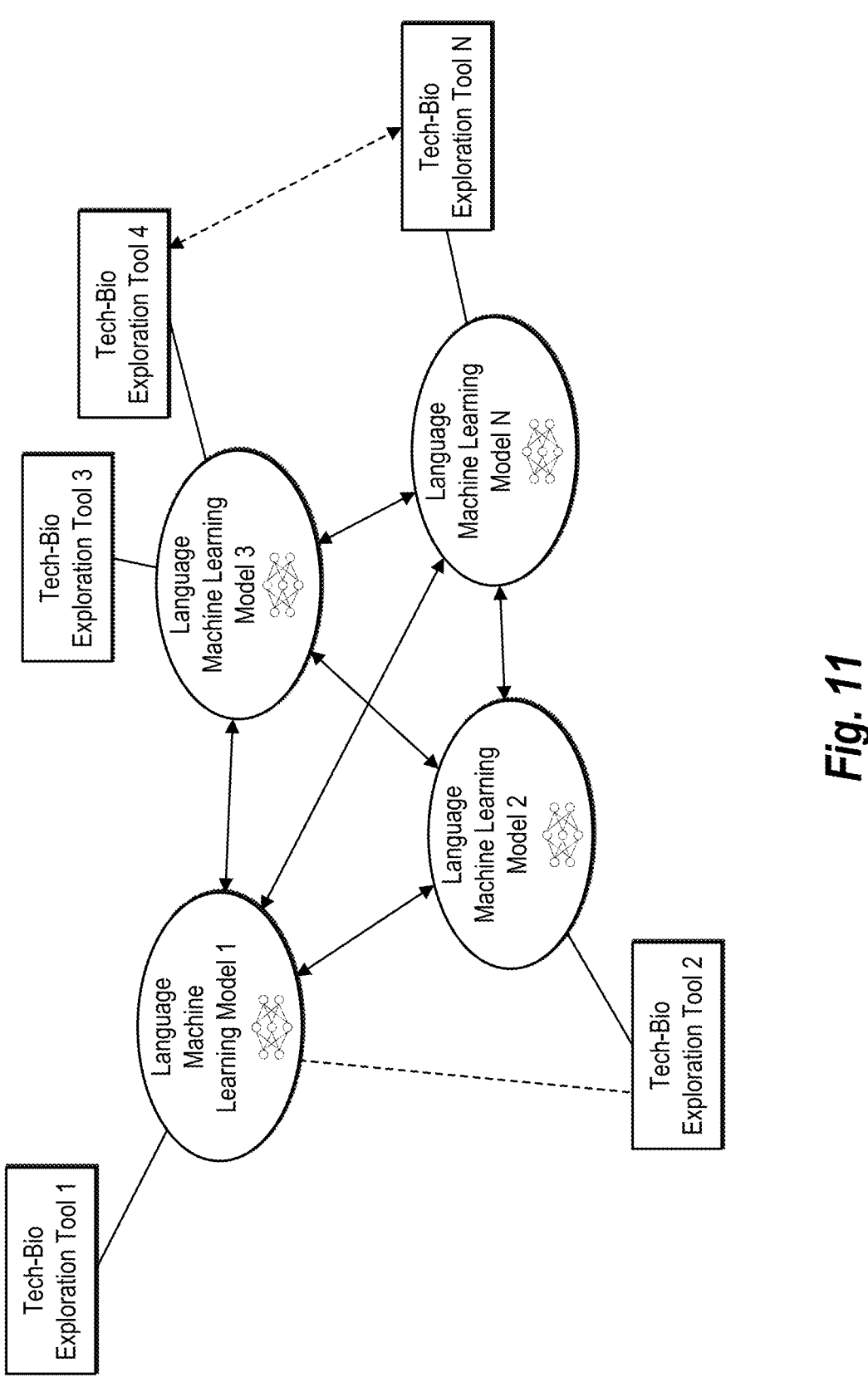
FIG. 11 illustrates an AI tech-bio system utilizing multiple language machine learning models to facilitate an autonomous interaction between the multiple tech-bio exploration tools in accordance with one or more embodiments.

For instance, FIG. 11 illustrates the AI tech-bio system 106 utilizing multiple language machine learning models that are assigned to different tech-bio exploration tools to facilitate an autonomous interaction between the multiple tech-bio exploration tools. As shown in FIG. 11, the AI tech-bio system 106 can train a language machine learning model 1 to learn to interact with a tech-bio exploration tool 1. In addition, as shown in FIG. 11, the AI tech-bio system 106 can train a language machine learning model 2 to learn to interact with a tech-bio exploration tool 2. Moreover, as shown in FIG. 11, the AI tech-bio system 106 can train a language machine learning model 3 to learn to interact with a tech-bio exploration tool 3 and a tech-bio exploration tool 4. Moreover, the AI tech-bio system 106 can train a language machine learning model N to learn to interact with a tech-bio exploration tool N. In some cases, the AI tech-bio system 106 can further train the language machine learning model 1 to also learn to interact with the tech-bio exploration tool 2.

Indeed, in some cases, the language machine learning models can each be trained (as described above) or assigned to a particular tech-bio exploration tool to optimize interactions and/or understandings of the language machine learning models with the particular tech-bio exploration tools. In one or more instances, in reference to FIG. 11, each language machine learning models 1-N is assigned a different role (e.g., a different tech-bio exploration tool). The AI tech-bio system 106, in one or more implementations, facilitates interactions between the language machine learning models 1-N to share and/or generate bio-activity data (or other drug discovery data) between the tech-bio exploration tools. For instance, the language machine learning model 1 can utilize the tech-bio exploration tool 1 to generate biological mappings, the language machine learning model 2 can utilize the tech-bio exploration tool 2 to perform chemistry tasks to optimize scaffolding with respect to predictive model outputs provided by the language machine learning model 3 (through the tech-bio exploration tool 3).

As further shown in FIG. 11, the AI tech-bio system 106 can assign a language machine learning model (e.g., language machine learning model 1) to multiple tech-bio exploration tools (e.g., tech-bio exploration tools 1 and 2). Furthermore, in some cases, the AI tech-bio system 106 can facilitate interactions between tech-bio exploration tools (e.g., tech-bio exploration tool 4 can directly interact with the tech-bio exploration tool N).

In addition, the various language machine learning models 1-N can, independently and/or via interactions, generate bio-activity data. In one or more instances, the AI tech-bio system 106 stores the bio-activity data within the bio-activity data repository of the tech-bio exploration system 104. In some cases, the AI tech-bio system 106 can provide access to the generated bio-activity data (via a client device request for access) and/or automatically upon satisfying a trigger as described above (e.g., in relation to FIGS. 9 and 10).

Furthermore, as mentioned above, the AI tech-bio system 106 can interface and/or interact with a variety of tech-bio exploration tools. As an example, the AI tech-bio system 106 (via the language machine learning model(s) described above) can interface and/or interact with (in accordance with one or more implementations herein) a tech-bio exploration tool that implements a molecular design model. Indeed, the AI tech-bio system 106 can utilize a molecular design modeling system (as a tech-bio exploration tool) that generates molecular string representations for molecular constructions with one or more desired characteristics (e.g., a molecular string representation in a molecular line notation).

In particular, the molecular design modeling system, as a tech-bio exploration tool, can extract attributes (e.g., unique ring digits) from a molecule to fragment the attributes as a set of bonds, sorting the fragments, and generate a string that simulates fragment linking to generate a unique representation of a molecule in a string. Indeed, in order to generate the molecular representation, the molecular design modeling system can utilize a sequential attachment-based fragment embedding (SAFE) line notation for molecules (e.g., to represent molecules as an unordered sequence of fragment blocks). In addition, the molecular design modeling system can utilize a fragment-based design that facilitates de novo generation, scaffold decoration and motif extension, linker design and scaffold morphing, and superstructure generation in a molecular string representation. Moreover, the molecular design modeling system can utilize a molecular string representation generative model (e.g., a SAFE-GPT model) that is trained to generate molecular designs (and molecular string representations for the molecular designs).

Indeed, in some implementations, a tech-bio exploration tool includes a molecular design modeling system (e.g., a SAFE line notation) as described in GENERATING LARGE-LANGUAGE-MODEL COMPATIBLE SEQUENTIAL ATTACHMENT-BASED FRAGMENT EMBEDDING MOLECULAR REPRESENTATIONS, U.S. patent application Ser. No. 18/750,828, filed Jun. 21, 2024 and also described in Emmanuel Noutahi et. al., Gotta be SAFE: A New Framework for Molecular Design, arXiv, arXiv: 2310.10773v2 (2023), both of which are incorporated herein by reference in their entirety.

Figure 12:
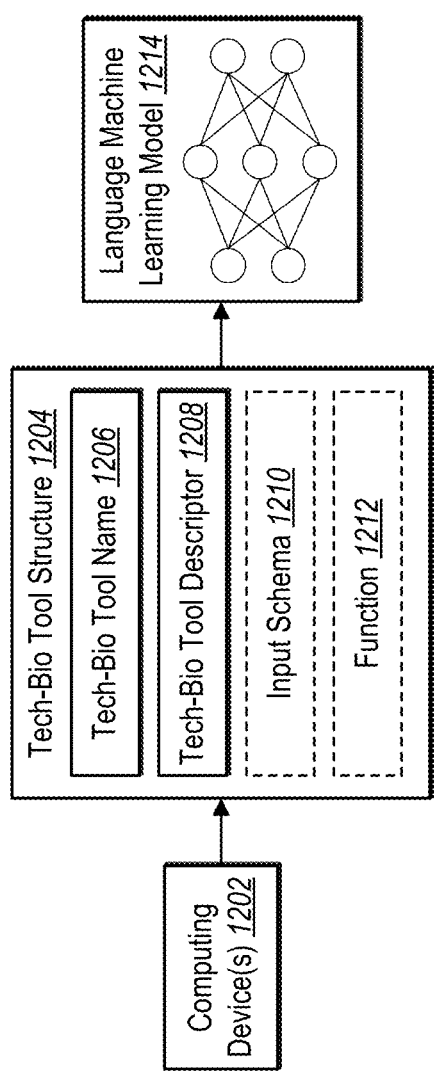
FIG. 12 illustrates an AI tech-bio system adding a tech-bio exploration tool to a language machine learning model in accordance with one or more embodiments.

In some instances, the AI tech-bio system 106 (via the language machine learning model) enables the addition of one or more tech-bio exploration tools. For instance, FIG. 12 illustrates the AI tech-bio system 106 adding a tech-bio exploration tool to utilize the tech-bio exploration tool (via the language machine learning model) for one or more tasks (in response to a tech-bio query as described above). For example, as shown in FIG. 12, the AI tech-bio system 106 receives, from computing device(s) 1202, a tech-bio tool structure 1204. Indeed, the tech-bio tool structure 1204 can include a tech-bio tool name 1206 and a tech-bio tool descriptor 1208. Furthermore, in some cases, the tech-bio tool structure 1204 can include an input schema 1210 and/or a function 1212. Indeed, as illustrated in FIG. 12, the AI tech-bio system 106 provides the tech-bio tool structure 1204 to a language machine learning model 1214 to cause the language machine learning model 1214 to learn the tech-bio tool (or context of the tech-bio tool) (e.g., via few-shot learning) as described above.

Indeed, in one or more instances, the AI tech-bio system 106 utilizes a tech-bio tool structure that describes the utility of a tech-bio tool. For example, the tech-bio tool structure can describe the types of inputs the tech-bio tool (or a model of the tech-bio tool) utilize, the function of the tech-bio tool, the process of the tech-bio tool, the outputs of the tech-bio tool, and/or the output formats of the tech-bio tool. Moreover, the tech-bio tool structure can also include a schema (e.g., a JSON schema) that describes the function of a model, input values for the tech-bio tool (and a format or syntax for the input data), and/or outputs of the tech-bio tool (and a format or syntax for the output data). In some instances, the AI tech-bio system 106 can retrieve tech-bio tool structure data by utilizing a tool parameter function call (e.g., tool_args) with a tech-bio tool to pull the tech-bio tool structure data.

Indeed, the AI tech-bio system 106 can enable the addition of a tech-bio tool to the language machine learning model via a tech-bio tool design interface. In particular, the AI tech-bio system 106 can display a tech-bio tool design interface that includes input elements for the various input data of the tech-bio tool structure to integrate a tech-bio tool to the language machine learning model. In some cases, the AI tech-bio system 106 can receive a tech-bio tool structure as a prompt (e.g., a text prompt) in relation to the language machine learning model.

Figure 13:
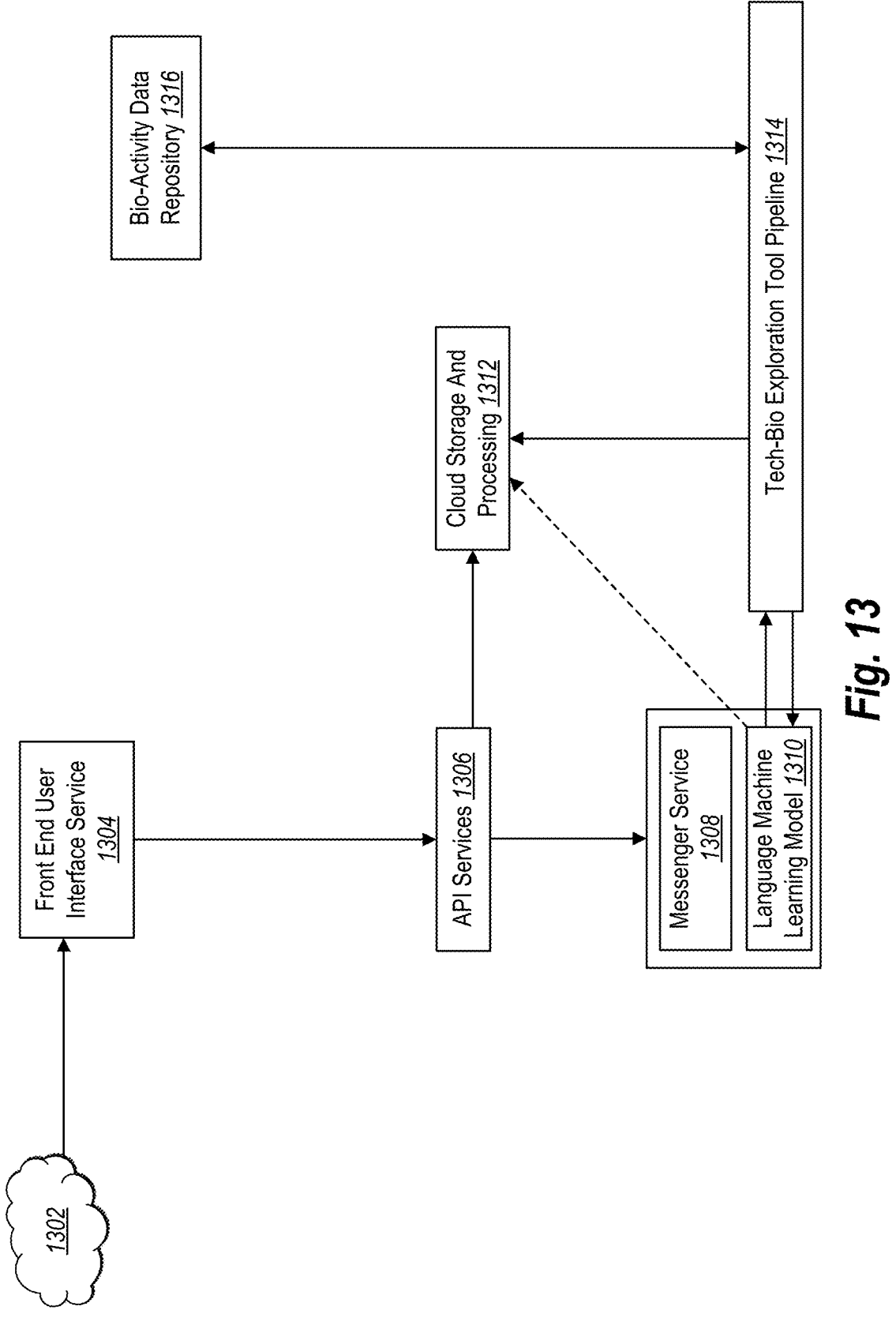
FIG. 13 illustrates a flow diagram of a network environment in which an AI tech-bio system operates in accordance with one or more embodiments.

Furthermore, FIG. 13 illustrates a flow diagram of a network environment in which the AI tech-bio system 106 operates. For instance, as shown in FIG. 13, a network 1302 can communicate with a front end user interface service 1304 to receive and/or send data to client devices. In particular, the front end user interface service 1304 can facilitate an interactive user interface (e.g., a chat interface as described above) to communicate with a messenger service 1308 and a language machine learning model 1310 via API services 1306 to receive query prompts and/or send bio-activity data (e.g., as a SaaS service) in accordance with one or more implementations herein. Furthermore, as shown in FIG. 13, the language machine learning model 1310 interacts with a tech-bio exploration tool pipeline 1314 to execute one or more tasks on tech-bio exploration tools (as described above) to generate and/or retrieve bio-activity data from a bio-activity data repository 1316 (in accordance with one or more implementations herein). Moreover, as shown in FIG. 13, the language machine learning model 1310 and/or the tech-bio exploration tool pipeline 1314 can utilize cloud storage and processing 1312 to obtain, generate, and/or transmit bio-activity data to client devices via the network 1302 (e.g., using a front end user interface service 1304).

FIGS. 1-13, the corresponding text, and the examples provide a number of different systems, methods, and non-transitory computer readable media for utilizing a language machine learning model to execute one or more tech-bio exploration tool tasks in accordance with one or more implementations. In addition to the foregoing, embodiments can also be described in terms of flowcharts comprising acts for accomplishing a particular result. For example, FIGS. 14 and 15 illustrate flowcharts of example sequences of acts in accordance with one or more embodiments.

While FIGS. 14 and 15 illustrate acts according to some embodiments, alternative embodiments may omit, add to, reorder, and/or modify any of the acts shown in FIGS. 14 and 15. The acts of FIGS. 14 and 15 can be performed as part of a method. Alternatively, a non-transitory computer readable medium can comprise instructions, that when executed by one or more processors, cause a computing device to perform the acts of FIGS. 14 and 15. In still further embodiments, a system can perform the acts of FIGS. 14 and 15. Additionally, the acts described herein may be repeated or performed in parallel with one another or in parallel with different instances of the same or other similar acts (e.g., between FIGS. 14 and 15).

Indeed, FIG. 14 illustrates an example series of acts 1400 for utilizing a language machine learning model to execute one or more tech-bio exploration tool tasks in accordance with one or more embodiments. For example, as shown in FIG. 14, the series of acts 1400 include an act 1402 of utilizing a language machine learning model to generate an execution request for one or more tech-bio exploration tools, an act 1404 of transmitting the execution request to execute one or more tasks on the one or more tech-bio exploration tools, and an act 1406 of generating a response utilizing data outputs from the one or more tech-bio exploration tools.

In one or more embodiments, the series of acts 1400 can include identifying, from a client device, a prompt indicating a tech-bio query, utilizing a language machine learning model to generate an execution request indicating one or more tasks for one or more tech-bio exploration tools, wherein the language machine learning model is trained to recognize one or more tool structures of the one or more tech-bio exploration tools, transmitting the execution request to the one or more tech-bio exploration tools to cause the one or more one or more tech-bio exploration tools to execute the one or more tasks based on the tech-bio query, and based on one or more data outputs of the one or more executed tasks of the one or more one or more tech-bio exploration tools, utilizing the language machine learning model to generate, for display within the client device, a response to the tech-bio query.

In some cases, the series of acts 1400 can include identifying, from a client device, a tech-bio query, generating one or more language model prompts from the tech-bio query, wherein the one or more language model prompts comprises one or more descriptions of a plurality of tech-bio exploration tools, generating, utilizing a language machine learning model from one or more language model prompts, an execution request indicating a task for a tech-bio exploration tool of the plurality of tech-bio exploration tools, transmitting the execution request to the tech-bio exploration tool to cause the tech-bio exploration tool to execute the task, and, based on one or more data outputs of the tech-bio exploration tool, utilizing the language machine learning model to generate a response to the tech-bio query.

In one or more implementations, the series of acts 1400 include utilizing the one or more language model prompts as few-shot learning prompts to enable in-context learning for the language machine learning model from the one or more descriptions of the plurality of tech-bio exploration tools.

Moreover, the series of acts 1400 can include generating the execution request comprises utilizing the language machine learning model to select the tech-bio exploration tool from a plurality of tech-bio exploration tools.

In addition, the series of acts 1400 can include generating the execution request by generating, utilizing the language machine learning model, a set of instructions to utilize the selected tech-bio exploration tool to generate the one or more data outputs for the tech-bio query. Moreover, the series of acts 1400 can include providing, for display within a graphical user interface of the client device, a representation of the selected tech-bio exploration tool.

In some cases, the tech-bio query can include free-form text for a request for a tech-bio data output response.

Additionally, the series of acts 1400 can include, in response to receiving the one or more data outputs from the tech-bio exploration tool generating one or more additional language model prompts from the one or more data outputs of the tech-bio exploration tool and/or utilizing the language machine learning model to select between generating the response to the tech-bio query or executing an additional tech-bio tool from the one or more additional language model prompts.

In addition, the series of acts 1400 can include, in response to the language machine learning model selecting to generate the response, providing, for display within a graphical user interface of the client device, the response to the tech-bio query. For example, the response includes at least one of a text output, a visual diagram output, or a data file output.

Moreover, the series of acts 1400 can include, in response to the language machine learning model selecting to execute the additional tech-bio tool generating, utilizing the language machine learning model from the one or more additional language model prompts, an additional execution request indicating an additional task for the additional tech-bio exploration tool of the plurality of tech-bio exploration tools, transmitting the additional execution request to the additional tech-bio exploration tool to cause the additional tech-bio exploration tool to execute the additional task, and/or based on one or more additional data outputs of the additional tech-bio exploration tool, utilizing the language machine learning model to generate an additional response.

Additionally, the series of acts 1400 can include generating one or more additional language model prompts from an additional tech-bio query identified from the client device, transmitting an additional execution request generated from the one or more additional language model prompts to an additional tech-bio exploration tool to cause the additional tech-bio exploration tool to execute an additional task, and/or, based on one or more additional outputs of the additional tech-bio exploration tool, utilizing the language machine learning model to generate an additional response to the additional tech-bio query.

Moreover, FIG. 15 illustrates an example series of acts 1500 for utilizing a language machine learning model with selectable tech-bio query prompt templates to execute one or more tech-bio exploration tool tasks in accordance with one or more embodiments. For example, as shown in FIG. 15, the series of acts 1500 include an act 1502 of displaying a tech-bio selector for tech-bio query prompt templates, an act 1504 of displaying a tech-bio query template and a perturbation input element in response to a selection within the tech-bio selector, an act 1506 of generating a tech-bio query output response utilizing a language machine learning model to execute a tech-bio exploration tool based on the tech-bio query template and the perturbation, and an act 1508 of displaying a tech-bio query output response and the tech-bio prompt selector.

In one or more embodiments, the series of acts 1500 can include providing, for display within a graphical user interface of a client device, a tech-bio prompt selector corresponding to a plurality of tech-bio query prompt templates, in response to receiving a selection of a tech-bio query prompt template of the plurality of tech-bio query prompt templates via the tech-bio prompt selector, providing, for display within the graphical user interface of the client device, the tech-bio query prompt template and a perturbation input element, based on receiving input of a perturbation via the perturbation input element, generating a tech-bio query output response by utilizing a language machine learning model to execute one or more tech-bio exploration tools based on the tech-bio query prompt template and the perturbation, and providing, for display within the graphical user interface of the client device, the tech-bio query output response and the tech-bio prompt selector.

In addition, the series of acts 1500 can include providing the tech-bio prompt selector corresponding to the plurality of tech-bio query prompt templates by providing at least two of the following: a compound-gene activity query prompt template, a molecular pair series prompt template, a phenomic clustering query prompt template, a comparison diagram prompt template, or a mechanism-of-action query template.

Moreover, the series of acts 1500 can include, in response to the selection of the tech-bio query prompt template of the plurality of tech-bio query prompt templates via the tech-bio prompt selector, selecting, utilizing the language machine learning model, a tech-bio exploration tool from at least two of the following tech-bio exploration tools: a compound-gene activity modeling tool, a molecular pair series assignment tool, a phenomic clustering tool, a cluster analysis comparison tool, or a mechanism-of-action modeling tool.

Additionally, the series of acts 1500 can include, in response to receiving a selection of the compound-gene activity query prompt template, utilizing the language machine learning model to generate the tech-bio query output response by executing a compound-gene activity modeling tool to generate a perturbation activity score between the input perturbation and a plurality of compounds.

Moreover, the series of acts 1500 can include, in response to receiving a selection of the molecular pair series prompt template, generating the tech-bio query output response by identifying, by utilizing the language machine learning model, a plurality of compounds for the input perturbation and/or executing, by utilizing the language machine learning model, a molecular pair series assignment tool to generate matched molecular pair series from compound groupings of the plurality of compounds based on a network graph.

In addition, the series of acts 1500 can include, in response to receiving a selection of the phenomic clustering query prompt template, utilize the language machine learning model to generate the tech-bio query output response by executing a phenomic clustering tool to generate one or more compound clusters based on phenomic properties from a plurality of compounds associated with the input perturbation.

Moreover, the series of acts 1500 can include receiving a selection of the comparison diagram prompt template, identifying, utilizing the language machine learning model, one or more matched molecular pair series associated with the input perturbation and one or more phenomic compound clusters associated with the input perturbation, and/or generating, by the language machine learning model, a comparison diagram for the tech-bio query output response by executing a cluster analysis comparison tool to compare the one or more matched molecular pair series and the one or more phenomic compound clusters.

In addition, the series of acts 1500 can include, in response to receiving a selection of the mechanism-of-action query template and one or more compounds associated with the input perturbation, utilizing the language machine learning model to generate the tech-bio query output response by executing a mechanism-of-action modeling tool to generate mechanism-of-action data for the one or more compounds associated with the input perturbation, wherein the mechanism-of-action data comprises a mechanism-of-action prediction heatmap for the one or more compounds or a set of predicted mechanism-of actions for a compound from the one or more compounds.

Additionally, the series of acts 1500 can include, in response to receiving an additional selection of an additional tech-bio query prompt template of the plurality of tech-bio query prompt templates via the tech-bio prompt selector, generating an additional tech-bio query output response by utilizing the language machine learning model to execute the one or more tech-bio exploration tools based on the additional tech-bio query prompt template and the tech-bio query output response and/or providing, for display within the graphical user interface of the client device, the additional tech-bio query output response and the tech-bio prompt selector.

Embodiments of the present disclosure may comprise or utilize a special purpose or general-purpose computer including computer hardware, such as, for example, one or more processors and system memory, as discussed in greater detail below. Implementations within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, implementations of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed by a processor, cause a general-purpose computer, special purpose computer, or special purpose processing device to perform a certain function or group of functions. In some implementations, computer-executable instructions are executed on a general-purpose computer to turn the general-purpose computer into a special purpose computer implementing elements of the disclosure. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multiprocessor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Implementations of the present disclosure can also be implemented in cloud computing environments. In this description, "cloud computing" is defined as a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 16:
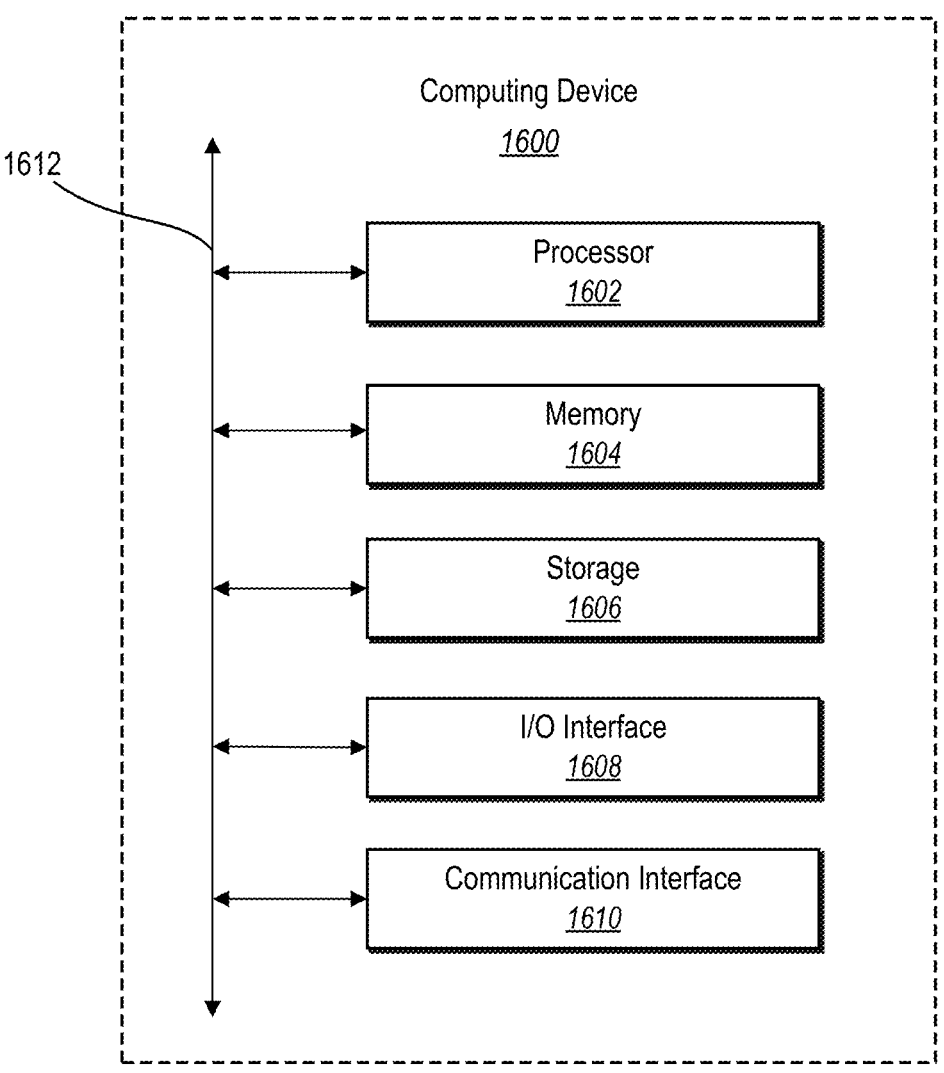
FIG. 16 illustrates a block diagram of an example computing device for implementing one or more embodiments of the present disclosure.

FIG. 16 illustrates a block diagram of exemplary computing device 1600 (e.g., the server(s) 102 and/or the client device(s) 110) that may be configured to perform one or more of the processes described above. One will appreciate that server(s) 102 and/or the client device(s) 110 may comprise one or more computing devices such as computing device 1600. As shown by FIG. 16, computing device 1600 can comprise processor 1602, memory 1604, storage device 1606, I/O interface 1608, and communication interface 1610, which may be communicatively coupled by way of communication infrastructure 1612. While an exemplary computing device 1600 is shown in FIG. 16, the components illustrated in FIG. 16 are not intended to be limiting. Additional or alternative components may be used in other implementations. Furthermore, in certain implementations, computing device 1600 can include fewer components than those shown in FIG. 16. Components of computing device 1600 shown in FIG. 16 will now be described in additional detail.

In particular implementations, processor 1602 includes hardware for executing instructions, such as those making up a computer program. As an example and not by way of limitation, to execute instructions, processor 1602 may retrieve (or fetch) the instructions from an internal register, an internal cache, memory 1604, or storage device 1606 and decode and execute them. In particular implementations, processor 1602 may include one or more internal caches for data, instructions, or addresses. As an example and not by way of limitation, processor 1602 may include one or more instruction caches, one or more data caches, and one or more translation lookaside buffers (TLBs). Instructions in the instruction caches may be copies of instructions in memory 1604 or storage device 1606.

Memory 1604 may be used for storing data, metadata, and programs for execution by the processor(s). Memory 1604 may include one or more of volatile and non-volatile memories, such as Random Access Memory ("RAM"), Read Only Memory ("ROM"), a solid state disk ("SSD"), Flash, Phase Change Memory ("PCM"), or other types of data storage. Memory 1604 may be internal or distributed memory.

Storage device 1606 includes storage for storing data or instructions. As an example and not by way of limitation, storage device 1606 can comprise a non-transitory storage medium described above. Storage device 1606 may include a hard disk drive (HDD), a floppy disk drive, flash memory, an optical disc, a magneto-optical disc, magnetic tape, or a Universal Serial Bus (USB) drive or a combination of two or more of these. Storage device 1606 may include removable or non-removable (or fixed) media, where appropriate. Storage device 1606 may be internal or external to computing device 1600. In particular implementations, storage device 1606 is non-volatile, solid-state memory. In other implementations, Storage device 1606 includes read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these.

I/O interface 1608 allows a user to provide input to, receive output from, and otherwise transfer data to and receive data from computing device 1600. I/O interface 1608 may include a mouse, a keypad or a keyboard, a touch screen, a camera, an optical scanner, network interface, modem, other known I/O devices or a combination of such I/O interfaces. I/O interface 1608 may include one or more devices for presenting output to a user, including, but not limited to, a graphics engine, a display (e.g., a display screen), one or more output drivers (e.g., display drivers), one or more audio speakers, and one or more audio drivers. In certain implementations, I/O interface 1608 is configured to provide graphical data to a display for presentation to a user. The graphical data may be representative of one or more graphical user interfaces and/or any other graphical content as may serve a particular implementation.

Communication interface 1610 can include hardware, software, or both. In any event, communication interface 1610 can provide one or more interfaces for communication (such as, for example, packet-based communication) between computing device 1600 and one or more other computing devices or networks. As an example and not by way of limitation, communication interface 1610 may include a network interface controller (NIC) or network adapter for communicating with an Ethernet or other wire-based network or a wireless NIC (WNIC) or wireless adapter for communicating with a wireless network, such as a WI-FI.

Additionally or alternatively, communication interface 1610 may facilitate communications with an ad hoc net-work, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, communication interface 1610 may facili-tate communications with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination thereof.

Additionally, communication interface 1610 may facili-tate communications various communication protocols. Examples of communication protocols that may be used include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), User Datagram Protocol ("UDP"), Global System for Mobile Communications ("GSM") technologies, Code Division Multiple Access ("CDMA") technologies, Time Division Multiple Access ("TDMA") technologies, Short Message Service ("SMS"), Multimedia Message Service ("MMS"), radio frequency ("RF") signaling technologies, Long Term Evolution ("LTE") technologies, wireless communication technologies, in-band and out-of-band signaling technolo-gies, and other suitable communications networks and tech-nologies.

Communication infrastructure 1612 may include hard-ware, software, or both that couples components of com-puting device 1600 to each other. As an example and not by way of limitation, communication infrastructure 1612 may include an Accelerated Graphics Port (AGP) or other graph-ics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Ex-press (PCIe) bus, a serial advanced technology attachment (SATA) bus, a Video Electronics Standards Association local (VLB) bus, or another suitable bus or a combination thereof.

In the foregoing specification, the invention has been described with reference to specific example embodiments thereof. Various embodiments and aspects of the invention(s) are described with reference to details discussed herein, and the accompanying drawings illustrate the various embodiments. The description above and drawings are illus-trative of the invention and are not to be construed as limiting the invention. Numerous specific details are described to provide a thorough understanding of various embodiments of the present invention.

The present invention may be embodied in other specific forms without departing from its spirit or essential charac-teristics. The described embodiments are to be considered in all respects only as illustrative and not restrictive. For example, the methods described herein may be performed with less or more steps/acts or the steps/acts may be per-formed in differing orders. Additionally, the steps/acts described herein may be repeated or performed in parallel to one another or in parallel to different instances of the same or similar steps/acts. The scope of the invention is, therefore, indicated by the appended claims rather than by the fore-going description. All changes that come within the meaning and range of equivalency of the claims are to be embraced within their scope.

What is claimed is:

1. A computer-implemented method comprising:

providing, for display within a graphical user interface of a client device, a tech-bio prompt selector correspond-ing to a plurality of tech-bio query prompt templates, wherein a tech-bio query prompt template from the plurality of tech-bio query prompt templates comprises one or more queries to cause a language machine learning model to execute one or more tech-bio explo-ration tools;

in response to receiving a selection of a tech-bio query prompt template of the plurality of tech-bio query prompt templates via the tech-bio prompt selector, providing, for display within the graphical user inter-face of the client device, the tech-bio query prompt template and a perturbation input element;

based on receiving input of a perturbation via the pertur-bation input element, generating a tech-bio query out-put response by utilizing the language machine learning model to execute the one or more tech-bio exploration tools based on the tech-bio query prompt template and the perturbation; and providing, for display within the graphical user interface of the client device, the tech-bio query output response and the tech-bio prompt selector.

2. The computer-implemented method of claim 1, wherein providing the tech-bio prompt selector correspond-ing to the plurality of tech-bio query prompt templates comprises providing at least two of a compound-gene activ-ity query prompt template, a molecular pair series prompt template, a phenomic clustering query prompt template, a comparison diagram prompt template, or a mechanism-of-action query template.

3. The computer-implemented method of claim 2, further comprising, in response to the selection of the tech-bio query prompt template of the plurality of tech-bio query prompt templates via the tech-bio prompt selector, selecting, utiliz-ing the language machine learning model, a tech-bio explo-ration tool from a compound-gene activity modeling tool, a molecular pair series assignment tool, a phenomic clustering tool, a cluster analysis comparison tool, or a mechanism-of-action modeling tool.

4. The computer-implemented method of claim 2, further comprising, in response to receiving a selection of the compound-gene activity query prompt template, utilizing the language machine learning model to generate the tech-bio query output response by executing a compound-gene activity modeling tool to generate a perturbation activity score between the input perturbation and a plurality of compounds.

5. The computer-implemented method of claim 2, further comprising, in response to receiving a selection of the molecular pair series prompt template, generating the tech-bio query output response by:

identifying, by utilizing the language machine learning model, a plurality of compounds for the input perturbation; and executing, by utilizing the language machine learning model, a molecular pair series assignment tool to generate matched molecular pair series from compound groupings of the plurality of compounds based on a network graph.

6. The computer-implemented method of claim 2, further comprising, in response to receiving a selection of the phenomic clustering query prompt template, utilize the language machine learning model to generate the tech-bio query output response by executing a phenomic clustering tool to generate one or more compound clusters based on phenomic properties from a plurality of compounds associated with the input perturbation.

7. The computer-implemented method of claim 2, further comprising:

receiving a selection of the comparison diagram prompt template;

identifying, utilizing the language machine learning model, one or more matched molecular pair series associated with the input perturbation and one or more phenomic compound clusters associated with the input perturbation; and generating, by the language machine learning model, a comparison diagram for the tech-bio query output response by executing a cluster analysis comparison tool to compare the one or more matched molecular pair series and the one or more phenomic compound clusters.

8. The computer-implemented method of claim 2, further comprising, in response to receiving a selection of the mechanism-of-action query template and one or more compounds associated with the input perturbation, utilizing the language machine learning model to generate the tech-bio query output response by executing a mechanism-of-action modeling tool to generate mechanism-of-action data for the one or more compounds associated with the input perturbation, wherein the mechanism-of-action data comprises a mechanism-of-action prediction heatmap for the one or more compounds or a set of predicted mechanism-of actions for a compound from the one or more compounds.

9. The computer-implemented method of claim 1, further comprising:

in response to receiving an additional selection of an additional tech-bio query prompt template of the plurality of tech-bio query prompt templates via the tech-bio prompt selector, generating an additional tech-bio query output response by utilizing the language machine learning model to execute the one or more tech-bio exploration tools based on the additional tech-bio query prompt template and the tech-bio query output response; and providing, for display within the graphical user interface of the client device, the additional tech-bio query output response and the tech-bio prompt selector.

10. A non-transitory computer-readable medium storing instructions that, when executed by at least one processor, cause a computing device to:

provide, for display within a graphical user interface of a client device, a tech-bio prompt selector corresponding to a plurality of tech-bio query prompt templates, wherein a tech-bio query prompt template from the plurality of tech-bio query prompt templates comprises one or more queries to cause a language machine learning model to execute one or more tech-bio exploration tools;

in response to receiving a selection of a tech-bio query prompt template of the plurality of tech-bio query prompt templates via the tech-bio prompt selector, provide, for display within the graphical user interface of the client device, the tech-bio query prompt template and a perturbation input element;

based on receiving input of a perturbation via the perturbation input element, generate a tech-bio query output response by utilizing the language machine learning model to execute the one or more tech-bio exploration tools based on the tech-bio query prompt template and the perturbation; and provide, for display within the graphical user interface of the client device, the tech-bio query output response and the tech-bio prompt selector.

11. The non-transitory computer-readable medium of claim 10, wherein the instructions cause the computing device to provide the tech-bio prompt selector corresponding to the plurality of tech-bio query prompt templates by providing at least two of a compound-gene activity query prompt template, a molecular pair series prompt template, a phenomic clustering query prompt template, a comparison diagram prompt template, or a mechanism-of-action query template.

12. The non-transitory computer-readable medium of claim 11, wherein the instructions cause the computing device to, in response to the selection of the tech-bio query prompt template of the plurality of tech-bio query prompt templates via the tech-bio prompt selector, select, utilizing the language machine learning model, a tech-bio exploration tool from a compound-gene activity modeling tool, a molecular pair series assignment tool, a phenomic clustering tool, a cluster analysis comparison tool, or a mechanism-of-action modeling tool.

13. The non-transitory computer-readable medium of claim 11, wherein the instructions cause the computing device to, in response to receiving a selection of the compound-gene activity query prompt template, utilize the language machine learning model to generate the tech-bio query output response by executing a compound-gene activity modeling tool to generate a perturbation activity score between the input perturbation and a plurality of compounds.

14. The non-transitory computer-readable medium of claim 11, wherein the instructions cause the computing device to, in response to receiving a selection of the molecular pair series prompt template, generate the tech-bio query output response by:

identifying, by utilizing the language machine learning model, a plurality of compounds for the input perturbation; and executing, by utilizing the language machine learning model, a molecular pair series assignment tool to generate matched molecular pair series from compound groupings of the plurality of compounds based on a network graph.

15. The non-transitory computer-readable medium of claim 11, wherein the instructions cause the computing device to, in response to receiving a selection of the phenomic clustering query prompt template, utilize the language machine learning model to generate the tech-bio query output response by executing a phenomic clustering tool to generate one or more compound clusters based on phenomic properties from a plurality of compounds associated with the input perturbation.

16. A system comprising:

at least one processor; and at least one non-transitory computer-readable storage medium storing instructions that, when executed by the at least one processor, cause the system to:

provide, for display within a graphical user interface of a client device, a tech-bio prompt selector corresponding to a plurality of tech-bio query prompt templates, wherein a tech-bio query prompt template from the plurality of tech-bio query prompt templates comprises one or more queries to cause a language machine learning model to execute one or more tech-bio exploration tools;

in response to receiving a selection of a tech-bio query prompt template of the plurality of tech-bio query prompt templates via the tech-bio prompt selector, provide, for display within the graphical user interface of the client device, the tech-bio query prompt template and a perturbation input element;

based on receiving input of a perturbation via the perturbation input element, generate a tech-bio query output response by utilizing the language machine learning model to execute the one or more tech-bio exploration tools based on the tech-bio query prompt template and the perturbation; and provide, for display within the graphical user interface of the client device, the tech-bio query output response and the tech-bio prompt selector.

17. The system of claim 16, wherein the instructions cause the system to provide the tech-bio prompt selector corresponding to the plurality of tech-bio query prompt templates by providing at least two of a compound-gene activity query prompt template, a molecular pair series prompt template, a phenomic clustering query prompt template, a comparison diagram prompt template, or a mechanism-of-action query template.

18. The system of claim 17, wherein the instructions cause the system to, in response to receiving a selection of the compound-gene activity query prompt template, utilize the language machine learning model to generate the tech-bio query output response by executing a compound-gene activity modeling tool to generate a perturbation activity score between the input perturbation and a plurality of compounds.

19. The system of claim 17, wherein the instructions cause the system to, in response to receiving a selection of the phenomic clustering query prompt template, utilize the language machine learning model to generate the tech-bio query output response by executing a phenomic clustering tool to generate one or more compound clusters based on phenomic properties from a plurality of compounds associated with the input perturbation.

20. The system of claim 17, wherein the instructions cause the system to, in response to receiving a selection of the mechanism-of-action query template and one or more compounds associated with the input perturbation, utilizing the language machine learning model to generate the tech-bio query output response by executing a mechanism-of-action modeling tool to generate mechanism-of-action data for the one or more compounds associated with the input perturbation, wherein the mechanism-of-action data comprises a mechanism-of-action prediction heatmap for the one or more compounds or a set of predicted mechanisms-of-action for a compound from the one or more compounds.

\* \* \* \* \*